US011219686B2

(12) United States Patent
Rao

(10) Patent No.: US 11,219,686 B2
(45) Date of Patent: *Jan. 11, 2022

(54) DUAL ANTHRAX-PLAGUE VACCINES THAT CAN PROTECT AGAINST TWO TIER-1 BIOTERROR PATHOGENS, BACILLUS ANTHRACIS AND YERSINIA PESTIS

(71) Applicant: The Catholic University of America, Washington, DC (US)

(72) Inventor: Venigalla B. Rao, Silver Spring, MD (US)

(73) Assignee: The Catholic University of America, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/722,124

(22) Filed: Dec. 20, 2019

(65) Prior Publication Data
US 2020/0147207 A1 May 14, 2020

Related U.S. Application Data

(62) Division of application No. 15/892,772, filed on Feb. 9, 2018, now Pat. No. 10,556,002.

(60) Provisional application No. 62/456,825, filed on Feb. 9, 2017.

(51) Int. Cl.
| | |
|---|---|
| A61K 39/02 | (2006.01) |
| C07K 14/24 | (2006.01) |
| C07K 14/32 | (2006.01) |
| C07K 14/005 | (2006.01) |
| A61K 39/385 | (2006.01) |
| A61K 39/07 | (2006.01) |
| C07K 19/00 | (2006.01) |
| A61K 39/295 | (2006.01) |
| A61K 39/00 | (2006.01) |

(52) U.S. Cl.
CPC ........ *A61K 39/295* (2013.01); *A61K 39/0291* (2013.01); *A61K 39/07* (2013.01); *A61K 39/385* (2013.01); *C07K 14/005* (2013.01); *C07K 14/24* (2013.01); *C07K 14/32* (2013.01); *C07K 19/00* (2013.01); *A61K 2039/5256* (2013.01); *A61K 2039/55505* (2013.01); *A61K 2039/57* (2013.01); *A61K 2039/6075* (2013.01); *A61K 2039/627* (2013.01); *A61K 2039/645* (2013.01); *A61K 2039/70* (2013.01); *C07K 2319/00* (2013.01); *C12N 2795/00034* (2013.01); *C12N 2795/00062* (2013.01); *C12N 2795/10122* (2013.01); *C12N 2795/10134* (2013.01); *Y02A 50/30* (2018.01)

(58) Field of Classification Search
None
See application file for complete search history.

(56) References Cited

U.S. PATENT DOCUMENTS

| 5,683,695 A | 11/1997 | Shen et al. |
| 2015/0017198 A1 | 1/2015 | Rao et al. |

OTHER PUBLICATIONS

DuBois et al. Vaccine. Jun. 11, 2007; 25(24):4747-4754.*
Inglesby, T.V., O'Toole, T. & Henderson, D.A. Preventing the use of biological weapons: improving response should prevention fail. Clin Infect Dis 30, 926-929 (2000).
O'Toole, T. & Inglesby, T.V. Facing the biological weapons threat. Lancet 356, 1128-1129 (2000).
Inglesby, T.V., et al. Plague as a biological weapon: medical and public health management. Working Group on Civilian Biodefense. JAMA 283, 2281-2290 (2000).
Inglesby, T.V., et al. Anthrax as a biological weapon, 2002: updated recommendations for management. JAMA 287, 2236-2252 (2002).
Moayeri, M., Leppla, S.H., Vrentas, C., Pomerantsev, A.P. & Liu, S. Anthrax Pathogenesis. Annu Rev Microbiol 69, 185-208 (2015).
Williamson, E.D. & Dyson, E.H. Anthrax prophylaxis: recent advances and future directions. Frontiers in microbiology 6, 1009 (2015).
M., L., Joellenbeck, Lee L. Zwanziger, Jane S. Durch & Strom, a.B.L. The Anthrax Vaccine: Is It Safe? Does It Work? , (National Academy Press, Washington D.C, 2002).
Leppla, S.H., Robbins, J.B., Schneerson, R. & Shiloach, J. Development of an improved vaccine for anthrax. J Clin Invest 110, 141-144 (2002).
McComb, R.C. & Martchenko, M. Neutralizing antibody and functional mapping of Bacillus anthracis protective antigen—The first step toward a rationally designed anthrax vaccine. Vaccine 34, 13-19 (2016).
Elizabeth J. Valenti, C.o.t.R.C. Summary Basis for Regulatory Action Template. vol. 2015 (2015).
Smiley, S.T. Current challenges in the development of vaccines for pneumonic plague. Expert Rev Vaccines 7, 209-221 (2008).
Zilinskas, R.A. The anti-plague system and the Soviet biological warfare program. Crit Rev Microbiol 32, 47-64 (2006).
Young, J.A. & Collier, R.J. Anthrax toxin: receptor binding, internalization, pore formation, and translocation. Annu Rev Biochem 76, 243-265 (2007).

(Continued)

*Primary Examiner* — Oluwatosin A Ogunbiyi
(74) *Attorney, Agent, or Firm* — Ajay A. Jagtiani; Miles & Stockbridge P.C.

(57) ABSTRACT

Bivalent immunogenic compositions against anthrax and plague are disclosed herein. One bivalent immunogenic composition comprises a triple fusion protein containing three antigens, F1 and V from *Yersinia pestis* and PA antigen from *Bacillus anthracis* fused in-frame and retaining structural and functional integrity of all three antigens. Another bivalent immunogenic composition comprises bacteriophage nanoparticles arrayed with these three antigens on the capsid surface of the bacteriophage nanoparticles. These bivalent immunogenic compositions are able to elicit robust immune response in a subject administered said the bivalent immunogenic compositions and provide protection to the subject against sequential or simultaneous challenge with both anthrax and plague pathogens.

15 Claims, 23 Drawing Sheets
Specification includes a Sequence Listing.

(56) References Cited

OTHER PUBLICATIONS

Kaur, M., Singh, S. & Bhatnagar, R. Anthrax vaccines: present status and future prospects. Expert Rev Vaccines 12, 955-970 (2013).
Wagner, L., et al. Structural and immunological analysis of anthrax recombinant protective antigen adsorbed to aluminum hydroxide adjuvant. Clin Vaccine Immunol 19, 1465-1473 (2012).
D'Souza, A.J., et al. Rapid deamidation of recombinant protective antigen when adsorbed on aluminum hydroxide gel correlates with reduced potency of vaccine. J Pharm Sci 102, 454-461 (2013).
Rosenzweig, J.A., et al. Progress on plague vaccine development. Appl Microbiol Biotechnol 91, 265-286 (2011).
Stenseth, N.C., et al. Plague: past, present, and future. PLoS Med 5, e3 (2008).
Derewenda, U., et al. The structure of Yersinia pestis V-antigen, an essential virulence factor and mediator of immunity against plague. Structure 12, 301-306 (2004).
Williamson, E.D., et al. A new improved sub-unit vaccine for plague: the basis of protection. FEMS Immunol Med Microbiol 12, 223-230 (1995).
Anderson, G.W., Jr., Heath, D.G., Bolt, C.R., Welkos, S.L. & Friedlander, A.M. Short- and long-term efficacy of single-dose subunit vaccines against Yersinia pestis in mice. Am J Trop Med Hyg 58, 793-799 (1998).
Heath, D.G., et al. Protection against experimental bubonic and pneumonic plague by a recombinant capsular F1-V antigen fusion protein vaccine. Vaccine 16, 1131-1137 (1998).
Tao, P., et al. Mutated and bacteriophage T4 nanoparticle arrayed F1-V immunogens from Yersinia pestis as next generation plague vaccines. PLoS Pathog 9, e1003495 (2013).
Williamson, E.D., et al. Human immune response to a plague vaccine comprising recombinant F1 and V antigens. Infect Immun 73, 3598-3608 (2005).
Tao, P., Mahalingam, M. & Rao, V.B. Highly Effective Soluble and Bacteriophage T4 Nanoparticle Plague Vaccines Against Yersinia pestis. Methods Mol Biol 1403, 499-518 (2016).
Tao, P., et al. In vitro and in vivo delivery of genes and proteins using the bacteriophage T4 DNA packaging machine. Proc Natl Acad Sci U S A 110, 5846-5851 (2013).
Tao, P., Li, Q., Shivachandra, S.B. & Rao, V.B. Bacteriophage T4 as a Nanoparticle Platform to Display and Deliver Pathogen Antigens: Construction of an Effective Anthrax Vaccine. Methods Mol Biol 1581(2017).
Fokine, A., et al. Molecular architecture of the prolate head of bacteriophage T4. Proc Natl Acad Sci U S A 101, 6003-6008 (2004).
Qin, L., Fokine, A., O'Donnell, E., Rao, V.B. & Rossmann, M.G. Structure of the small outer capsid protein, Soc: a clamp for stabilizing capsids of T4-like phages. J Mol Biol 395, 728-741 (2010).
Li, Q., Shivachandra, S.B., Zhang, Z. & Rao, V.B. Assembly of the small outer capsid protein, Soc, on bacteriophage T4: a novel system for high density display of multiple large anthrax toxins and foreign proteins on phage capsid. J Mol Biol 370, 1006-1019 (2007).
Shivachandra, S.B., et al. In vitro binding of anthrax protective antigen on bacteriophage T4 capsid surface through Hoc-capsid interactions: a strategy for efficient display of large full-length proteins. Virology 345, 190-198 (2006).
Rao, M., et al. Highly effective generic adjuvant systems for orphan or povertyrelated vaccines. Vaccine 29, 873-877 (2011).
Scobie, H.M., Rainey, G.J., Bradley, K.A. & Young, J.A. Human capillary morphogenesis protein 2 functions as an anthrax toxin receptor. Proc Natl Acad Sci U S A 100, 5170-5174 (2003).
Bradley, K.A., Mogridge, J., Mourez, M., Collier, R.J. & Young, J.A. Identification of the cellular receptor for anthrax toxin. Nature 414, 225-229 (2001).
Klimpel, K.R., Molloy, S.S., Thomas, G. & Leppla, S.H. Anthrax toxin protective antigen is activated by a cell surface protease with the sequence specificity and catalytic properties of furin. Proc Natl Acad Sci U S A 89, 10277-10281 (1992).
Peachman, K.K., et al. Correlation between lethal toxin-neutralizing antibody titers and protection from intranasal challenge with Bacillus anthracis Ames strain spores in mice after transcutaneous immunization with recombinant anthrax protective antigen. Infect Immun 74, 794-797 (2006).
Parent, M.A., et al. Cell-mediated protection against pulmonary Yersinia pestis infection. Infect Immun 73, 7304-7310 (2005).
Ovsyannikova, I.G., et al. Human leukocyte antigens and cellular immune responses to anthrax vaccine adsorbed. Infect Immun 81, 2584-2591 (2013).
Rosenthal, J.A., et al. Mechanistic insight into the TH1-biased immune response to recombinant subunit vaccines delivered by probiotic bacteria-derived outer membrane vesicles. PloS one 9, e112802 (2014).
Albrecht, M.T., et al. Electroporation of a multivalent DNA vaccine cocktail elicits a protective immune response against anthrax and plague. Vaccine 30, 4872-4883 (2012).
Ren, J., et al. Protection against anthrax and plague by a combined vaccine in mice and rabbits. Vaccine 27, 7436-7441 (2009).
Giiffin, K., et al. Protective efficacy of a recombinant plague vaccine when coadministered with another sub-unit or live attenuated vaccine. FEMS Immunol Med Microbiol 43, 425-430 (2005).
Williamson, E.D., et al. Co-immunisation with a plasmid DNA cocktail primes mice against anthrax and plague. Vaccine 20, 2933-2941 (2002).
Sha, J., et al. A non-invasive in vivo imaging system to study dissemination of bioluminescent Yersinia pestis CO92 in a mouse model of pneumonic plague. Microb Pathog 55, 39-50 (2013).
Agar, S.L., et al. Characterization of the rat pneumonic plague model: infectionkinetics following aerosolization of Yersinia pestis CO92. Microbes Infect 11, 205-214 (2009).
Heninger, S., et al. Toxin-deficient mutants of Bacillus anthracis are lethal in a murine model for pulmonary anthrax. Infect Immun 74, 6067-6074 (2006).
Twenhafel, N.A. Pathology of inhalational anthrax animal models. Vet Pathol 47, 819-830 (2010).
Do, Y., et al. Broad T cell immunity to the LcrV virulence protein is induced by targeted delivery to DEC-205/CD205-positive mouse dendritic cells. Eur J Immunol 38, 20-29 (2008).
Sathaliyawala, T., et al. Assembly of human immunodeficiency virus (HIV) antigens on bacteriophage T4: a novel in vitro approach to construct multicomponent HIV vaccines. Journal of virology 80, 7688-7698 (2006).
Peachman, K.K., et al. Anthrax vaccine antigen-adjuvant formulations completely protect New Zealand white rabbits against challenge with Bacillus anthracis Ames strain spores. Clin Vaccine Immunol 19, 11-16 (2012).
Bruttin, A. & Brussow, H. Human volunteers receiving *Escherichia coli* phage T4 orally: a safety test of phage therapy. Antimicrob Agents Chemother 49, 2874- 2878 (2005).
Arora, N. & Leppla, S.H. Fusions of anthrax toxin lethal factor with shiga toxin and diphtheria toxin enzymatic domains are toxic to mammalian cells. Infect Immun 62, 4955-4961 (1994).
Ramirez, D.M., Leppla, S.H., Schneerson, R. & Shiloach, J. Production, recovery and immunogenicity of the protective antigen from a recombinant strain of Bacillus anthracis. J Ind Microbiol Biotechnol 28, 232-238 (2002).
Chen, Z., et al. Potent neutralization of anthrax edema toxin by a humanized monoclonal antibody that competes with calmodulin for edema factor binding. Proc Natl Acad Sci U S A 106, 13487-13492 (2009).
Chaudhury S, Battaile KP, Lovell S, Plano GV, De Guzman RN.Structure of the Yersinia pestis tip protein LcrV refined to 1.65 A resolution. Acta Crystallogr Sect F Struct Biol Cryst Commun(2013) 69(Pt 5):477-81.
Zavialov AV, Tischenko VM, Fooks LJ, Brandsdal BO, Aqvist J, Zav'yalov VP, et al. Resolving the energy paradox of chaperone/ usher-mediated fibre assembly. Biochem J (2005) 389(Pt 3):685-94.

(56) References Cited

OTHER PUBLICATIONS

Tao, P., et al. A Bivalent Anthrax-Plague Vaccine That Can Protect against Two Tier-1 Bioterror Pathogens, Bacillus anthracis and Yersinia pestis. Front Immunol. Jun. 26, 2017;8:687.

* cited by examiner

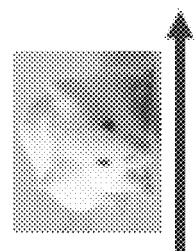
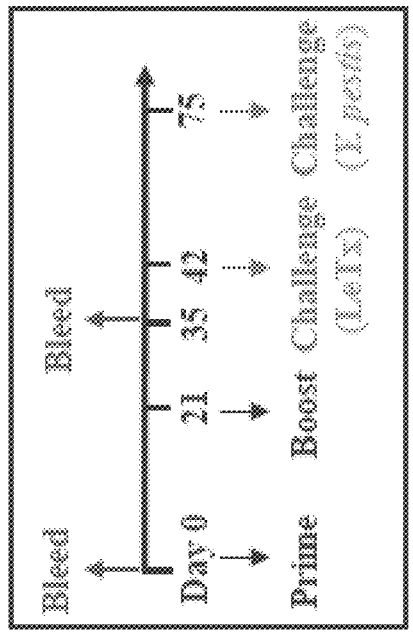
FIG. 4A
FIG. 4B

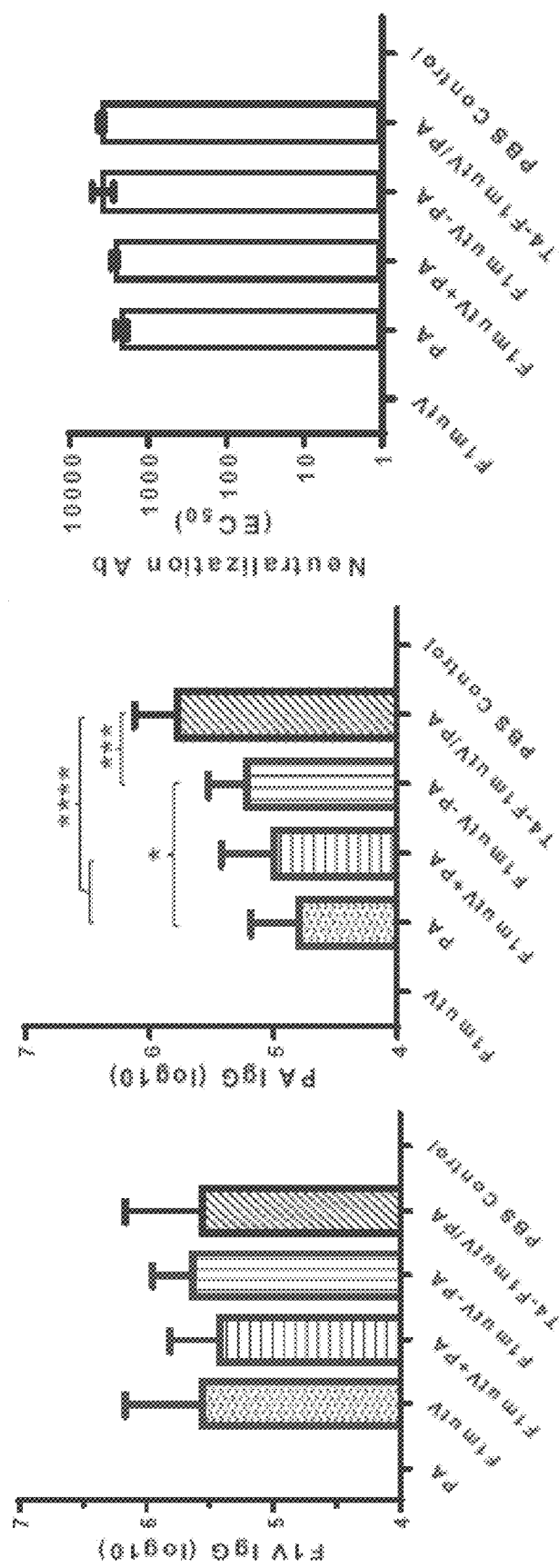

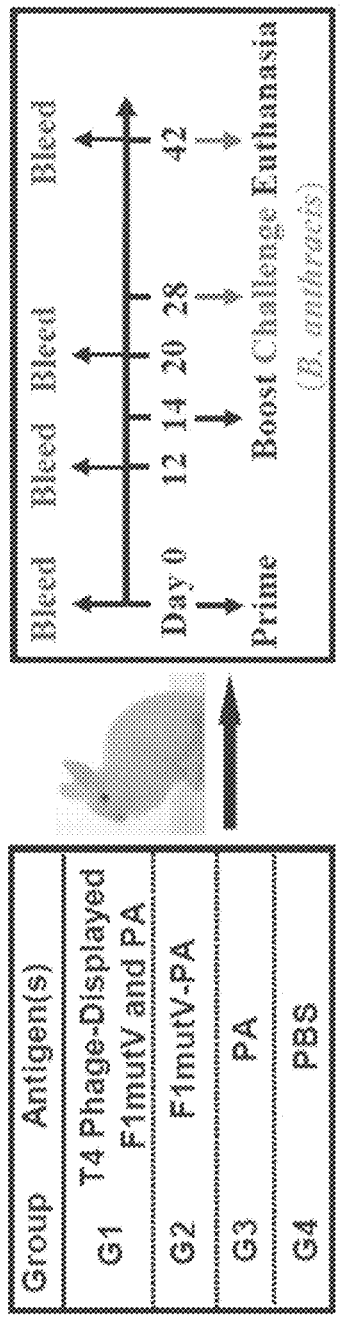
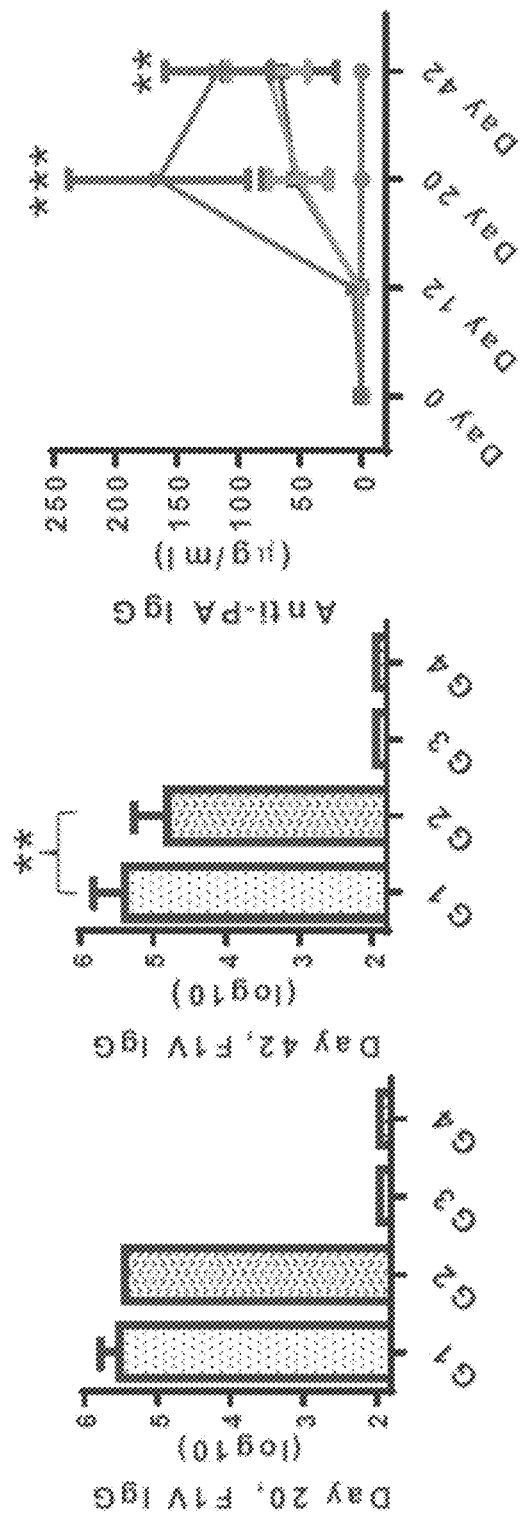
FIG. 9A
FIG. 9B
FIG. 9C
FIG. 9D
FIG. 9E

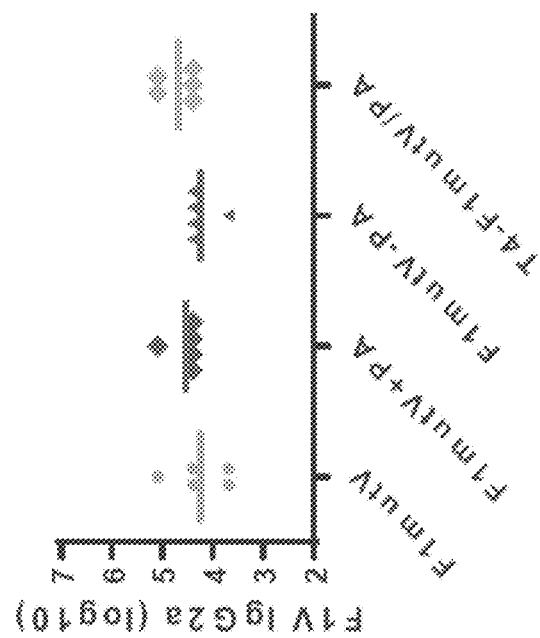
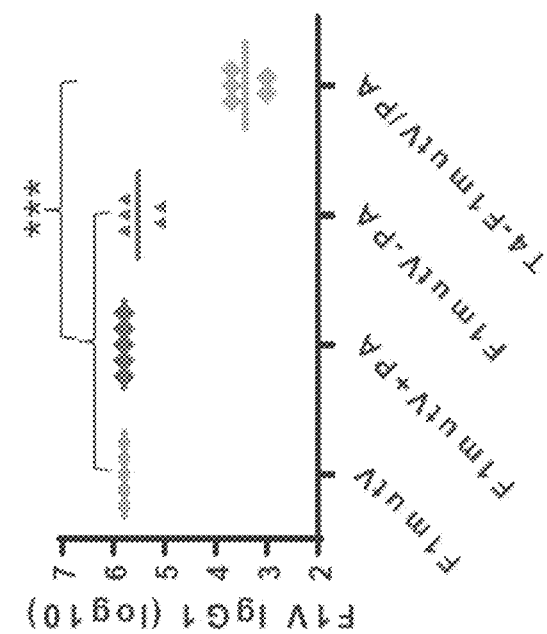
FIG. 13A
FIG. 13B

SEQUENCE LISTING

<160> NUMBER OF SEQ ID NOS: 18

<210> SEQ ID NO 1
<211> LENGTH: 158
<212> TYPE: PRT

<213> ORGANISM: Yersinia pestis

<400> SEQUENCE: 1

Glu Pro Ala Arg Ile Thr Leu Thr Tyr Lys Glu Gly Ala Pro Ile Thr
1               5                   10                  15

Ile Met Asp Asn Gly Asn Ile Asp Thr Glu Leu Leu Val Gly Thr Leu
            20                  25                  30

Thr Leu Gly Gly Tyr Lys Thr Gly Thr Thr Ser Thr Ser Val Asn Phe
        35                  40                  45

Thr Asp Ala Ala Gly Asp Pro Met Tyr Leu Thr Phe Thr Ser Gln Asp
    50                  55                  60

Gly Asn Asn His Gln Phe Thr Thr Lys Val Ile Gly Lys Asp Ser Arg
65                  70                  75                  80

Asp Phe Asp Ile Ser Pro Lys Val Asn Gly Glu Asn Leu Val Gly Asp
                85                  90                  95

Asp Val Val Leu Ala Thr Gly Ser Gln Asp Phe Phe Val Arg Ser Ile
            100                 105                 110

Gly Ser Lys Gly Gly Lys Leu Ala Ala Gly Lys Tyr Thr Asp Ala Val
        115                 120                 125

Thr Val Thr Val Ser Asn Gln Ser Ala Ala Asp Leu Thr Ala Ser Thr
    130                 135                 140

Thr Ala Thr Ala Thr Leu Val Glu Pro Ala Arg Ile Thr Leu
145                 150                 155

<210> SEQ ID NO 2
<211> LENGTH: 326
<212> TYPE: PRT
<213> ORGANISM: Yersinia pestis

<400> SEQUENCE: 2

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys

```
            195                 200                 205
Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
                275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 3
<211> LENGTH: 735
<212> TYPE: PRT
<213> ORGANISM: Bacillus anthracis

<400> SEQUENCE: 3

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
                20                  25                  30

Met Val Val Thr Ser Ser Thr Thr Gly Asp Leu Ser Ile Pro Ser Ser
                35                  40                  45

Glu Leu Glu Asn Ile Pro Ser Glu Asn Gln Tyr Phe Gln Ser Ala Ile
50                  55                  60

Trp Ser Gly Phe Ile Lys Val Lys Lys Ser Asp Glu Tyr Thr Phe Ala
65              70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
                100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
            130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
                180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
210                 215                 220

Lys Trp Ser Thr Ala Ser Asp Pro Tyr Ser Asp Phe Glu Lys Val Thr
225                 230                 235                 240
```

-continued

```
Gly Arg Ile Asp Lys Asn Val Ser Pro Glu Ala Arg His Pro Leu Val
            245                 250                 255
Ala Ala Tyr Pro Ile Val His Val Asp Met Glu Asn Ile Ile Leu Ser
        260                 265                 270
Lys Asn Glu Asp Gln Ser Thr Gln Asn Thr Asp Ser Gln Thr Arg Thr
    275                 280                 285
Ile Ser Lys Asn Thr Ser Thr Ser Arg Thr His Thr Ser Glu Val His
290                 295                 300
Gly Asn Ala Glu Val His Ala Ser Phe Phe Asp Ile Gly Gly Ser Val
305                 310                 315                 320
Ser Ala Gly Phe Ser Asn Ser Asn Ser Ser Thr Val Ala Ile Asp His
                325                 330                 335
Ser Leu Ser Leu Ala Gly Glu Arg Thr Trp Ala Glu Thr Met Gly Leu
            340                 345                 350
Asn Thr Ala Asp Thr Ala Arg Leu Asn Ala Asn Ile Arg Tyr Val Asn
        355                 360                 365
Thr Gly Thr Ala Pro Ile Tyr Asn Val Leu Pro Thr Thr Ser Leu Val
    370                 375                 380
Leu Gly Lys Asn Gln Thr Leu Ala Thr Ile Lys Ala Lys Glu Asn Gln
385                 390                 395                 400
Leu Ser Gln Ile Leu Ala Pro Asn Asn Tyr Tyr Pro Ser Lys Asn Leu
                405                 410                 415
Ala Pro Ile Ala Leu Asn Ala Gln Asp Asp Phe Ser Ser Thr Pro Ile
            420                 425                 430
Thr Met Asn Tyr Asn Gln Phe Leu Glu Leu Glu Lys Thr Lys Gln Leu
        435                 440                 445
Arg Leu Asp Thr Asp Gln Val Tyr Gly Asn Ile Ala Thr Tyr Asn Phe
    450                 455                 460
Glu Asn Gly Arg Val Arg Val Asp Thr Gly Ser Asn Trp Ser Glu Val
465                 470                 475                 480
Leu Pro Gln Ile Gln Glu Thr Thr Ala Arg Ile Ile Phe Asn Gly Lys
                485                 490                 495
Asp Leu Asn Leu Val Glu Arg Arg Ile Ala Ala Val Asn Pro Ser Asp
            500                 505                 510
Pro Leu Glu Thr Thr Lys Pro Asp Met Thr Leu Lys Glu Ala Leu Lys
        515                 520                 525
Ile Ala Phe Gly Phe Asn Glu Pro Asn Gly Asn Leu Gln Tyr Gln Gly
    530                 535                 540
Lys Asp Ile Thr Glu Phe Asp Phe Asn Phe Asp Gln Gln Thr Ser Gln
545                 550                 555                 560
Asn Ile Lys Asn Gln Leu Ala Glu Leu Asn Ala Thr Asn Ile Tyr Thr
                565                 570                 575
Val Leu Asp Lys Ile Lys Leu Asn Ala Lys Met Asn Ile Leu Ile Arg
            580                 585                 590
Asp Lys Arg Phe His Tyr Asp Arg Asn Asn Ile Ala Val Gly Ala Asp
        595                 600                 605
Glu Ser Val Val Lys Glu Ala His Arg Glu Val Ile Asn Ser Ser Thr
    610                 615                 620
Glu Gly Leu Leu Leu Asn Ile Asp Lys Asp Ile Arg Lys Ile Leu Ser
625                 630                 635                 640
Gly Tyr Ile Val Glu Ile Glu Asp Thr Glu Gly Leu Lys Glu Val Ile
                645                 650                 655
Asn Asp Arg Tyr Asp Met Leu Asn Ile Ser Ser Leu Arg Gln Asp Gly
```

```
                        660                 665                 670
Lys Thr Phe Ile Asp Phe Lys Lys Tyr Asn Asp Lys Leu Pro Leu Tyr
                675                 680                 685

Ile Ser Asn Pro Asn Tyr Lys Val Asn Val Tyr Ala Val Thr Lys Glu
            690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 4
<211> LENGTH: 1248
<212> TYPE: PRT
<213> ORGANISM: Artificial Sequence
<220> FEATURE:
<223> OTHER INFORMATION: Description of Artificial Sequence: Synthetic
      amino acid sequence of a fusion protein derived
      from Yersinia pestis and Bacillus anthracis

<400> SEQUENCE: 4

Met Gly Ser Ser His His His His His Ser Ser Gly Leu Val Pro
1               5                   10                  15

Arg Gly Ser His Met Ala Ser Glu Pro Ala Arg Ile Thr Leu Thr Tyr
                20                  25                  30

Lys Glu Gly Ala Pro Ile Thr Ile Met Asp Asn Gly Asn Ile Asp Thr
            35                  40                  45

Glu Leu Leu Val Gly Thr Leu Thr Leu Gly Gly Tyr Lys Thr Gly Thr
50                  55                  60

Thr Ser Thr Ser Val Asn Phe Thr Asp Ala Ala Gly Asp Pro Met Tyr
65                  70                  75                  80

Leu Thr Phe Thr Ser Gln Asp Gly Asn Asn His Gln Phe Thr Thr Lys
                85                  90                  95

Val Ile Gly Lys Asp Ser Arg Asp Phe Asp Ile Ser Pro Lys Val Asn
                100                 105                 110

Gly Glu Asn Leu Val Gly Asp Asp Val Val Leu Ala Thr Gly Ser Gln
            115                 120                 125

Asp Phe Phe Val Arg Ser Ile Gly Ser Lys Gly Gly Lys Leu Ala Ala
    130                 135                 140

Gly Lys Tyr Thr Asp Ala Val Thr Val Thr Val Ser Asn Gln Ser Ala
145                 150                 155                 160

Ala Asp Leu Thr Ala Ser Thr Thr Ala Thr Ala Thr Leu Val Glu Pro
                165                 170                 175

Ala Arg Ile Thr Leu Gly Ser Met Ile Arg Ala Tyr Glu Gln Asn Pro
            180                 185                 190

Gln His Phe Ile Glu Asp Leu Glu Lys Val Arg Val Glu Gln Leu Thr
    195                 200                 205

Gly His Gly Ser Ser Val Leu Glu Glu Leu Val Gln Leu Val Lys Asp
210                 215                 220

Lys Asn Ile Asp Ile Ser Ile Lys Tyr Asp Pro Arg Lys Asp Ser Glu
225                 230                 235                 240

Val Phe Ala Asn Arg Val Ile Thr Asp Ile Glu Leu Leu Lys Lys
                245                 250                 255

Ile Leu Ala Tyr Phe Leu Pro Glu Asp Ala Ile Leu Lys Gly Gly His
            260                 265                 270

Tyr Asp Asn Gln Leu Gln Asn Gly Ile Lys Arg Val Lys Glu Phe Leu
    275                 280                 285
```

```
Glu Ser Ser Pro Asn Thr Gln Trp Glu Leu Arg Ala Phe Met Ala Val
    290                 295                 300

Met His Phe Ser Leu Thr Ala Asp Arg Ile Asp Asp Ile Leu Lys
305                 310                 315                 320

Val Ile Val Asp Ser Met Asn His His Gly Asp Ala Arg Ser Lys Leu
                325                 330                 335

Arg Glu Glu Leu Ala Glu Leu Thr Ala Glu Leu Lys Ile Tyr Ser Val
            340                 345                 350

Ile Gln Ala Glu Ile Asn Lys His Leu Ser Ser Gly Thr Ile Asn
        355                 360                 365

Ile His Asp Lys Ser Ile Asn Leu Met Asp Lys Asn Leu Tyr Gly Tyr
    370                 375                 380

Thr Asp Glu Glu Ile Phe Lys Ala Ser Ala Glu Tyr Lys Ile Leu Glu
385                 390                 395                 400

Lys Met Pro Gln Thr Thr Ile Gln Val Asp Gly Ser Glu Lys Lys Ile
                405                 410                 415

Val Ser Ile Lys Asp Phe Leu Gly Ser Glu Asn Lys Arg Thr Gly Ala
            420                 425                 430

Leu Gly Asn Leu Lys Asn Ser Tyr Ser Tyr Asn Lys Asp Asn Asn Glu
        435                 440                 445

Leu Ser His Phe Ala Thr Thr Cys Ser Asp Lys Ser Arg Pro Leu Asn
    450                 455                 460

Asp Leu Val Ser Gln Lys Thr Thr Gln Leu Ser Asp Ile Thr Ser Arg
465                 470                 475                 480

Phe Asn Ser Ala Ile Glu Ala Leu Asn Arg Phe Ile Gln Lys Tyr Asp
                485                 490                 495

Ser Val Met Gln Arg Leu Leu Asp Asp Thr Ser Gly Lys Glu Ala Ser
            500                 505                 510

Ala Glu Val Lys Gln Glu Asn Arg Leu Leu Asn Glu Ser Glu Ser Ser
        515                 520                 525

Ser Gln Gly Leu Leu Gly Tyr Tyr Phe Ser Asp Leu Asn Phe Gln Ala
    530                 535                 540

Pro Met Val Val Thr Ser Ser Thr Thr Gly Asp Leu Ser Ile Pro Ser
545                 550                 555                 560

Ser Glu Leu Glu Asn Ile Pro Ser Glu Asn Gln Tyr Phe Gln Ser Ala
                565                 570                 575

Ile Trp Ser Gly Phe Ile Lys Val Lys Lys Ser Asp Glu Tyr Thr Phe
            580                 585                 590

Ala Thr Ser Ala Asp Asn His Val Thr Met Trp Val Asp Asp Gln Glu
        595                 600                 605

Val Ile Asn Lys Ala Ser Asn Ser Asn Lys Ile Arg Leu Glu Lys Gly
    610                 615                 620

Arg Leu Tyr Gln Ile Lys Ile Gln Tyr Gln Arg Glu Asn Pro Thr Glu
625                 630                 635                 640

Lys Gly Leu Asp Phe Lys Leu Tyr Trp Thr Asp Ser Gln Asn Lys Lys
                645                 650                 655

Glu Val Ile Ser Ser Asp Asn Leu Gln Leu Pro Glu Leu Lys Gln Lys
            660                 665                 670

Ser Ser Asn Ser Arg Lys Lys Arg Ser Thr Ser Ala Gly Pro Thr Val
        675                 680                 685

Pro Asp Arg Asp Asn Asp Gly Ile Pro Asp Ser Leu Glu Val Glu Gly
    690                 695                 700
```

```
Tyr Thr Val Asp Val Lys Asn Lys Arg Thr Phe Leu Ser Pro Trp Ile
705                 710                 715                 720

Ser Asn Ile His Glu Lys Lys Gly Leu Thr Lys Tyr Lys Ser Ser Pro
            725                 730                 735

Glu Lys Trp Ser Thr Ala Ser Asp Pro Tyr Ser Asp Phe Glu Lys Val
        740                 745                 750

Thr Gly Arg Ile Asp Lys Asn Val Ser Pro Glu Ala Arg His Pro Leu
    755                 760                 765

Val Ala Ala Tyr Pro Ile Val His Val Asp Met Glu Asn Ile Ile Leu
770                 775                 780

Ser Lys Asn Glu Asp Gln Ser Thr Gln Asn Thr Asp Ser Gln Thr Arg
785                 790                 795                 800

Thr Ile Ser Lys Asn Thr Ser Thr Ser Arg Thr His Thr Ser Glu Val
            805                 810                 815

His Gly Asn Ala Glu Val His Ala Ser Phe Phe Asp Ile Gly Gly Ser
            820                 825                 830

Val Ser Ala Gly Phe Ser Asn Ser Asn Ser Ser Thr Val Ala Ile Asp
            835                 840                 845

His Ser Leu Ser Leu Ala Gly Glu Arg Thr Trp Ala Glu Thr Met Gly
850                 855                 860

Leu Asn Thr Ala Asp Thr Ala Arg Leu Asn Ala Asn Ile Arg Tyr Val
865                 870                 875                 880

Asn Thr Gly Thr Ala Pro Ile Tyr Asn Val Leu Pro Thr Thr Ser Leu
                885                 890                 895

Val Leu Gly Lys Asn Gln Thr Leu Ala Thr Ile Lys Ala Lys Glu Asn
            900                 905                 910

Gln Leu Ser Gln Ile Leu Ala Pro Asn Asn Tyr Tyr Pro Ser Lys Asn
            915                 920                 925

Leu Ala Pro Ile Ala Leu Asn Ala Gln Asp Asp Phe Ser Ser Thr Pro
            930                 935                 940

Ile Thr Met Asn Tyr Asn Gln Phe Leu Glu Leu Glu Lys Thr Lys Gln
945                 950                 955                 960

Leu Arg Leu Asp Thr Asp Gln Val Tyr Gly Asn Ile Ala Thr Tyr Asn
                965                 970                 975

Phe Glu Asn Gly Arg Val Arg Val Asp Thr Gly Ser Asn Trp Ser Glu
            980                 985                 990

Val Leu Pro Gln Ile Gln Glu Thr Thr Ala Arg Ile Ile Phe Asn Gly
            995                 1000                1005

Lys Asp Leu Asn Leu Val Glu Arg Arg Ile Ala Ala Val Asn Pro
    1010                1015                1020

Ser Asp Pro Leu Glu Thr Thr Lys Pro Asp Met Thr Leu Lys Glu
    1025                1030                1035

Ala Leu Lys Ile Ala Phe Gly Phe Asn Glu Pro Asn Gly Asn Leu
    1040                1045                1050

Gln Tyr Gln Gly Lys Asp Ile Thr Glu Phe Asp Phe Asn Phe Asp
    1055                1060                1065

Gln Gln Thr Ser Gln Asn Ile Lys Asn Gln Leu Ala Glu Leu Asn
    1070                1075                1080

Ala Thr Asn Ile Tyr Thr Val Leu Asp Lys Ile Lys Leu Asn Ala
    1085                1090                1095

Lys Met Asn Ile Leu Ile Arg Asp Lys Arg Phe His Tyr Asp Arg
    1100                1105                1110

Asn Asn Ile Ala Val Gly Ala Asp Glu Ser Val Val Lys Glu Ala
```

```
                1115                1120                1125
His Arg Glu Val Ile Asn Ser Ser Thr Glu Gly Leu Leu Leu Asn
        1130                1135                1140
Ile Asp Lys Asp Ile Arg Lys Ile Leu Ser Gly Tyr Ile Val Glu
        1145                1150                1155
Ile Glu Asp Thr Glu Gly Leu Lys Glu Val Ile Asn Asp Arg Tyr
        1160                1165                1170
Asp Met Leu Asn Ile Ser Ser Leu Arg Gln Asp Gly Lys Thr Phe
        1175                1180                1185
Ile Asp Phe Lys Lys Tyr Asn Asp Lys Leu Pro Leu Tyr Ile Ser
        1190                1195                1200
Asn Pro Asn Tyr Lys Val Asn Val Tyr Ala Val Thr Lys Glu Asn
        1205                1210                1215
Thr Ile Ile Asn Pro Ser Glu Asn Gly Asp Thr Ser Thr Asn Gly
        1220                1225                1230
Ile Lys Lys Ile Leu Ile Phe Ser Lys Lys Gly Tyr Glu Ile Gly
        1235                1240                1245

<210> SEQ ID NO 5
<211> LENGTH: 1452
<212> TYPE: DNA
<213> ORGANISM: Artificial Sequence
<220> FEATURE:
<223> OTHER INFORMATION: Description of Artificial Sequence: Synthetic
      nucleotide sequence for fusion protein derived
      from Yersinia pestis

<400> SEQUENCE: 5
gaaccagccc gcatcactct tacatataag gaaggcgctc aattacaat tatggacaat      60
ggaaacatcg atacagaatt acttgttggt acgcttactc ttggcggcta taaaacagga     120
accactagca catctgttaa ctttacagat gccgcgggtg atcccatgta cttaacattt     180
acttctcagg atggaaataa ccaccaattc actacaaaag tgattggcaa ggattctaga     240
gattttgata tctctcctaa ggtaaacggt gagaaccttg tgggggatga cgtcgtcttg     300
gctacgggca gccaggattt cttgttcgc tcaattggtt ccaaaggcgg taaacttgca     360
gcaggtaaat acactgatgc tgtaaccgta accgtatcta accaatctgc agcagattta     420
actgcaagca ccactgcaac ggcaactctt gttgaaccag cccgcatcgg atccatgatt     480
agagcctacg aacaaaaccc acaacatttt attgaggatc tagaaaagt tagggtggaa     540
caacttactg tcatggttc ttcagtttta gaagaattgg ttcagttagt caaagataaa     600
aatatagata tttccattaa atatgatccc agaaaagatt cggaggtttt tgccaataga     660
gtaattactg atgatatcga attgctcaag aaaatcctag cttatttct acccgaggat     720
gccattctta aggcggtca ttatgacaac caactgcaaa atggcatcaa gcgagtaaaa     780
gagttccttg aatcatcgcc gaatacacaa tgggaattgc gggcgttcat ggcagtaatg     840
catttctctt taaccgccga tcgtatcgat gatgatattt tgaaagtgat tgttgattca     900
atgaatcatc atggtgatgc ccgtagcaag ttgcgtgaag aattagctga gcttaccgcc     960
gaattaaaga tttattcagt tattcaagcc gaaattaata gcatctgtc tagtagtggc    1020
accataaata tccatgataa atccattaat ctcatggata aaaatttata tggttataca    1080
gatgaagaga ttttttaaagc cagcgcagag tacaaaattc tcgagaaaat gcctcaaacc    1140
accattcagg tggatgggag cgagaaaaaa atagtctcga taaaggactt tcttggaagt    1200
gagaataaaa gaaccggggc gttgggtaat ctgaaaaact catactctta ataaagat     1260
```

```
aataatgaat tatctcactt tgccaccacc tgctcggata agtccaggcc gctcaacgac    1320
ttggttagcc aaaaaacaac tcagctgtct gatattacat cacgttttaa ttcagctatt    1380
gaagcactga accgtttcat tcagaaatat gattcagtga tgcaacgtct gctagatgac    1440
acgtctggta aa                                                        1452

<210> SEQ ID NO 6
<211> LENGTH: 2208
<212> TYPE: DNA
<213> ORGANISM: Bacillus anthracis

<400> SEQUENCE: 6
gaagttaaac aggagaaccg gttattaaat gaatcagaat caagttccca ggggttacta      60
ggatactatt ttagtgattt gaattttcaa gcacccatgg tggttacttc ttctactaca    120
ggggatttat ctattcctag ttctgagtta gaaaatattc catcggaaaa ccaatatttt    180
caatctgcta tttggtcagg atttatcaaa gttaagaaga gtgatgaata tacatttgct    240
acttccgctg ataatcatgt aacaatgtgg gtagatgacc aagaagtgat taataaagcc    300
tctaattcta acaaaatcag attagaaaaa ggaagattat atcaaataaa aattcaatat    360
caacgagaaa atcctactga aaaggattg gatttcaagt tgtactggac cgattctcaa    420
aataaaaaag aagtgatttc tagtgataac ttacaattgc cagaattaaa acaaaaatct    480
tcgaactcaa gaaaaagcg aagtacaagt gctggaccta cggttccaga ccgtgacaat    540
gatggaatcc ctgattcatt agaggtagaa ggatatacgg ttgatgtcaa aaataaaaga    600
acttttcttt caccatggat ttctaatatt catgaaaaga aggattaac caaatataaa    660 tcatctcctg aaaatggag cacggcttct gatccgtaca gtgatttcga aaaggttaca    720
ggacggattg ataagaatgt atcaccagag gcaagacacc cccttgtggc agcttatccg    780
attgtacatg tagatatgga gaatattatt ctctcaaaaa atgaggatca atccacacag    840
aatactgata gtcaaacgag aacaataagt aaaaatactt ctacaagtag gacacatact    900
agtgaagtac atgaaatgc agaagtgcat gcgtcgttct ttgatattgg tgggagtgta    960
tctgcaggat ttagtaattc gaattcaagt acggtcgcaa ttgatcattc actatctcta    1020 gcagggaaa gaacttgggc tgaaacaatg ggtttaaata ccgctgatac agcaagatta    1080
aatgccaata ttagatatgt aaatactggg acggctccaa tctacaacgt gttaccaacg    1140
acttcgttag tgttaggaaa aaatcaaaca ctcgcgacaa ttaaagctaa ggaaaaccaa    1200
ttaagtcaaa tacttgcacc taataattat tatccttcta aaaacttggc gccaatcgca    1260
ttaaatgcac aagacgattt cagttctact ccaattacaa tgaattacaa tcaatttctt    1320
gagttagaaa aaacgaaaca attaagatta gatacggatc aagtatatgg aaatatagca    1380
acatacaatt tgaaaatgg aagagtgagg gtggatacag gctcgaactg gagtgaagtg    1440
ttaccgcaaa ttcaagaaac aactgcacgt atcatttta atggaaaaga tttaaatctg    1500
gtagaaaggc ggatagcggc ggttaatcct agtgatccat agaaacgac taaaccggat    1560 atgacattaa agaagccct taaaatagca tttggattta acgaaccgaa tggaaactta    1620
caatatcaag ggaagacat aaccgaattt gattttaatt tcgatcaaca acatctcaa    1680 aatatcaaga atcagttagc ggaattaaac gcaactaaca tatatactgt attagataaa    1740
atcaaattaa atgcaaaaat gaatatttta ataagagata aacgttttca ttatgataga    1800
aataacatag cagttggggc ggatgagtca gtagttaagg aggctcatag agaagtaatt    1860
```

-continued

```
aattcgtcaa cagagggatt attgttaaat attgataagg atataagaaa aatattatca    1920
ggttatattg tagaaattga agatactgaa gggcttaaag aagttataaa tgacagatat    1980
gatatgttga atatttctag tttacggcaa gatggaaaaa catttataga ttttaaaaaa    2040
tataatgata aattaccgtt atatataagt aatcccaatt ataaggtaaa tgtatatgct    2100
gttactaaag aaaacactat tattaatcct agtgagaatg gggatactag taccaacggg    2160
atcaagaaaa ttttaatctt ttctaaaaaa ggctatgaga taggataa                2208
```

<210> SEQ ID NO 7
<211> LENGTH: 4
<212> TYPE: PRT
<213> ORGANISM: Bacillus anthracis

<400> SEQUENCE: 7

Arg Lys Lys Arg
1

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
acccaagctt ctgctgaagt taaacaggag aaccggttat t                        41
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
gtgattaata aagcctctaa ttctaacaaa                                      30
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
tttgttagaa ttagaggctt tattaatcac                                      30
```

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
gccctcgagt tatcctatct catagccttt tttag                                35
```

<210> SEQ ID NO 12
<211> LENGTH: 4
<212> TYPE: PRT

<213> ORGANISM: Artificial Sequence
<220> FEATURE:
<223> OTHER INFORMATION: Description of Artificial Sequence: Synthetic peptide

<400> SEQUENCE: 12

Glu Ala Ser Ala
1

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
gcatccgcta gcggtggtta tgtaaacatc aaa                33

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
cagaagcttc accacttact ggtgtagggg taaac              35

<210> SEQ ID NO 15
<211> LENGTH: 231
<212> TYPE: DNA
<213> ORGANISM: Bacteriophage RB69

<400> SEQUENCE: 15
ggtggttatg taaacatcaa aacctttacg catcctgctg gtgaaggtaa agaagttaaa    60
ggtatggaag tttctgtacc gtttgagatt tattcaaacg aacatcggat tgctgatgct   120
cattatcaga ctttcccatc tgaaaaagct gcttacacta ctgtggtgac tgacgcagca   180
gattggcgta ctaagaacgc tgcaatgttt accoctacac cagtaagtgg t            231

<210> SEQ ID NO 16
<211> LENGTH: 77
<212> TYPE: PRT
<213> ORGANISM: Bacteriophage RB49

<400> SEQUENCE: 16

Gly Gly Tyr Val Asn Ile Lys Thr Phe Thr His Pro Ala Gly Glu Gly
1               5                   10                  15

Lys Glu Val Lys Gly Met Glu Val Ser Val Pro Phe Glu Ile Tyr Ser
                20                  25                  30

Asn Glu His Arg Ile Ala Asp Ala His Tyr Gln Thr Phe Pro Ser Glu
            35                  40                  45

Lys Ala Ala Tyr Thr Thr Val Val Thr Asp Ala Ala Asp Trp Arg Thr
        50                  55                  60

Lys Asn Ala Ala Met Phe Thr Pro Thr Pro Val Ser Gly
65                  70                  75

<210> SEQ ID NO 17
<211> LENGTH: 3990
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 17

```
atgggcagca gccatcatca tcatcatcac agcagcggcc tggtgccgcg cggcagccat      60
atggctagcg aaccagcccg catcactctt acatataagg aaggcgctcc aattacaatt     120
atggacaatg gaaacatcga tacagaatta cttgttggta cgcttactct tggcggctat     180
aaaacaggaa ccactagcac atctgttaac tttacagatg ccgcgggtga tcccatgtac     240
ttaacattta cttctcagga tggaaataac caccaattca ctacaaaagt gattggcaag     300
gattctagag attttgatat ctctcctaag gtaaacggtg agaaccttgt ggggatgac      360
gtcgtcttgg ctacgggcag ccaggatttc tttgttcgct caattggttc caaaggcggt     420
aaacttgcag caggtaaata cactgatgct gtaaccgtaa ccgtatctaa ccaatctgca     480
gcagatttaa ctgcaagcac cactgcaacg gcaactcttg ttgaaccagc ccgcatcact     540
ggatccatga ttagagccta cgaacaaaac ccacaacatt ttattgagga tctagaaaaa     600
gttagggtgg aacaacttac tggtcatggt tcttcagttt tagaagaatt ggttcagtta     660
gtcaaagata aaaatataga tatttccatt aaatatgatc ccagaaaaga ttcggaggtt     720
tttgccaata gagtaattac tgatgatatc gaattgctca agaaaatcct agcttatttt     780
ctacccgagg atgccattct taaaggcggt cattatgaca ccaactgca aaatggcatc     840
aagcgagtaa aagagttcct tgaatcatcg ccgaatacac aatgggaatt gcgggcgttc     900
atggcagtaa tgcatttctc tttaaccgcc gatcgtatcg atgatgatat tttgaaagtg     960
attgttgatt caatgaatca tcatggtgat gcccgtagca agttgcgtga agaattagct    1020
gagcttaccg ccgaattaaa gatttattca gttattcaag ccgaaattaa taagcatctg    1080
tctagtagtg gcaccataaa tatccatgat aaatccatta atctcatgga taaaaattta    1140
tatggttata cagatgaaga gatttttaaa gccagcgcag agtacaaaat tctcgagaaa    1200
atgcctcaaa ccaccattca ggtggatggg agcgagaaaa aaatagtctc gataaaggac    1260
tttcttggaa gtgagaataa agaaccgggg cgttgggta atctgaaaaa ctcatactct    1320
tataataaag ataataatga attatctcac tttgccacca cctgctcgga taagtccagg    1380
ccgctcaacg acttggttag ccaaaaaaca actcagctgt ctgatattac atcacgtttt    1440
aattcagcta ttgaagcact gaaccgtttc attcagaaat atgattcagt gatgcaacgt    1500
ctgctagatg acacgtctgg taagaagct tctgctggtg gttatgtaaa catcaaaacc    1560
tttacgcatc ctgctggtga aggtaaagaa gttaaaggta tggaagtttc tgtaccgttt    1620
gagatttatt caaacgaaca tcggattgct gatgctcatt atcagacttt ccatctgaa    1680
aaagctgctt acactactgt ggtgactgac gcagcagatt ggcgtactaa gaacgctgca    1740
atgttaccc ctacaccagt aagtggtctc gaggccagcg cggaagttaa acaggagaac     1800
cggttattaa atgaatcaga atcaagttcc caggggttac taggatacta ttttagtgat    1860
ttgaattttc aagcacccat ggtggttacc tcttctacta caggggattt atctattcct    1920
agttctgagt tagaaaatat tccatcggaa accaatatat ttcaatctgc tatttggtca    1980
ggatttatca agttaagaa gagtgatgaa tatacatttg ctacttccgc tgataatcat    2040
gtaacaatgt gggtagatga ccaagaagtg attaataaag cttctaattc taacaaaatc    2100
agattagaaa aaggaagatt atatcaaata aaaattcaat atcaacgaga aatcctact     2160
```

```
gaaaaaggat tggatttcaa gttgtactgg accgattctc aaaataaaaa agaagtgatt    2220
tctagtgata acttacaatt gccagaatta aacaaaaat cttcgaactc aagaaaaaag    2280
cgaagtacaa gtgctggacc tacggttcca gaccgtgaca atgatggaat ccctgattca    2340
ttagaggtag aaggatatac ggttgatgtc aaaaataaaa gaacttttct ttcaccatgg    2400
atttctaata ttcatgaaaa gaaggatta accaaatata aatcatctcc tgaaaatgg     2460 agcacggctt ctgatccgta tagtgatttc gaaaaggtta caggacggat tgataagaat    2520
gtatcaccag aggcaagaca cccccttgtg gcagcttatc cgattgtaca tgtagatatg    2580
gagaatatta ttctctcaaa aaatgaggat caatccacac agaatactga tagtcaaacg    2640
agaacaataa gtaaaaatac ttctacaagt aggacacata ctagtgaagt acatggaaat    2700
gcagaagtgc atgcgtcgtt ctttgatatt ggtgggagtg tatctgcagg atttagtaat    2760
tcgaattcaa gtacggtcgc aattgatcat tcactatctc tagcagggga agaacttgg     2820 gctgaaacaa tgggttaa taccgctgat acagcaagat aaatgccaa tattagatat      2880 gtaaatactg gacggctcc aatctacaac gtgttaccaa cgacttcgtt agtgttagga    2940
aaaaatcaaa cactcgcgac aattaaagct aaggaaaacc aattaagtca aatacttgca    3000
cctaataatt attatccttc taaaaacttg gcgccaatcg cattaaatgc acaagacgat    3060
ttcagttcta ctccaattac aatgaattac aatcaatttc ttgagttaga aaaaacgaaa    3120
caattaagat tagatacgga tcaagtatat gggaatatag caacatacaa ttttgaaaat    3180
ggaagagtga gggtggatac aggctcgaac tggagtgaag tgttaccgca aattcaagaa    3240
acaactgcac gtatcatttt taatggaaaa gatttaaatc tggtagaaag gcggatagcg    3300
gcggttaatc ctagtgatcc attagaaacg actaaaccgg atatgacatt aaaagaagcc    3360
cttaaaatag catttggatt taacgaaccg aatggaaact acaatatca agggaaagac    3420 ataaccgaat ttgatttta tttcgatcaa caaacatctc aaaatatcaa gaatcagtta    3480
gcggaattaa acgcaactaa catatatact gtattagata aatcaaatt aaatgcaaaa    3540 atgaatattt taataagaga taaacgttttc cattatgata gaaataacat agcagttggg    3600
gcggatgagt cagtagttaa ggaggctcat agagaagtaa ttaattcgtc aacgagggga    3660
ttattgttaa atattgataa ggatataaga aaaatattat caggttatat tgtagaaatt    3720
gaagatactg aagggcttaa agaagttata atgacagat atgatatgtt gaatatttct    3780
agtttacggc aagatggaaa aacatttata gatttttaaa aatataatga taaattaccg    3840
ttatatataa gtaatcccaa ttataaggta aatgtatatg ctgttactaa agaaaacact    3900
attattaatc ctagtgagaa tggggatact agtaccaacg ggatcaagaa aattttaatc    3960
ttttctaaaa aaggctatga gataggataa                                    3990
```

<210> SEQ ID NO 18
<211> LENGTH: 1329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Ser Ser His His His His His His Ser Ser Gly Leu Val Pro
1               5                   10                  15

Arg Gly Ser His Met Ala Ser Glu Pro Ala Arg Ile Thr Leu Thr Tyr
            20                  25                  30

```
Lys Glu Gly Ala Pro Ile Thr Ile Met Asp Asn Gly Asn Ile Asp Thr
         35                  40                  45

Glu Leu Leu Val Gly Thr Leu Thr Leu Gly Gly Tyr Lys Thr Gly Thr
 50                  55                  60

Thr Ser Thr Ser Val Asn Phe Thr Asp Ala Ala Gly Asp Pro Met Tyr
 65                  70                  75                  80

Leu Thr Phe Thr Ser Gln Asp Gly Asn Asn His Gln Phe Thr Thr Lys
                 85                  90                  95

Val Ile Gly Lys Asp Ser Arg Asp Phe Asp Ile Ser Pro Lys Val Asn
            100                 105                 110

Gly Glu Asn Leu Val Gly Asp Val Val Leu Ala Thr Gly Ser Gln
        115                 120                 125

Asp Phe Phe Val Arg Ser Ile Gly Ser Lys Gly Gly Lys Leu Ala Ala
    130                 135                 140

Gly Lys Tyr Thr Asp Ala Val Thr Val Thr Val Ser Asn Gln Ser Ala
145                 150                 155                 160

Ala Asp Leu Thr Ala Ser Thr Thr Ala Thr Ala Thr Leu Val Glu Pro
                165                 170                 175

Ala Arg Ile Thr Gly Ser Met Ile Arg Ala Tyr Glu Gln Asn Pro Gln
            180                 185                 190

His Phe Ile Glu Asp Leu Glu Lys Val Arg Val Glu Gln Leu Thr Gly
    195                 200                 205

His Gly Ser Ser Val Leu Glu Glu Leu Val Gln Leu Val Lys Asp Lys
    210                 215                 220

Asn Ile Asp Ile Ser Ile Lys Tyr Asp Pro Arg Lys Asp Ser Glu Val
225                 230                 235                 240

Phe Ala Asn Arg Val Ile Thr Asp Asp Ile Glu Leu Leu Lys Lys Ile
            245                 250                 255

Leu Ala Tyr Phe Leu Pro Glu Asp Ala Ile Leu Lys Gly Gly His Tyr
                260                 265                 270

Asp Asn Gln Leu Gln Asn Gly Ile Lys Arg Val Lys Glu Phe Leu Glu
    275                 280                 285

Ser Ser Pro Asn Thr Gln Trp Glu Leu Arg Ala Phe Met Ala Val Met
    290                 295                 300

His Phe Ser Leu Thr Ala Asp Arg Ile Asp Asp Ile Leu Lys Val
305                 310                 315                 320

Ile Val Asp Ser Met Asn His His Gly Asp Ala Arg Ser Lys Leu Arg
            325                 330                 335

Glu Glu Leu Ala Glu Leu Thr Ala Glu Leu Lys Ile Tyr Ser Val Ile
        340                 345                 350

Gln Ala Glu Ile Asn Lys His Leu Ser Ser Ser Gly Thr Ile Asn Ile
    355                 360                 365

His Asp Lys Ser Ile Asn Leu Met Asp Lys Asn Leu Tyr Gly Tyr Thr
    370                 375                 380

Asp Glu Glu Ile Phe Lys Ala Ser Ala Glu Tyr Lys Ile Leu Glu Lys
385                 390                 395                 400

Met Pro Gln Thr Thr Ile Gln Val Asp Gly Ser Glu Lys Lys Ile Val
            405                 410                 415

Ser Ile Lys Asp Phe Leu Gly Ser Glu Asn Lys Arg Thr Gly Ala Leu
            420                 425                 430

Gly Asn Leu Lys Asn Ser Tyr Ser Tyr Asn Lys Asp Asn Asn Glu Leu
        435                 440                 445

Ser His Phe Ala Thr Thr Cys Ser Asp Lys Ser Arg Pro Leu Asn Asp
```

```
                450            455            460
Leu Val Ser Gln Lys Thr Thr Gln Leu Ser Asp Ile Thr Ser Arg Phe
465                 470                 475                 480

Asn Ser Ala Ile Glu Ala Leu Asn Arg Phe Ile Gln Lys Tyr Asp Ser
                485                 490                 495

Val Met Gln Arg Leu Leu Asp Asp Thr Ser Gly Lys Glu Ala Ser Ala
                500                 505                 510

Gly Gly Tyr Val Asn Ile Lys Thr Phe Thr His Pro Ala Gly Glu Gly
                515                 520                 525

Lys Glu Val Lys Gly Met Glu Val Ser Val Pro Phe Glu Ile Tyr Ser
                530                 535                 540

Asn Glu His Arg Ile Ala Asp Ala His Tyr Gln Thr Phe Pro Ser Glu
545                 550                 555                 560

Lys Ala Ala Tyr Thr Thr Val Val Thr Asp Ala Ala Asp Trp Arg Thr
                565                 570                 575

Lys Asn Ala Ala Met Phe Thr Pro Thr Pro Val Ser Gly Leu Glu Ala
                580                 585                 590

Ser Ala Glu Val Lys Gln Glu Asn Arg Leu Leu Asn Glu Ser Glu Ser
                595                 600                 605

Ser Ser Gln Gly Leu Leu Gly Tyr Tyr Phe Ser Asp Leu Asn Phe Gln
                610                 615                 620

Ala Pro Met Val Val Thr Ser Ser Thr Thr Gly Asp Leu Ser Ile Pro
625                 630                 635                 640

Ser Ser Glu Leu Glu Asn Ile Pro Ser Glu Asn Gln Tyr Phe Gln Ser
                645                 650                 655

Ala Ile Trp Ser Gly Phe Ile Lys Val Lys Lys Ser Asp Glu Tyr Thr
                660                 665                 670

Phe Ala Thr Ser Ala Asp Asn His Val Thr Met Trp Val Asp Asp Gln
                675                 680                 685

Glu Val Ile Asn Lys Ala Ser Asn Ser Asn Lys Ile Arg Leu Glu Lys
                690                 695                 700

Gly Arg Leu Tyr Gln Ile Lys Ile Gln Tyr Gln Arg Glu Asn Pro Thr
705                 710                 715                 720

Glu Lys Gly Leu Asp Phe Lys Leu Tyr Trp Thr Asp Ser Gln Asn Lys
                725                 730                 735

Lys Glu Val Ile Ser Ser Asp Asn Leu Gln Leu Pro Glu Leu Lys Gln
                740                 745                 750

Lys Ser Ser Asn Ser Arg Lys Lys Arg Ser Thr Ser Ala Gly Pro Thr
                755                 760                 765

Val Pro Asp Arg Asp Asn Asp Gly Ile Pro Asp Ser Leu Glu Val Glu
                770                 775                 780

Gly Tyr Thr Val Asp Val Lys Asn Lys Arg Thr Phe Leu Ser Pro Trp
785                 790                 795                 800

Ile Ser Asn Ile His Glu Lys Lys Gly Leu Thr Lys Tyr Lys Ser Ser
                805                 810                 815

Pro Glu Lys Trp Ser Thr Ala Ser Asp Pro Tyr Ser Asp Phe Glu Lys
                820                 825                 830

Val Thr Gly Arg Ile Asp Lys Asn Val Ser Pro Glu Ala Arg His Pro
                835                 840                 845

Leu Val Ala Ala Tyr Pro Ile Val His Val Asp Met Glu Asn Ile Ile
                850                 855                 860

Leu Ser Lys Asn Glu Asp Gln Ser Thr Gln Asn Thr Asp Ser Gln Thr
865                 870                 875                 880
```

```
Arg Thr Ile Ser Lys Asn Thr Ser Thr Ser Arg Thr His Thr Ser Glu
            885                 890                 895

Val His Gly Asn Ala Glu Val His Ala Ser Phe Phe Asp Ile Gly Gly
            900                 905                 910

Ser Val Ser Ala Gly Phe Ser Asn Ser Asn Ser Ser Thr Val Ala Ile
            915                 920                 925

Asp His Ser Leu Ser Leu Ala Gly Glu Arg Thr Trp Ala Glu Thr Met
            930                 935                 940

Gly Leu Asn Thr Ala Asp Thr Ala Arg Leu Asn Ala Asn Ile Arg Tyr
945                 950                 955                 960

Val Asn Thr Gly Thr Ala Pro Ile Tyr Asn Val Leu Pro Thr Thr Ser
            965                 970                 975

Leu Val Leu Gly Lys Asn Gln Thr Leu Ala Thr Ile Lys Ala Lys Glu
            980                 985                 990

Asn Gln Leu Ser Gln Ile Leu Ala  Pro Asn Asn Tyr Tyr  Pro Ser Lys
            995                 1000                1005

Asn Leu  Ala Pro Ile Ala Leu  Asn Ala Gln Asp  Asp Phe Ser Ser
    1010                1015                1020

Thr Pro  Ile Thr Met Asn Tyr  Asn Gln Phe Leu  Glu Leu Glu Lys
    1025                1030                1035

Thr Lys  Gln Leu Arg Leu Asp  Thr Asp Gln Val  Tyr Gly Asn Ile
    1040                1045                1050

Ala Thr  Tyr Asn Phe Glu Asn  Gly Arg Val Arg  Val Asp Thr Gly
    1055                1060                1065

Ser Asn  Trp Ser Glu Val Leu  Pro Gln Ile Gln  Glu Thr Thr Ala
    1070                1075                1080

Arg Ile  Ile Phe Asn Gly Lys  Asp Leu Asn Leu Val  Glu Arg Arg
    1085                1090                1095

Ile Ala  Ala Val Asn Pro Ser  Asp Pro Leu Glu Thr  Thr Lys Pro
    1100                1105                1110

Asp Met  Thr Leu Lys Glu Ala  Leu Lys Ile Ala Phe  Gly Phe Asn
    1115                1120                1125

Glu Pro  Asn Gly Asn Leu Gln  Tyr Gln Gly Lys Asp  Ile Thr Glu
    1130                1135                1140

Phe Asp  Phe Asn Phe Asp Gln  Thr Ser Gln Asn  Ile Lys Asn
    1145                1150                1155

Gln Leu  Ala Glu Leu Asn Ala  Thr Asn Ile Tyr Thr  Val Leu Asp
    1160                1165                1170

Lys Ile  Lys Leu Asn Ala Lys  Met Asn Ile Leu Ile  Arg Asp Lys
    1175                1180                1185

Arg Phe  His Tyr Asp Arg Asn  Asn Ile Ala Val Gly  Ala Asp Glu
    1190                1195                1200

Ser Val  Val Lys Glu Ala His  Arg Glu Val Ile Asn  Ser Ser Thr
    1205                1210                1215

Glu Gly  Leu Leu Leu Asn Ile  Asp Lys Asp Ile Arg  Lys Ile Leu
    1220                1225                1230

Ser Gly  Tyr Ile Val Glu Ile  Glu Asp Thr Glu Gly  Leu Lys Glu
    1235                1240                1245

Val Ile  Asn Asp Arg Tyr Asp  Met Leu Asn Ile Ser  Ser Leu Arg
    1250                1255                1260

Gln Asp  Gly Lys Thr Phe Ile  Asp Phe Lys Tyr  Asn Asp Lys
    1265                1270                1275
```

```
Leu Pro Leu Tyr Ile Ser Asn Pro Asn Tyr Lys Val Asn Val Tyr
    1280            1285            1290

Ala Val Thr Lys Glu Asn Thr Ile Ile Asn Pro Ser Glu Asn Gly
    1295            1300            1305

Asp Thr Ser Thr Asn Gly Ile Lys Lys Ile Leu Ile Phe Ser Lys
    1310            1315            1320

Lys Gly Tyr Glu Ile Gly
    1325
```

DUAL ANTHRAX-PLAGUE VACCINES THAT CAN PROTECT AGAINST TWO TIER-1 BIOTERROR PATHOGENS, BACILLUS ANTHRACIS AND YERSINIA PESTIS

CROSS-REFERENCE TO RELATED APPLICATIONS

This application is a divisional of U.S. patent application Ser. No. 15/892,772 filed Feb. 9, 2018, now U.S. Pat. No. 10,556,002 issued Feb. 11, 2020, which claims priority to U.S. Provisional Patent Application No. 62/456,825, filed Feb. 9, 2017. The entire contents and disclosures of this patent application is incorporated herein by reference in its entirety.

This application makes reference to the following applications: U.S. Pat. No. 8,148,130, entitled "T4 Bacteriophage Bound to a Substrate," filed Feb. 29, 2008, issued Apr. 3, 2012, which claims the priority of U.S. Provisional patent Application No. 60/904,168 entitled "Liposome-Bacteriophage Complex As Vaccine Adjuvant," filed Mar. 1, 2007; U.S. Pat. No. 8,685,694, entitled "Methods and Compositions Comprising Bacteriophage Nanoparticles," filed Dec. 17, 2004, issued Apr. 1, 2014, which claims priority to U.S. Provisional Application Ser. No. 60/530,527 filed Dec. 17, 2003; U.S. Pat. No. 8,802,418, entitled "Protein and Nucleic Acid Delivery Vehicles, Components and Mechanisms Thereof," filed Apr. 8, 2011, issued Aug. 12, 2014, claims benefit of priority to U.S. Provisional Patent Application No. 61/322,334 entitled "A Promiscuous DNA Packaging Machine from Bacteriophage T4," filed Apr. 9, 2010; U.S. Pat. No. 9,163,262, entitled "In vitro and in vivo delivery of genes and proteins using the bacteriophage T4 DNA packaging machine," filed Dec. 4, 2013, issued Oct. 20, 2015, which claims benefit of priority to U.S. Provisional Patent Application No. 61/774,895 filed Mar. 8, 2013, entitled "In Vitro and In Vivo Delivery of Genes and Proteins Using the Bacteriophage T4 DNA Packaging Machine"; U.S. Pat. No. 9,187,765, entitled "In Vitro And in Vivo Delivery of Genes and Proteins Using the Bacteriophage T4 DNA Packaging Machine," filed Jul. 22, 2014, issued Nov. 17, 2015, which is a divisional of application Ser. No. 14/096,238 filed Dec. 4, 2013, now U.S. Pat. No. 9,163,262, issued Oct. 20, 2015, which claims benefit of priority to U.S. Provisional Patent Application No. 61/774,895 filed Mar. 8, 2013, entitled "In Vitro and In Vivo Delivery of Genes and Proteins Using the Bacteriophage T4 DNA Packaging Machine"; U.S. Pat. No. 9,328,145, entitled "Designing a soluble full-length HIV-1 gp41 trimer," filed Nov. 27, 2013, issued May 3, 2016, which claims benefit of priority to U.S. Provisional Patent Application No. 61/731,147 filed Nov. 29, 2012, entitled "Designing a Soluble Full-Length HIV-1 Gp41 Trimer"; U.S. Pat. No. 9,328,149, entitled "Mutated and bacteriophage T4 nanoparticle arrayed F1-V immunogens from *Yersinia pestis* as next generation plague vaccines," filed Jul. 1, 2014, issued May 3, 2016, which claims benefit of priority to U.S. Provisional Patent Application No. 61/845,487 to Rao and Tao, entitled "Mutated and Bacteriophage T4 Nanoparticle Arrayed F1-V Immunogens from *Yersinia Pestis* as Next Generation Plague Vaccines," filed Jul. 12, 2013; U.S. Pat. No. 9,365,867, entitled "Protein and Nucleic Acid Delivery Vehicles, Components and Mechanisms Thereof," filed Mar. 12, 2013, issued Jun. 14, 2016, which is a divisional application of U.S. patent application Ser. No. 13/082,466, filed Apr. 8, 2011, now U.S. Pat. No. 8,802,418, issued Aug. 12, 2014, which claims benefit of priority to U.S. Provisional Patent Application No. 61/322,334 entitled "A Promiscuous DNA Packaging Machine from Bacteriophage T4" filed Apr. 9, 2010; U.S. Pat. No. 9,523,101, entitled "Protein and nucleic acid delivery vehicles, components and mechanisms thereof," filed Jul. 2, 2014, issued Dec. 20, 2016, which claims benefit of priority to U.S. patent application Ser. No. 13/082,466 to Rao, entitled "Protein and Nucleic Acid Delivery Vehicle, Components and Mechanisms Thereof" filed Apr. 8, 2011, now U.S. Pat. No. 8,802,418; and U.S. Provisional Patent Application No. 61/322,334 entitled "A Promiscuous DNA Packaging Machine from Bacteriophage T4," filed Apr. 9, 2010; U.S. Pat. No. 9,580,477, entitled "Approach to produce HIV-1 GP140 envelope protein trimers," filed Jul. 23, 2015, issued Feb. 28, 2017, which claims benefit of priority to U.S. Provisional Patent Application No. 62/133,578, entitled "A New Approach to Produce HIV-1 Gp140 Envelope Protein Trimers," filed Mar. 16, 2015; U.S. Provisional Patent Application No. 62/166,271, entitled "A New Approach to Produce HIV-1 Envelope Trimers: Both Cleavage and Proper Glycosylation are Essential to Generate Authentic Trimers," filed May 26, 2015; U.S. Pat. No. 9,701,722, entitled "Designing a Soluble Full-Length HIV-1 Gp41 Trimer," filed Mar. 25, 2016, issued Jul. 11, 2017, which claims benefit of priority to U.S. Provisional Patent Application No. 61/731,147 filed Nov. 29, 2012, entitled "Designing a Soluble Full-Length HIV-1 Gp41 Trimer"; U.S. Pat. No. 9,834,583, entitled "Authentic Trimeric HIV-1 GP140 Envelope Glycoproteins Comprising a Long Linker and Tag," filed Jul. 23, 2015, issued Dec. 5, 2017, which claims benefit of priority to U.S. Provisional Patent Application No. 62/133,578, entitled "A New Approach to Produce HIV-1 Gp140 Envelope Protein Trimers," filed Mar. 16, 2015; U.S. Provisional Patent Application No. 62/166,271, entitled "A New Approach To Produce HIV-1 Envelope Trimers: Both Cleavage And Proper Glycosylation Are Essential To Generate Authentic Trimers," filed May 26, 2015; U.S. Pat. No. 9,850,288, entitled "Method of purifying authentic trimeric HIV-1 envelope glycoproteins comprising a long linker and tag," filed Jul. 23, 2015, issued Dec. 26, 2017, which claims benefit of priority to U.S. Provisional Patent Application No. 62/133,578, entitled "A New Approach to Produce HIV-1 Gp140 Envelope Protein Trimers," filed Mar. 16, 2015; U.S. Provisional Patent Application No. 62/166,271, entitled "A New Approach to Produce HIV-1 Envelope Trimers: Both Cleavage and Proper Glycosylation are Essential to Generate Authentic Trimers," filed May 26, 2015; U.S. patent application Ser. No. 14/806,735, entitled "Approach to Produce HIV-1 Gp140 Envelope Protein Trimers," filed Jul. 23, 2015, now U.S. Pat. No. 9,850,288, entitled "Method of Purifying Authentic Trimeric HIV-1 Envelope Glycoproteins Comprising a Long Linker and Tag," issued Dec. 26, 2017, which claims benefit of priority to U.S. Provisional Patent Application No. 62/133,578, entitled "A New Approach to Produce Hiv-1 Gp140 Envelope Protein Trimers," filed Mar. 16, 2015; U.S. Provisional Patent Application No. 62/166,271, entitled "A New Approach to Produce HIV-1 Envelope Trimers: Both Cleavage and Proper Glycosylation are Essential to Generate Authentic Trimers," filed May 26, 2015; U.S. patent application Ser. No. 14/806,751, entitled "Approach to Produce HIV-1 Gp140 Envelope Protein Trimers," filed Jul. 23, 2015, now U.S. Pat. No. 9,944,679, entitled "Authentic Trimeric HIV-1 Envelope Glycoproteins Comprising a Long Linker and Tag," issued Apr. 17, 2018, which claims benefit of priority to U.S. Provisional Patent Application No. 62/133,578, entitled "A New Approach to Produce HIV-1 Gp140 Envelope Protein Trimers," filed Mar. 16, 2015; and U.S. Provisional Patent Application No. 62/166,271, entitled "A New Approach to Produce HIV-1 Envelope Trimers: Both Cleavage and Proper Glycosylation are Essential to Generate Authentic Trimers," filed May 26, 2015. The entire disclosure and contents of the above applications are hereby incorporated by reference.

This application further makes reference to the following applications: U.S. Provisional Application No. 60/904,168 filed Mar. 1, 2007; U.S. patent application Ser. No. 12/039,803, filed Feb. 29, 2008, now U.S. Pat. No. 8,148,130, issued Apr. 3, 2012; International Application No. PCT/US2008/055422 filed Feb. 29, 2008; U.S. patent application Ser. No. 11/015,294, filed Dec. 17, 2014, now U.S. Pat. No. 8,685,694, issued Apr. 1, 2014; U.S. Provisional Application No. 61/322,334, filed Apr. 9, 2010; International Application No. PCT/IB2011/015133, filed Apr. 8, 2011; U.S. Provisional Application No. 62/133,578, filed Mar. 16, 2015; U.S. patent application Ser. No. 14/806,727, filed Jul. 23, 2015, now U.S. Pat. No. 9,834,583, issued Dec. 5, 2017; International Application No. PCT/IB2016/054176, filed Jul. 13, 2016; U.S. patent application Ser. No. 14/806,735, filed Jul. 23, 2015, now U.S. Pat. No. 9,850,288, issued Dec. 26, 2017; U.S. patent application Ser. No. 14/806,739, filed Jul. 23, 2015, now U.S. Pat. No. 9,580,477, issued Feb. 28, 2017; U.S. patent application Ser. No. 14/806,742, filed Jul. 23, 2015, now U.S. Pat. No. 9,975,924, issued May 22, 2018; U.S. patent application Ser. No. 14/806,751, filed Jul. 23, 2015, now U.S. Pat. No. 9,944,679, issued Apr. 17, 2018; U.S. Provisional Application No. 62/166,271; filed May 26, 2015; International Application No. PCT/IB2016/054207, filed Jul. 14, 2016; International Application No. PCT/IB2016/054250, filed Jul. 15, 2016; International Application No. PCT/IB2016/054260, filed Jul. 18, 2016; International Application No. PCT/IB2016/054292, filed Jul. 19, 2016; U.S. Provisional Application No. 61/731,147 filed Nov. 29, 2012; U.S. patent application Ser. No. 14/091,401, filed Nov. 27, 2013, now U.S. Pat. No. 9,328,145, issued May 3, 2016; International Application No. PCT/IB2013/060453, filed Nov. 27, 2013; U.S. patent application Ser. No. 15/080,804, filed Mar. 25, 2016, now U.S. Pat. No. 9,701,722, issued Jul. 11, 2017; U.S. Provisional Application No. 61/845,487, filed Jul 12, 2013; U.S. patent application Ser. No. 14/320,731, filed Jul. 1, 2014, now U.S. Pat. No. 9,328,149, issued May 3, 2015; International Application No. PCT/IB2014/063005, filed Jul 10, 2014; U.S. Provisional Application No. 61/774,895, filed Mar. 8, 2013; U.S. patent application Ser. No. 14/096,238, filed Dec. 4, 2013 now U.S. Pat. No. 9,163,262, issued Oct. 20, 2015; International Application No. PCT/IB2014/058716, filed Jan. 31, 2014; and U.S. patent application Ser. No. 14/337,545, filed Jul. 22, 2014, now U.S. Pat. No. 9,187,765, issued Nov. 17, 2015. The entire disclosure and contents of the above applications are hereby incorporated by reference.

GOVERNMENT INTEREST STATEMENT

This invention was made with government support under Grant NIH-5R01AI111538 awarded by the National Institutes of Allergy and Infectious Diseases. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 109007-440002_ST25.txt. The text file is 28 KB, was created on Feb. 8, 2018, and is being submitted electronically via EFS-Web, concurrent with the filing of the specification.

BACKGROUND

Field of the Invention

The present invention generally relates to vaccines against anthrax and plague pathogens.

Related Art

Bioterrorism remains as one of the biggest challenges to global security and public health. Since the deadly anthrax attacks of 2001 in the United States, *Bacillus anthracis* and *Yersinia pestis*, the causative agents of anthrax and plague, respectively, gained notoriety and were listed by the CDC as Tier-1 biothreat agents. Currently, there is no Food and Drug Administration-approved vaccine against either of these threats for mass vaccination to protect general public, let alone a bivalent vaccine.

SUMMARY

According to a first broad aspect, the disclosed invention provides an immunogenic composition comprising a triple fusion protein. The triple fusion protein comprises: a mutated F1 antigen from *Yersinia pestis*, a V antigen from *Yersinia pestis*, and a protective antigen (PA) from *B. anthracis*. The mutated F1 antigen, the V antigen, and the PA are fused in-frame. The triple fusion protein has an immunogenicity of the mutated F1 antigen, an immunogenicity of the V antigen, and an immunogenicity of the PA.

According to a second broad aspect, the disclosed invention provides an immunogenic composition comprising one or more bacteriophage nanoparticles arrayed with one or more Soc fusion proteins on capsid surface of each bacteriophage nanoparticle, wherein the one or more Soc fusion proteins comprises a Soc fused to an antigen selected from the group consisting of a mutated F1 antigen from *Yersinia pestis*, a V antigen from *Yersinia pestis*, a protective antigen (PA) from *B. anthracis*, and combination thereof.

According to a third broad aspect, the disclosed invention provides a method comprising: administering to a subject in need thereof a therapeutically effective amount of an immunogenic composition. The immunogenic composition comprises a triple fusion protein and/or one or more bacteriophage nanoparticles, each bacteriophage nanoparticle being arrayed with one or more Soc fusion proteins on capsid surface of the bacteriophage nanoparticle. The triple fusion protein comprises an in-framed fused mutated F1 antigen from *Yersinia pestis*, an in-framed fused V antigen from *Yersinia pestis*, and an in-framed fused protective antigen (PA) from *B. anthracis*. The one or more Soc fusion proteins comprises a Soc fused to an antigen selected from the group consisting of a mutated F1 antigen from *Yersinia pestis*, a V antigen from *Yersinia pestis*, a protective antigen (PA) from *B. anthracis*, and a combination thereof. The immunogenic composition is able to elicit immune response in the subject against anthrax and plague pathogens.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 1A is a schematic illustration of anthrax toxin pathway.

FIG. 1B is a schematic illustration of Y. pestis surface components targeted for vaccine design.

FIG. 2B is a structural model of F1mutV-PA triple antigen according to one embodiment of the present invention.

FIG. 2C illustrates the binding of F1mutV-PA to PA receptor, CMG2, according to one embodiment of the present invention.

FIG. 2D illustrates furin cleavage of F1mutV-PA according to one embodiment of the present invention.

FIG. 2E illustrates the binding of F1mutV-PA to N-terminal domain of lethal factor (LFn) according to one embodiment of the present invention.

FIG. 4A shows vaccine formulations used in various immunized mouse groups according to one embodiment of the present invention.

FIG. 4B illustrates the immunization scheme according to one embodiment of the present invention.

FIG. 4C is a graph illustrating F1V-specific antibody titers according to one embodiment of the present invention.

FIG. 4D is a graph showing PA-specific antibody titers according to one embodiment of the present invention.

FIG. 4E is a graph showing LeTx-neutralizing antibody titers according to one embodiment of the present invention.

FIG. 6A is a graph illustrating survival of the mice against anthrax toxin and plague sequential challenge according to one embodiment of the present invention.

FIG. 6B is a graph illustrating survival of the mice against anthrax toxin and plague simultaneous challenge according to one embodiment of the present invention.

FIG. 6C are in vivo imaging of infected mice according to one embodiment of the present invention.

FIG. 7C is a graph showing F1V-specific antibody (total IgG) titers according to one embodiment of the present invention.

FIG. 7D is a graph showing PA-specific antibody (total IgG) titers according to one embodiment of the present invention.

FIG. 7E is a graph showing LeTx neutralizing antibody titers according to one embodiment of the present invention.

FIG. 8A is a graph showing survival of the rats against anthrax toxin and plague sequential challenge according to one embodiment of the present invention.

FIG. 8B is a set of in vivo imaging of infection according to one embodiment of the present invention.

FIG. 8C is a graph showing survival of the rats against anthrax LeTx and plague simultaneous challenge according to one embodiment of the present invention.

FIG. 9A is a table showing vaccine formulations used in various groups according to one embodiment of the present invention.

FIG. 9B is an immunization scheme for rabbit study according to one embodiment of the present invention.

FIG. 9C is a graph showing F1V-specific antibody (total IgG) titers on day 20 according to one embodiment of the present invention.

FIG. 9D is a graph showing F1V-specific antibody (total IgG) titers on day 42 according to one embodiment of the present invention.

FIG. 9E is a graph showing protective antigen (PA)-specific antibody (total IgG) titers according to one embodiment of the present invention.

FIG. 9F is a graph showing LeTx neutralizing antibody titer.

FIG. 9G is a graph showing survival of the rabbits challenged with 200 LD50 of aerosolized B. anthracis Ames spores according to one embodiment of the present invention.

FIG. 13A is a graph showing F1V-specific IgG1 antibody titers in rats according to one embodiment of the present invention.

FIG. 13B is a graph showing F1V-specific IgG2a antibody titers in rats according to one embodiment of the present invention.

BRIEF DESCRIPTION OF THE SEQUENCES

Figure 2A:
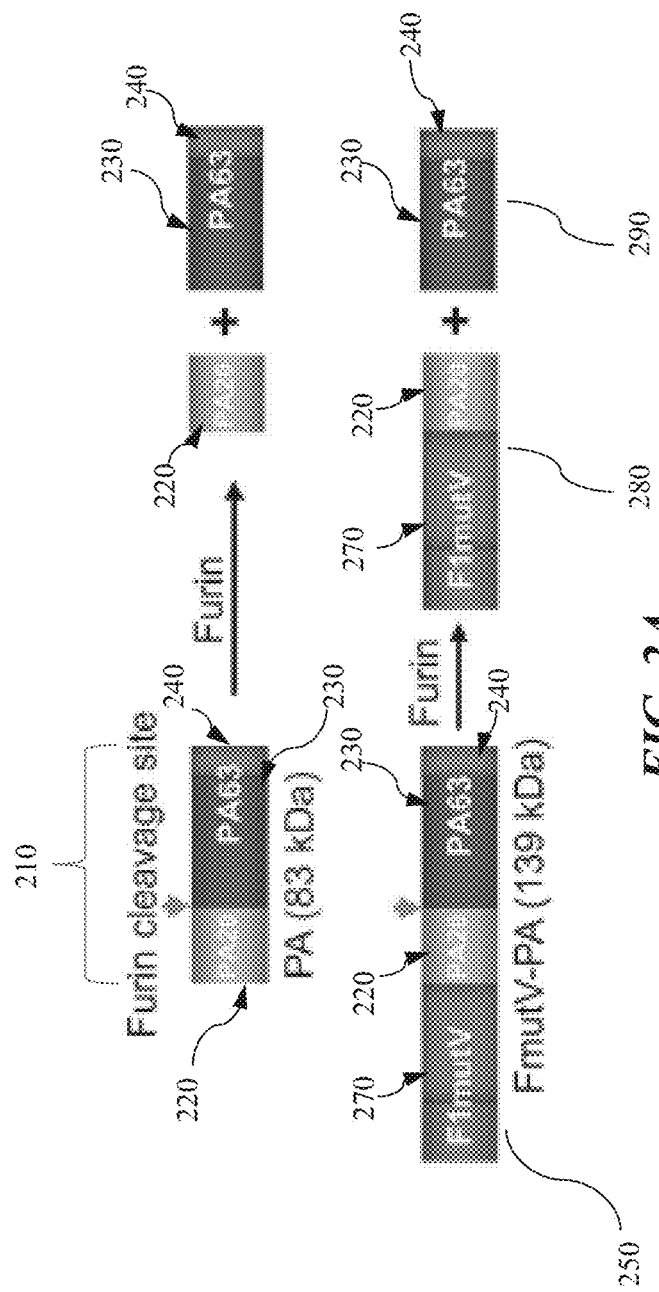
FIG. 2A is a schematic illustrating protective antigen (PA) and F1mutV-PA recombinant constructs according to one embodiment of the present invention.
Figure 3A:
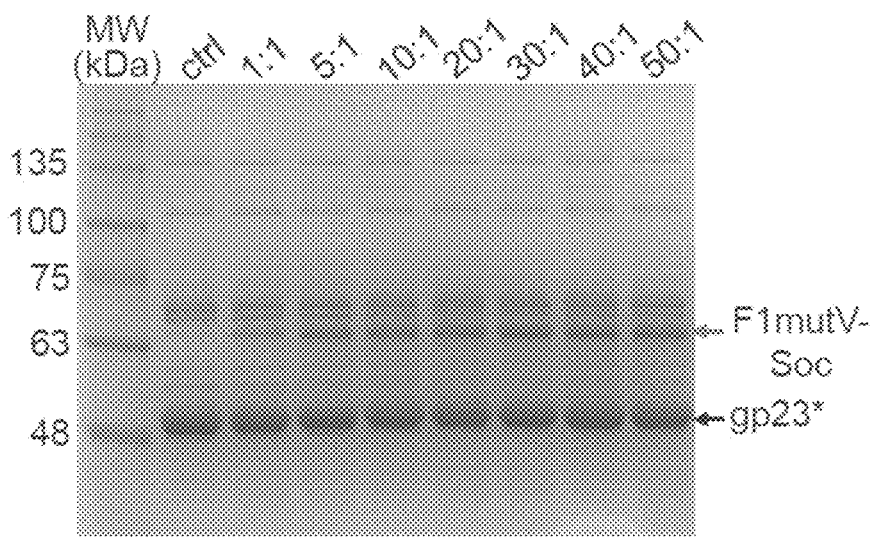
FIGS. 3A, 3B, 3C, and 3D illustrate the display of F1mutV-Soc and Soc-PA on Hoc-Soc-bacteriophage T4 according to one embodiment of the present invention.
Figure 3B:
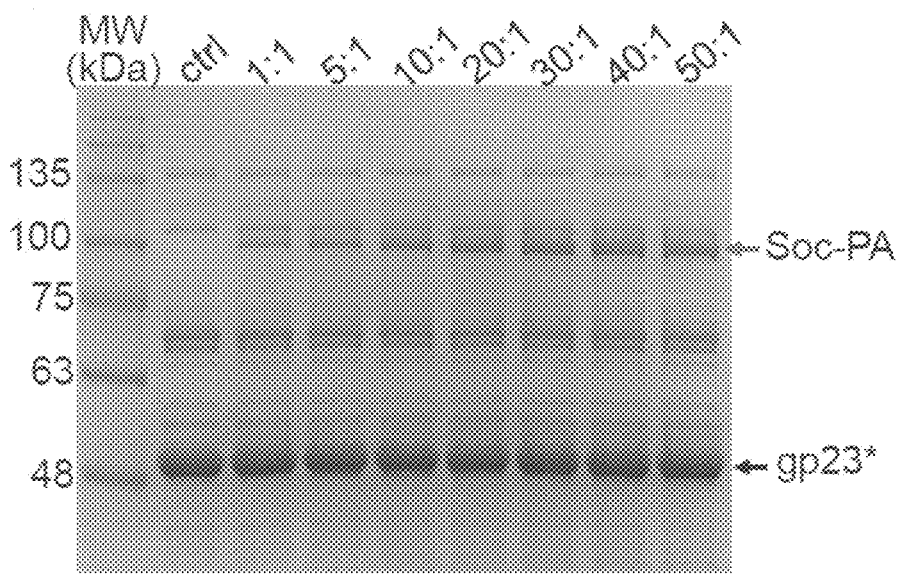
Figure 3C:
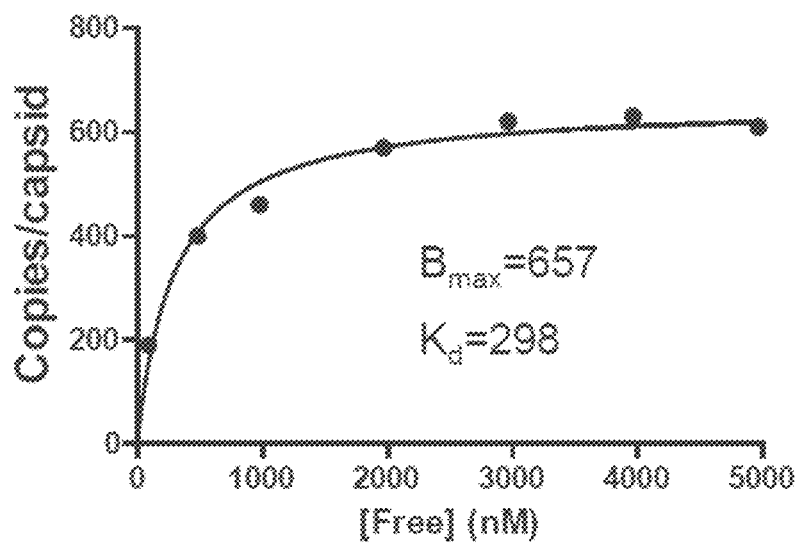
Figure 3D:
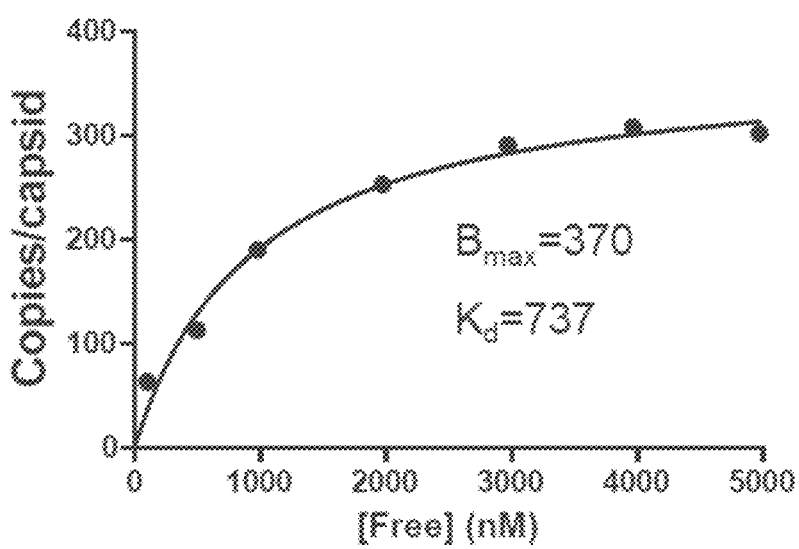

SEQ ID NO: 1 is an amino acid sequence corresponding to mutant F1mut according to one embodiment of the present invention.

SEQ ID NO: 2 is an amino acid sequence corresponding to V antigen from *Y. pestis* according to one embodiment of the present invention.

SEQ ID NO: 3 is an amino acid sequence corresponding to PA from *B. anthracis* according to one embodiment of the present invention.

SEQ ID NO: 4 is an amino acid sequence corresponding to F1mutV-PA triple antigen according to one embodiment of the present invention.

SEQ ID NO: 5 is a nucleic acid sequence encoding recombinant protein F1mutV according to one embodiment of the present invention.

SEQ ID NO: 6 is a nucleic acid sequence encoding PA according to one embodiment of the present invention.

SEQ ID NO: 7 is an amino acid sequence corresponding to furin cleavage site at PA.

SEQ ID NO: 8 is a nucleic acid sequence of a primer according to one embodiment of the present invention.

SEQ ID NO: 9 is a nucleic acid sequence of a primer according to one embodiment of the present invention.

SEQ ID NO: 10 is a nucleic acid sequence for a primer according to one embodiment of the present invention.

SEQ ID NO: 11 is a nucleic acid sequence of a primer according to one embodiment of the present invention.

SEQ ID NO: 12 is an amino acid sequence of a peptide linker according to one embodiment of the present invention.

SEQ ID NO: 13 is a nucleic acid sequence of a primer according to one embodiment of the present invention.

SEQ ID NO: 14 is a nucleic acid sequence of a primer according to one embodiment of the present invention.

SEQ ID NO: 15 is a nucleic acid sequence of RB69 Soc according to one embodiment of the present invention.

SEQ ID NO: 16 is an amino acid sequence of RB49 Soc according to one embodiment of the present invention.

SEQ ID NO: 17 is a nucleic acid sequence of fusion protein F1mutV-Soc-PA according to one embodiment of the present invention.

SEQ ID NO: 18 is an amino acid sequence of fusion protein F1mutV-Soc-PA according to one embodiment of the present invention.

DETAILED DESCRIPTION OF THE INVENTION

Definitions

Where the definition of terms departs from the commonly used meaning of the term, applicant intends to utilize the definitions provided below, unless specifically indicated.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. For example, the term "a protein antigen" includes a plurality of protein antigens, including mixtures thereof. In this application, the use of "or" means "and/or" unless stated otherwise. Furthermore, use of the term "including" as well as other forms, such as "include", "includes," and "included," is not limiting.

For purposes of the present invention, the term "comprising", the term "having", the term "including," and variations of these words are intended to be open-ended and mean that that the compositions and methods include the recited elements, but do not exclude other elements.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, a value or property is "based" on a particular value, property, the satisfaction of a condition, or other factor, if that value is derived by performing a mathematical calculation or logical decision using that value, property or other factor.

For purposes of the present invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purpose of the present invention, the term "adjacent" refers to "next to" or "adjoining something else."

For purposes of the present invention, the term "adjuvant" refers to a composition comprised of one or more substances that enhances the immune response to an antigen(s). The mechanism of how an adjuvant operates is not entirely known. Some adjuvants are believed to enhance the immune response by slowly releasing the antigen, while other adjuvants are strongly immunogenic in their own right and are believed to function synergistically.

For purpose of the present invention, the phase "administration of a vaccine" refers to introduce a vaccine into a body of an animal or a human being. As is understood by an ordinary skilled person, it can be done in a variety of manners. For example, administration of a vaccine may be done intramuscularly, subcutaneously, intravenously, intranasally, intradermaly, intrabursally, in ovo, ocularly, orally, intra-tracheally or intra-bronchially, as well as combinations of such modalities. The dose of the vaccine may vary with the size of the intended vaccination subject.

For purposes of the present invention, the term "antigen" refers to a compound, composition, or immunogenic substance that can stimulate the production of antibodies or a T-cell response, or both, in an animal, including compositions that are injected or absorbed into an animal. The immune response may be generated to the whole molecule, or to a portion of the molecule (e.g., an epitope or hapten).

For purpose of the present invention, the term "array" refers to in vitro binding of a protein on a bacteria phage. For example, a Soc fusion protein, a protein fused with a small outer capsid protein Soc of a bacteriophage T4, may be arrayed by incubating Hoc-Soc-T4 phage particles with the Soc fusion protein to allow the Soc fusion protein to bind on Hoc-Soc-T4 phage particles.

For purposes of the present invention, the term "bind," the term "binding" or the term "bound" refers to any type of chemical or physical binding, which includes but is not limited to covalent binding, hydrogen binding, electrostatic binding, biological tethers, transmembrane attachment, cell surface attachment and expression.

For purposes of the present invention, the term "biological sample" and the term "biological specimen" refers to either a part or the whole of a human, animal, microbe or plant in vitro or in vivo. The term includes but is not limited to material of human, animal, microbe or plant origin such as human, animal, microbial or plant tissue sections, cell or tissue cultures, suspension of human, animal, microbial or plant cells or isolated parts thereof, human or animal biopsies, blood samples, cell-containing fluids and secretion.

For purpose of the present invention, the term "bivalent" refers to a composition that has two combining sites, for example, a bivalent immunogen capable of binding to two molecules of antibodies.

For purposes of the present invention, the term "capsid" and the term "capsid shell" refers to a protein shell of a virus comprising several structural subunits of proteins. The capsid encloses the nucleic acids of the virus. Capsids are broadly classified according to their structures. The majority of viruses have capsids with either helical or icosahedral structures For purpose of the present invention, the term "capsomere" refers to a basic substructure of a capsid, an outer covering of proteins that protects the genetic materials of a virus. Capsomeres self-assemble to form the capsid.

For purpose of the present invention, the term "cleft" refers to a groove or a V-shaped indentation that runs across two protein domains.

For purpose of the present invention, the term "correspond" and the term "corresponding" refer to that a protein sequence refer interchangeably to an amino acid position(s) of a protein. An amino acid at a position of a protein may be found to be equivalent or corresponding to an amino acid at a position of one or more other protein(s) based on any relevant evidence, such as the primary sequence context of the each amino acid, its position in relation to the N-terminal and C-terminal ends of its respective protein, the structural and functional roles of each amino acid in its respective protein, etc.

For purposes of the present invention, the term "domain" and the term "protein domain" refer to a distinct functional or structural unit in a protein. Usually, a protein domain is responsible for a particular function or interaction, contributing to the overall role of a protein. Domains may exist in a variety of biological contexts, where similar domains can be found in proteins with different functions.

For purposes of the present invention, the term "dosage" refers to the administering of a specific amount, number, and frequency of doses over a specified period of time. Dosage implies duration. A "dosage regimen" is a treatment plan for administering a drug over a period of time.

For purposes of the present invention, the term "dosage form," the term "form," or the term "unit dose" refers to a method of preparing pharmaceutical products in which individual doses of medications are prepared and delivered. Dosage forms typically involve a mixture of active drug components and nondrug components (excipients), along with other non-reusable material that may not be considered either ingredient or packaging.

For purposes of the present invention, the term "dose" refers to a specified amount of medication taken at one time.

For purpose of the present invention, the term "duplicate" refers to repeat or generate another identical copy of a polynucleotide sequence or an amino acid sequence.

For purpose of the present invention, the term "epitope" refers to a molecular region on the surface of an antigen capable of eliciting an immune response and combining with the specific antibody produced by such a response. It is also called "antigenic determinant." T cell epitopes are presented on the surface of an antigen-presenting cell, where they are bound to MHC molecules.

For purposes of the present invention, the term "effective amount" or "effective dose" or grammatical variations thereof refers to an amount of an agent sufficient to produce one or more desired effects. The effective amount may be determined by a person skilled in the art using the guidance provided herein.

For purposes of the present invention, the term "engineered" refers to being made by biological engineering.

For purposes of the present invention, the term "excipient" refers to a natural or synthetic substance formulated alongside the active ingredient of a medication, included for the purpose of bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients also depends upon the route of administration and the dosage form, as well as the active ingredient and other factors. Though excipients were at one time considered to be "inactive" ingredients, they are now understood to be "a key determinant of dosage form performance."

For purposes of the present invention, the term "expression" and the term "gene expression" refer to a process by which information from a gene or a fragment of DNA is used in the synthesis of a functional gene product. A gene which encodes a protein will, when expressed, be transcribed and translated to produce that protein.

For purposes of the present invention, the term "expression vector," otherwise known as an expression construct, refers to a plasmid or virus designed for protein expression in cells. The vector is used to introduce a specific gene into a target cell, and can commandeer the cell's mechanism for protein synthesis to produce the protein encoded by the gene. The plasmid is engineered to contain regulatory sequences that act as enhancer and promoter regions and lead to efficient transcription of the gene carried on the expression vector. The goal of a well-designed expression vector is the production of significant amount of stable messenger RNA, and therefore proteins.

For purpose of the present invention, the term "fragment" of a molecule such as a protein or nucleic acid refers to a portion of the amino acid or nucleotide sequence.

For purposes of the present invention, the term "furin" refers to a protein encoded by the FURIN gene. Some proteins are inactive when they are first synthesized, and must have sections deleted in order to become active. Furin deletes these sections and activates the proteins.

For purpose of the present invention, the term "fuse" refers to join together physically, or to make things join together and become a single thing.

For purpose of the present invention, the term "fusion polypeptide" or the term "fusion protein" refers to a polypeptide or a protein created through the joining of two or more genes that originally coded for separate proteins. Translation of this fusion gene results in a single or multiple polypeptides with functional properties derived from each of the original proteins. Usually, a fusion protein has at least two heterologous polypeptides covalently linked, either directly or via an amino acid linker. The heterologous polypeptides forming a fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides. These terms encompass conservatively modified variants, polymorphic variants, alleles, mutants, subsequences, interspecies homologs, and immunogenic fragments of the antigens that make up the fusion protein. In present invention, "fusion protein" and "recombinant protein" are interchangeable. Fusion proteins of the disclosure may also comprise additional copies of a component antigen or immunogenic fragment thereof. Recombinant fusion proteins are created artificially by recombinant DNA technology for use in biological research or therapeutics.

For purposes of the present invention, the term "gel electrophoresis" refers to a method for separation and analysis of macromolecules (DNA, RNA and proteins) and their fragments, based on their size and charge. Gel electrophoresis conditions include denaturing condition and native condition (non-denaturing condition). Under denaturing condition, molecules such as proteins are denatured in a solution containing a detergent (SDS). In these conditions, for example, proteins are unfolded and coated with negatively charged detergent molecules. Proteins in SDS-PAGE are then separated on the sole basis of their size. The protein migrates as bands based on size. Each band can be detected using stains such as Coomassie blue dye or silver stain. Unlike denaturing methods, native gel electrophoresis does not use a charged denaturing agent. Under native condition, molecules such as proteins maintain their natural structures. The molecules being separated therefore differ not only in molecular mass and intrinsic charge, but also the cross-sectional area, and thus experience different electrophoretic forces dependent on the shape of the overall structure. For proteins, since they remain in the native state they may be visualized not only by general protein staining reagents but also by specific enzyme-linked staining.

For purposes of the present invention, the term "gene" refers to a nucleic acid (e.g., DNA or RNA) sequence that comprises coding sequences necessary for the production of an RNA or a polypeptide or its precursor. The term "portion," when used in reference to a gene, refers to fragments of that gene. The fragments may range in size from a few nucleotides to the entire gene sequence minus one nucleotide.

For purpose of the present invention, the term "identical" or the term "identity" refers to the percentage of amino acid residues of two or more polypeptide sequences having the same amino acid at corresponding positions.

For purposes of the present invention, the term "immune response" refers to a specific response elicited in an animal. An immune response may refer to cellular immunity (CMI); humoral immunity or may involve both. The present invention also contemplates a response limited to a part of the immune system. Usually, an "immunological response" includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

For purposes of the present invention, the term "immunity" refers to a state of resistance of a subject animal including a human to an infecting organism or substance. It will be understood that an infecting organism or substance is defined broadly and includes parasites, toxic substances, cancer cells and other cells as well as bacteria and viruses.

For purposes of the present invention, the term "immunization conditions" refers to factors that affect an immune response including the amount and kind of immunogen or adjuvant delivered to a subject animal including a human, method of delivery, number of inoculations, interval of inoculations, the type of subject animal and its condition. "Vaccine" refers to pharmaceutical formulations able to induce immunity.

For purposes of the present invention, the term "immunization dose" refers to the amount of antigen or immunogen needed to precipitate an immune response. This amount will vary with the presence and effectiveness of various adjuvants. This amount will vary with the animal and the antigen, immunogen and/or adjuvant. The immunization dose is easily determined by methods well known to those skilled in the art, such as by conducting statistically valid host animal immunization and challenge studies.

For purposes of the present invention, the term "immunogen," the term "immunogenic composition," or the term "immunological composition" refers to a substance or material (including antigens) that is able to induce an immune response alone or in conjunction with an adjuvant. Both natural and synthetic substances may be immunogens.

For purposes of the present invention, the term "immunogenicity" refers to the ability to of a particular substance, such as an antigen or epitope, to provoke an immune response in the body of a human or animal. In other words, immunogenicity is the ability to induce a humoral and/or cell-mediated immune responses.

For purposes of the present invention, the term "individual" refers to a mammal. For example, the term "individual" may refer to a human individual.

For purposes of the present invention, the term "immunogenic amount" is an amount of an antigen preparation of interest or amount of a biological toxin that elicits a clinically detectable protective response in an animal.

For purposes of the present invention, the term "junction," the term "junction fragment," the term "junction sequence," and the term "junction peptide" are interchangeable and refer to a region or a fragment or a portion of peptide between two subunits or sections within a polypeptide. The two subunits or sections meet or join via the junction fragment.

For purpose of the present invention, the term "linked" refers to a covalent linkage between two polypeptides in a fusion protein. The polypeptides are typically joined via a peptide bond, either directly to each other or via one or more additional amino acids.

For purpose of the present invention, the term "linker" refers to short peptide sequences that occur between functional protein domains and link the functional domains together. Linkers designed by researchers are generally classified into three categories according to their structures: flexible linkers, rigid linkers, and in vivo cleavable linkers. A flexible linker is often composed of flexible residues like glycine and serine so that the adjacent protein domains are free to move relative to one another. A linker also may play a role in releasing the free functional domain in vivo (as in in vivo cleavable linkers). Linkers may offer many other advantages for the production of fusion proteins, such as improving biological activity, increasing expression yield, and achieving desirable pharmacokinetic profiles. The composition and length of a linker may be determined in accordance with methods well known in the art and may be tested for efficacy.

For purposes of the present invention, the term "modified" and the term "mutant" when made in reference to a gene or to a gene product refer, respectively, to a gene or to a gene product which displays modifications in sequence and/or functional properties (i.e., altered characteristics) when compared to the wild-type gene or gene product.

For purpose of the present invention, the term "monomer" refers to a molecule that may bind chemically to other molecules to form a polymer. The term "monomeric protein" may also be used to describe one of the proteins making up a multiprotein complex For purposes of the present invention, the term "multivalent" refers to a vaccine containing more than one antigen whether from the same species (i.e., different isolates of *Mycoplasma hyopneumoniae*), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

For purposes of the present invention, the term "mutation" refers to a change in the polypeptide sequence of a protein or in the nucleic acid sequence.

For purpose of the present invention, the term "oligomer" refers to a molecular complex that consists of a few monomer units. Dimers, trimers, and tetramers are, for instance, oligomers respectively composed of two, three and four monomers. An oligomer can be a macromolecular complex formed by non-covalent bonding of few macromolecules like proteins or nucleic acids. In this sense, a homo-oligomer would be formed by few identical molecules and by contrast, a hetero-oligomer would be made of three different macromolecules.

For purpose of the present invention, the term "oligomerization" refers to a chemical process that converts monomers to macromolecular complexes through a finite degree of polymerization.

For purposes of the present invention, the term "operably linked," the term "operably associated," and the term "functionally linked" are used interchangeably and refer to a functional relationship between two or more DNA segment. Particularly, "operably linked" may refer to place a first nucleic acid sequence in a functional relationship with the second nucleic acid sequence. For example, a promoter/enhancer sequence, including any combination of cis-acting transcriptional control elements is operably associated to a coding sequence if the promoter/enhancer sequence affects the transcription or expression of the coding sequence in an appropriate host cell or other expression system. Promoter regulatory sequences that are operably linked to the transcribed gene sequence are physically contiguous to the transcribed sequence.

For purposes of the present invention, the term "nucleic acid" and the term "polynucleotide," as used interchangeably herein, refer to polymers of nucleotides of any length, and include DNA and RNA. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example by the action of reverse transcriptase. A polynucleotide may comprise modified nucleotides, such as methylated nucleotides and their analogs.

For purposes of the present invention, the term "parenteral route" refers to the administration of a composition, such as a drug in a manner other than through the digestive tract. Parenteral routes include routes such as intravenous, intra-arterial, transdermal, intranasal, sub-lingual and intraosseous, etc. For example, intravenous is also known as I.V., which is giving directly into a vein with injection. As the drug directly goes into the systemic circulation, it reaches the site of action resulting in the onset the action.

For purposes of the present invention, the term "pharmaceutically acceptable" refers to a compound or drug approved or approvable by a regulatory agency of a federal or a state government, listed or listable in the U.S. Pharmacopeia or in other generally recognized pharmacopeia for use in mammals, including humans. For example, a "pharmaceutically acceptable diluent, excipient, carrier, or adjuvant" is a diluent, excipient, carrier, or adjuvant which is physiologically acceptable to the subject while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art (see, e.g., U.S. Pub. No. 2012/0076812, now U.S. Pat. No. 9,017,691).

As used herein, the terms "pharmaceutically acceptable carrier" and "pharmaceutically acceptable vehicle" are interchangeable and refer to refers to any carrier that does not itself induce the production of antibodies harmful to an individual or a subject receiving a composition. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

For purpose of the present invention, the term "polymer" refers to a compound or a mixture of compounds comprising many repeating subunits, known as monomers.

For purpose of the present invention, the terms "polypeptide" and "protein" are used interchangeably herein to refer to a polymer of amino acid residues. The terms encompass amino acid polymers in which one or more amino acid residues are artificial chemical mimetic of a corresponding naturally occurring amino acids, as well as to naturally occurring amino acid polymers and non-naturally occurring amino acid polymer.

For purpose of the present invention, the term "protein domain" refers to a distinct functional or structural unit in a protein. Usually, a protein domain is responsible for a particular function or interaction, contributing to the overall role of a protein. Domains may exist in a variety of biological contexts, where similar domains can be found in proteins with different functions.

For purposes of the present invention, the term "protein purification" refers to a series of processes intended to isolate one or a few proteins from a complex mixture, such as cell culture media, cells, tissues or whole organisms, etc. Usually a protein purification protocol contains one or more chromatographic steps. The basic procedure in chromatography is to flow the solution containing the protein through a column packed with various materials. Different proteins interact differently with the column material, and can thus be separated by the time required to pass the column, or the conditions required to elute the protein from the column. Many purification strategies exist. For example, a protein can be attached with an antigen peptide tag by engineering and be purified using an antibody against the antigen peptide tag. Usually, during purification, the protein with an antigen peptide tag can be added on a column loaded with resin that is coated with an antibody or by incubating with a loose resin that is coated with an immobilizing antibody. This particular procedure is known as immunoprecipitation. Immunoprecipitation is quite capable of generating an extremely specific interaction which usually results in binding only the desired protein. The purified tagged proteins can then easily be separated from the other proteins in solution and later eluted back into clean solution.

For purposes of the present invention, the term "purified" refers to the component in a relatively pure state, e.g. at least about 90% pure, or at least about 95% pure, or at least about 98% pure.

For purpose of the present invention, the term "recombinant protein" refers to a protein derived from a recombinant DNA, that is, it's code is carried by a "recombinant DNA" molecule. Recombinant DNA molecules are DNA molecules formed by laboratory methods of genetic recombination (such as molecular cloning) to bring together genetic material from multiple sources, creating sequences that would not otherwise be found in biological organisms.

For purpose of the present invention, the term "recombinant vaccine" refers to a vaccine made by genetic engineering, the process and method of manipulating the genetic material of an organism. Usually, a recombinant vaccine encompasses one or more protein antigens that have either been produced and purified in a heterologous expression system (e.g., bacteria or yeast) or purified from large amounts of the pathogenic organism. The vaccinated person produces antibodies to the one or more protein antigens, thus protecting him/her from disease.

For purposes of the present invention, the term "stimulate," the term "immuno-stimulate" refers to induce the activation or increase the activity of any components in an immune system. For example, T cell activation requires at least two signals to become fully activated. The first occurs after engagement of the T cell antigen-specific receptor (TCR) by the antigen-major histocompatibility complex (MHC), and the second by subsequent engagement of co-stimulatory molecules. Once stimulated, the T cells will recognize the antigen or vaccine used during stimulation or activation of the T cells.

For purpose of the present invention, the term "subunit" refers to a separate polypeptide chain that makes a certain protein which is made up of two or more polypeptide chains joined together. In a protein molecule composed of more than one subunit, each subunit can form a stable folded structure by itself. The amino acid sequences of subunits of a protein can be identical, similar, or completely different.

For purpose of the present invention, the term "subject" or the term "individual" refers interchangeably to a mammalian organism, such as a human, mouse, etc., that is administered a mutant protein of the present invention for a therapeutic or experimental purpose.

For purpose of the present invention, the term "suitable vector" refers to any vector (for example, a plasmid or virus) which may incorporate a nucleic acid sequence encoding an antigenic polypeptide and any desired control sequences. It may bring about the expression of the nucleic acid sequence. The choice of the vector will typically depend on the compatibility of the vector with a host cell into which the vector is to be introduced.

For purpose of the present invention, the term "type three secretion system (T3SS)" refers to a protein appendage found in *Yersinia*, a genus of Gram-negative rod shaped bacteria that cause the plague. T3SS is also called "injectisome" or "injectosome," with a needle-like structure used as a sensory probe to detect the presence of eukaryotic organisms and secrete proteins that help the bacteria infect them. T3SS are essential for the pathogenicity of many pathogenic bacteria.

For purpose of the present invention, the term "transplant" refers to move or transfer a fragment of a DNA or a protein to another place or situation. For example, the NH2-terminal amino acid residues of a protein may be "transplanted" to the COOH-terminus of the protein by deleting the NH2-terminal amino acid residues and fusing them to the COOH-terminus of the protein via a short linker wherein the short linker joins the deleted NH2-terminal amino acid residues to the COOH-terminus of the protein.

For purposes of the present invention, the term "targeting ligand" refers to proteins or receptors displayed on the surface of cells like dendritic cells and antigen-presenting cells. The binding of a targeting ligand to an antigen-presenting or dendritic cell is required for cellular activation and induction of a variety of downstream effects.

For purposes of the present invention, the term "targeting molecule" refers to a naturally existing cellular or molecular structure involved in the pathology of interest that the drug-in-development is meant to act on.

For purpose of the present invention, the term "vaccine" refers to a biological compound that improves immunity to a particular disease. A vaccine typically contains an agent that resembles a disease-causing microorganism (microbe), such as virus, bacteria, fungus, etc. Traditionally, it is often made from weakened or killed forms of the microbe, its toxins, or one of its surface proteins. The agent injected into a human or animal body stimulates the body's immune system to recognize the agent as foreign, destroy it, and keep a record of it, so that the immune system can more easily recognize and destroy any of these microorganisms that it later encounters.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, transdermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

For purposes of the present invention, the term "variant" refers to a polypeptide or a nucleic acid sequence encoding a polypeptide that has one or more conservative amino acid variations or other minor modifications such that the corresponding polypeptide has substantially equivalent function when compared to the wild-type polypeptide. For purposes of the present invention, the term "conservative variation" denotes the replacement of an amino acid residue by another biologically similar residue, or the replacement of a nucleotide in a nucleic acid sequence such that the encoded amino acid residue does not change or is another biologically similar residue. Examples of conservative variations include the substitution of one hydrophobic residue, such as isoleucine, valine, leucine or methionine for another hydrophobic residue, or the substitution of one polar residue, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

For purposes of the present invention, the term "virus" refers to an infectious agent that is unable to grow or reproduce outside a host cell and that infects mammals (e.g., humans) or birds.

For purposes of the present invention, the term "virus particle" refers to viruses and virus-like organisms.

DESCRIPTION

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

*Bacillus anthracis* and *Yersinia pestis* are two Tier-1 biothreat agents that pose a great risk to United States' national security and public health due to their exceptionally high virulence.[1-4] *Bacillus anthracis* and *Yersinia pestis* are two of the deadliest bioterror agents. *B. anthracis*, a Gram-positive bacterium, is the causative agent of anthrax, and *Y. pestis*, a Gram-negative bacterium, is the etiological agent of plague. Both are deadly diseases and cause rapid death, in 3-6 days, of 85-100% of exposed individuals, unless antibiotics are administered within 20-24 hours after the onset of symptoms.[1-5] Intentional release of these organisms as a bioweapon could lead to massive deaths, public panic, and social chaos.[1-4] The best way to offset such an attack is to vaccinate people prior to the attack. Vaccination is also essential after the attack to minimize further casualties and to mitigate additional attacks.[6] Consequently, since the anthrax attacks of September 2001, stockpiling of vaccines against anthrax and plague has been a national priority but none have yet been licensed.[1-4]

There are currently no Food and Drug Administration (FDA) approved anthrax or plague vaccines for mass vaccination in humans. The BioThrax vaccine approved for anthrax in 1970s, AVA (anthrax vaccine alum-adsorbed), has been used for high risk individuals such as the military.[7] This vaccine consists of a filtered crude culture supernatant of *B. anthracis* strain V770-NP1-R, but it exhibits significant reactinogenicity in vaccinated individuals.[7-9] A re-formulated version of BioThrax vaccine (Emergent BioSolutions, Gaithersburg, Md.) was recently approved for humans (18-65 years of age) to prevent disease following suspected or confirmed exposure to *B. anthracis* in conjunction with recommended antibiotic treatment(s).[10] The use of this reformulated vaccine is also currently limited to military and high-risk healthcare workers.[10] Unfortunately, these vaccines require multiple initial doses and subsequent boosters to maintain protective immunity.[7]

Similarly, a killed whole cell (KWC) plague vaccine was in use in the past, also for military and laboratory personnel in the United States, but was discontinued due to high reactinogenicity, and because its protective effect against bubonic plague did not extend to the deadlier pneumonic form of the disease.[11] A live-attenuated plague vaccine, EV76, which is protective against both bubonic and pneumonic plague is used in some parts of the world where plague is endemic, but it is also associated with severe side effects.[12]

Figures 1A, 1B:
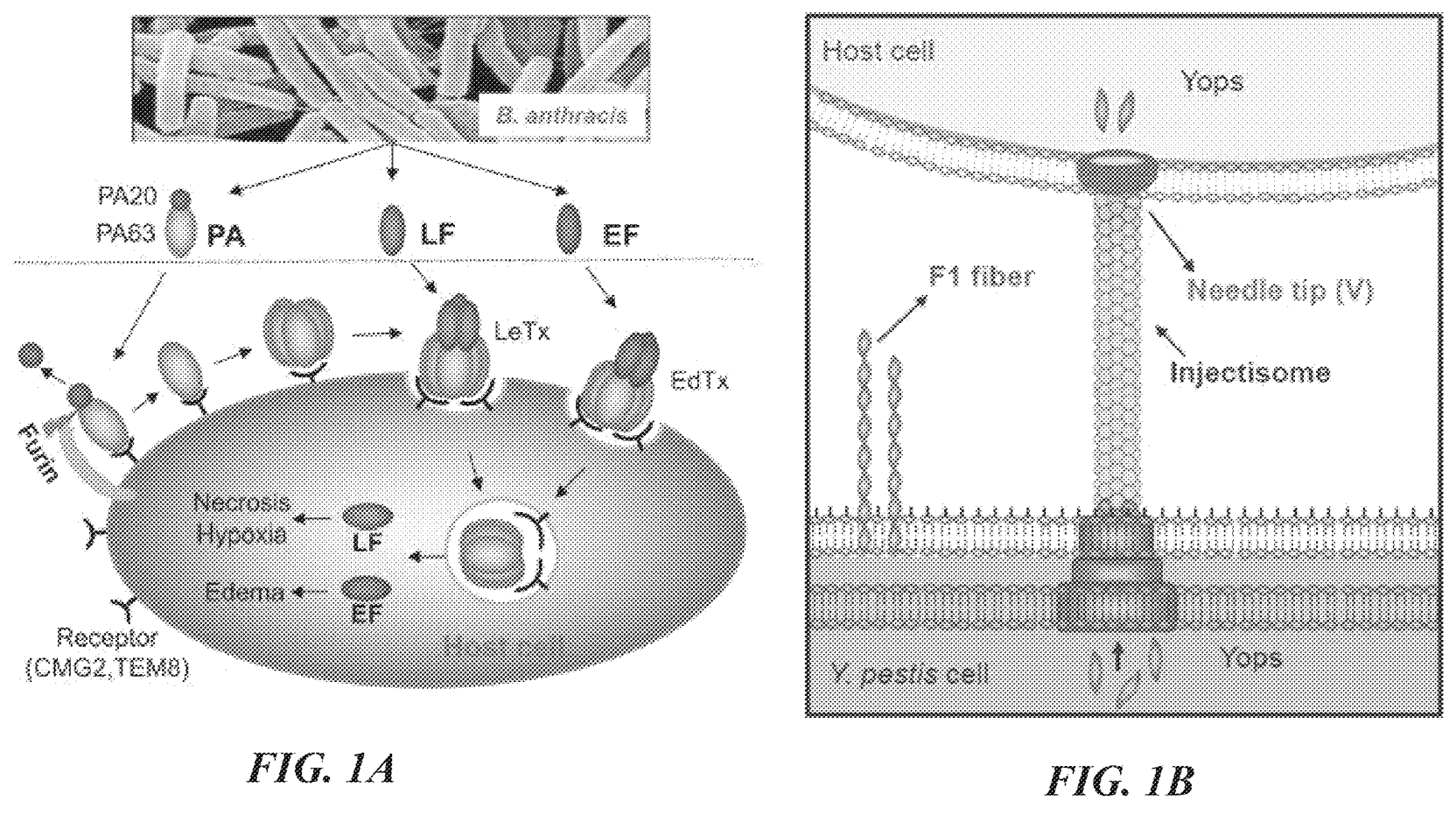

In recent years, the focus has been shifted to subunit vaccines containing pure recombinant proteins. FIG. 1A and FIG. 1B are schematic illustrations of anthrax toxin pathway and *Yersinia pestis* surface components targeted for vaccine design. FIG. 1A is a schematic illustration of anthrax toxin pathway. The protective antigen (PA), a key component of the lethal toxin (LeTx) of *Bacillus anthracis*, has been the principal target for anthrax vaccines.[8,9] As shown in FIG. 1A, PA is the host receptor-binding component of the tripartite anthrax toxin that consists, in addition, of lethal factor (LF) and edema factor (EF)[13] (FIG. 1A). Once bound to the host receptors CMG2 and TEM8, PA is cleaved by furin to generate PA20 (20 kDa) and PA63 (63 kDa). PA63 then oligomerizes to produce a heptamer or octamer that then interacts with lethal factor (LF) and edema factor (EF) to form the LeTx or edema toxin (EdTx), respectively. Translocation of LF and EF through the PA heptamer/octamer channel into the host cell cytosol results in toxic effects. Numerous studies have documented that antibodies against PA alone are sufficient to completely protect animals against lethal, aerosolized *B. anthracis* Ames spore challenge.[6,14] However, the instability of recombinant PA (rPA) when adsorbed on aluminum hydroxide gel and the variable immune responses in humans remained as a barrier for licensing a rPA anthrax vaccine.[15,16]

FIG. 1B is a schematic illustration of *Y. pestis* surface components targeted for vaccine design. As shown in FIG. 1B, F1 is the structural unit of the capsular layer. V forms a pore at the tip of the injectisome needle and facilitates translocation of *Yersinia* outer proteins (Yops) into the host cell. F1 and V are two principal targets for the plague subunit vaccines. Recombinant plague vaccines typically combine two surface-exposed antigens of *Y. pestis*, the capsular protein Caf1 (or F1; 15.6 kDa) and the low calcium response V antigen, LcrV (or V; 37.2 kDa).[11,17] F1 assembles into fibers to form an outer capsular layer, allowing the bacterium to adhere to the host cell and escape phagocytosis.[18] The V antigen forms an oligomeric "pore" at the tip of the "injectisome" needle of the *Y. pestis* type 3 secretion system (T3SS) through which the effector proteins (*Yersinia* outer proteins or Yops) are delivered into the host cell cytosol.[19] Antibodies against F1 and V provide protection against *Y. pestis* infection, although, based on literature, cellular immunity also seems to play a role in providing protective immunity.[11,17] Two types of recombinant F1/V vaccines have been formulated; a mixture of F1 and V proteins, or a single protein containing both F1 and V, the F1-V fusion protein.[20-22] A major concern for licensing these vaccines is that the fibrous F1 protein forms heterogeneous aggregates that might compromise the quality of the vaccines and lead to variable and insufficient immune responses.[21,23,24]

Previously, researchers tried to use a mixture of F1, V, and PA antigens. However, the same immunized animals have not been tested for protection against both anthrax and plague pathogens. Another major problem in developing these biodefense vaccines is the need for two separate vaccines requiring two completely different manufacturing processes. For national preparedness against potential bioterror threats, it would be highly beneficial to design a multivalent vaccine that can provide protection against both of pathogens, *B. anthracis* and *Y. pestis*. Such a vaccine would require a single manufacturing process, fewer immunizations, and would be cost-effective. It would also greatly reduce time and effort in expensive human clinical trials and the downstream licensing and other regulatory processes. Furthermore, and perhaps most significant, it would streamline the systems for stockpiling, field delivery, and mass vaccination of humans.

Recently, the present inventors reported two new approaches to overcome some of the problems associated with the recombinant anthrax and plague vaccines.[23,25] Using structure-based immunogen design, a mutant (mut) F1 which folds into a soluble monomer rather than a fiber, without diminishing its immunogenicity, is engineered.[23,25] The monomeric F1 in combination with V (F1mutV fusion protein; 56 kDa) provided complete protection against highly lethal *Y. pestis* CO92 challenge in mice and Brown Norway rat models of pneumonic plague.[23] In parallel, a novel nanoparticle antigen display and delivery system using bacteriophage T4 is developed.[23,25-27] The 120×86 nm size T4 head (capsid) is decorated with 870 molecules of the nonessential small outer capsid protein or Soc (9 kDa).[28] Soc assembles as a trimer and clamps adjacent capsomers (a molecular clamp), reinforcing and further stabilizing an already stable T4 head.[29] PA (or F1mutV) fused to the N- or C-termini of Soc can be displayed on Soc-T4 head with high affinity and exquisite specificity.[23,25,27,30] Such nanoparticles arrayed with the antigen molecules using our defined in vitro assembly system are highly immunogenic.[23,31] These particles elicited a robust immune response in the absence of an adjuvant[23,31,32] and provided complete protection against lethal inhalational anthrax or pneumonic plague challenges in multiple animal models.[23,32]

Embodiments disclosed herein provide two approaches to design a single biodefense vaccine against inhalation anthrax and pneumonic plague. Generally, the first approach involves engineering a bivalent immunogenic composition comprising a fusion protein. The fusion protein is a triple antigen containing all three antigens, i.e., F1 and V from *Y. pestis* and PA from *B. anthracis* that is able to fold into a soluble protein and retain full functionality. For example, this fusion protein may be constructed by recombinantly fusing all three genes for mutated F1,[26] V,[21] and PA[28]. The fusion protein requires a single process for vaccine manufacture. The second approach involves preparation of bacteriophage nanoparticles arrayed with all three antigens, i.e., F1 and V from *Y. pestis* and PA from *B. anthracis* that is able to fold into a soluble protein and retain full functionality. For example, a single vaccine may comprise T4 bacteriophage (or T4 phage) nanoparticles that display these three immunogens on the virus surface of the T4 phage nanoparticles. The bacteriophage nanoparticles arrayed with all three antigens may be used as a vaccine without adjuvant.

Both the vaccines disclosed herein have been demonstrated to provide protection against sequential or simultaneous challenge with both anthrax and plague pathogens. For example, both the soluble triple fusion and T4 nanoparticle vaccines generate robust antigen-specific immune responses and provided near complete protection against anthrax and plague in three different animal models. Furthermore, the T4 nanoparticles generate balanced $T_H1$- and $T_H2$-based antibody responses, a highly desirable trait for any vaccine, but particularly important for protection against plague.[11] By using a dual challenge model in which the animals are simultaneously administered with lethal doses of both anthrax lethal toxin (LeTx) and *Y. pestis* CO92, the disclosed vaccines provide complete protection against anthrax and plague. For example, in some embodiment, two doses of these disclosed vaccines elicit robust immune responses in mice, rats, and rabbits, and confer complete protection in animal models of inhalational anthrax and pneumonic plague.

The present disclosure provides the first proof-of-concept data that a dual anthrax-plague vaccine can potentially protect vaccinees in the event of a bioterror attack with weaponized *B. anthracis* and/or *Y. pestis*. These dual vaccines (bivalent vaccine), therefore, are strong candidates for stockpiling as part of national preparedness against bioterrorism threats.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

Bivalent Immunogenic Composition Comprising a Triple Fusion Protein

FIG. 2A is a schematic illustrating protective antigen (PA) and F1mutV-PA recombinant constructs according to one embodiment of the present invention. As shown in FIG. 2A, PA (83 kDA) 210 comprises multiple domains including PA20 domain 220, PA63 domain 230, and PA domain IV 240. Furin cleavage site shown as an arrow locates between the PA20 domain 220 and the PA63 domain 230. The Furin cleavage site Generally, the first approach involves engineering a bivalent (or dual) immunogenic composition comprising a triple fusion protein These three antigens are able to fold into a soluble protein and retain full functionality.

In one embodiment, a triple fusion protein containing all three antigens, i.e., F1 and V from *Y. pestis* and PA from *B. anthracis*, is constructed by recombinantly fusing all three genes for mutated F1,[26] V,[21] and PA[28] in-frame. The goal is to retain the structural and functional integrity of all three antigens so that each antigen's immunogenicity and protective efficacy is not compromised. As a result, each antigen comprised in the triple fusion protein keeps its immunogenicity and protective efficacy. This triple fusion protein may be used as an immunogenic component to create a dual anthrax-plague vaccine, or bivalent anthrax-plague vaccine.

F1mutV-PA shown in FIG. 2A is an exemplary triple fusion protein comprising a mutated F1 and a V antigen from *Yersinia pestis* and a protective antigen (PA) from *B. anthracis* fused in-frame. The mutated F1 is fused in-frame to the N-terminus of the V antigen via a first linker, and the V antigen is fused in-frame to the N-terminus of PA via a second linker. The triple fusion protein has immunogenicity of the mutated F1, immunogenicity of the V antigen, and immunogenicity of the PA. Fusion protein F1mutV-PA is able to be cleaved by furin, resulting in cleavage products, of which one is F1mutV-PA20 280 and another one is PA63 domain 230 with PA domain IV 240. The furin cleavage site at PA residues comprises RKKR (SEQ ID NO: 7).

In one embodiment, in the above described triple fusion protein, the C-terminus of a previously constructed F1mutV (56 kDa) antigen 270[23,25] is fused to the N-terminus of PA (83 kDa) with a flexible linker in the middle. In one embodiment, the flexible linker comprises Glu-Ala-Ser-Ala (SEQ ID NO: 12). In one embodiment, the F1mut shown in FIG. 2A is previously designed by deleting the N-terminal β-strand residues 1-14 of native F1 antigen and fusing them to the C-terminus of native F1 antigen with a linker, such as a Ser-Ala linker, in between. Consequently, the β-strand is reoriented such that it fits into its own β-sheet cleft (intramolecular complementation) rather than that of the adjacent F1 subunit. In addition, residues 15-21 of native F1 are duplicated at the C-terminal end to restore any potential T-cell epitope that might have been compromised during the β-strand switch. As a result, F1mut folds into a monomer instead of polymerizing as a linear fiber and retains full immunogenicity.[26, 29]

In one embodiment, the F1mut has a polypeptide sequence set forth in SEQ ID NO: 1. The V antigen and PA sequences of the triple antigen correspond to native full-length sequences.[21, 28] The V antigen has a polypeptide sequence set forth in SEQ ID NO: 2 and PA has a polypeptide sequence set forth in SEQ ID NO: 3. In one embodiment, the triple fusion protein F1mutV-PA comprises a sequence set forth in SEQ ID NO: 4.

Figure 2B:
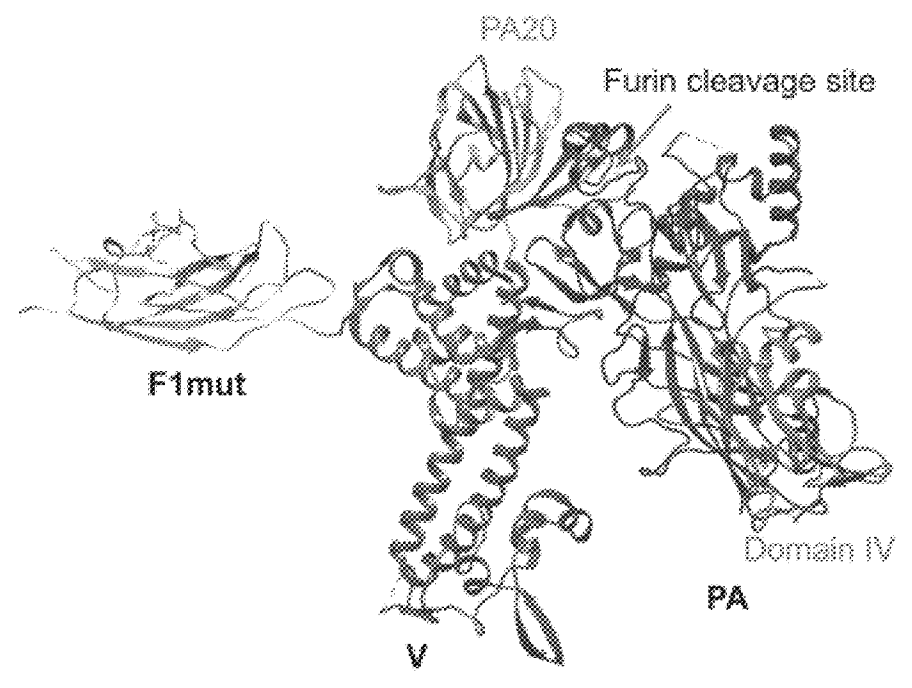

FIG. 2B is a structural model of F1mutV-PA triple antigen according to one embodiment of the present invention. The model is manually generated using Chimera with structures of V antigen (PDB ID: 1Z9S), V antigen (PDB ID: 4JBU), and PA (PDB ID: 1ACC). Based on structural and bioinformatics analyses, this orientation is predicted to be optimal because the C-terminal PA domain IV, which recognizes the host receptors CMG2 (capillary morphogenesis gene-2) and TEM8 (tumor endothelial marker-8), will encounter minimal, if any, steric hindrance.[30,31]

Recognition of these receptors is the first step in the anthrax toxin intoxication pathway within the host cell and essential for furin cleavage of the N-terminal domain of PA to generate PA20 (20 kDa) and PA63 (63 kDa) (FIG. 1A and FIG. 1B).[35] PA63 oligomerizes to produce heptamers and octamers that then interacts with lethal factor (LF) and edema factor (EF) (FIG. 1A).[13] Although in the construct the F1mutV protein is attached to the N-terminus of PA (FIG. 2A), based on the linear domain arrangement of F1 and V proteins as determined by the X-ray structures,[55,56] the furin cleavage site at PA residues RKKR (SEQ ID NO: 7 (amino acids (aa) 164-167) should remain accessible to the protease (FIG. 2B).

Embodiments further provide various vectors for expression the triple fusion protein described above. A vector may have a regulatory region operably linked to a nucleic acid sequence encoding the triple fusion protein described above. The regulatory region regulates the expression of the triple fusion protein in a cell carrying the vector. In some embodiment, the expression of the recombinant is regulated under a regulatory region comprising an inducible promoter, and the triple fusion protein is not consistently expressed in a cell carrying the vector but can be induced as needed. In some embodiment, the expression of a recombinant protein described herein in a cell carrying the vector is controlled under a constitutively promoter.

In some embodiment, bivalent (dual) anthrax-plague vaccine may be developed from the above described triple fusion protein. An immunogenic composition may comprise the above described triple fusion protein containing all three antigens, i.e., F1 and V from *Y. pestis* and PA from *B. anthracis*, fused in frame. For example, an immunogenic composition my include F1mutV-PA (SEQ ID NO: 4) as immunogenic component. An immunogenic composition comprising a triple fusion protein such as F1mutV-PA (SEQ ID NO: 4) may further include a pharmaceutical acceptable carrier or excipient. Alternatively, an immunogenic composition comprising a triple fusion protein such as F1mutV-PA (SEQ ID NO: 4) may further include an adjuvant and be used as a vaccine to provide protection against sequential or simultaneous challenge with both anthrax and plague pathogens. In some embodiment, the tripe fusion protein F1mutV-PA can be adjuvanted with Alum or another licensed adjuvant using the already established processes in vaccine manufacturing. F1mutV-PA may be adjuvanted with liposomes or Alum-liposomes mixture.

In some embodiments, the triple fusion protein contained in the immunogenic composition is purified. One skilled in the art of preparing formulations can readily select the proper form and mode of administration depending upon the particular characteristics of the vaccine selected, the disorder or condition to be treated, the stage of the disorder or condition, and other relevant circumstances.

Figures 10A, 10B:
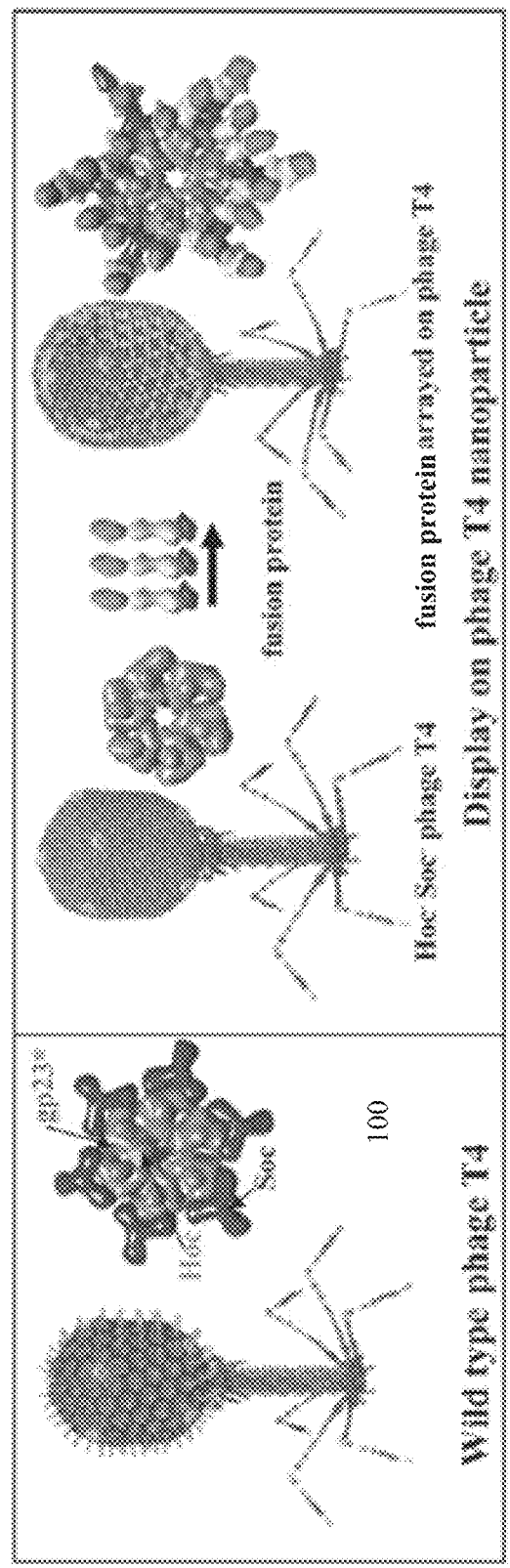
FIG. 10A is a structural model of a bacteriophage T4.
FIG. 10B shows display of a fusion protein on a Hoc-Soc-T4 bacteriophage particle via Soc from a T4 phage or a T4-related bacteriophage according to one embodiment of the present invention.

Bivalent Vaccine Comprising Bacteriophage Nanoparticles Arrayed with Three Antigens FIG. 10A is a structural model of a bacteriophage T4. The enlarged capsomer 1000 shows a major capsid protein gp23* ("*" represents a cleaved form) (930 copies), Soc (870 copies), and Hoc (155 copies). The portal vertex (not visible in the picture) connects the head to the tail. The unique architecture of bacteriophage T4 capsid (T (triangulation number)=20; width, 86 nm; length, 119.5 nm) with two non-essential outer capsid proteins, Hoc (highly antigenic outer capsid protein; 39 kDa) and Soc (small outer capsid protein; 9 kDa), provides a suitable platform for multicomponent antigen display. Hoc and Soc decorate the capsid, which is composed of the major capsid protein, gp23* ("*" represents the cleaved mature capsid protein) (49 kDa, 930 copies), the vertex protein, gp24* (46 kDa, 55 copies), and the portal protein, gp20 (61 kDa, 12 copies). Hoc, a dumbbell shaped protrusion at the center of the gp23* hexon, is a monomer present at up to 155 copies per capsid, whereas Soc, a small protrusion at the interface of adjacent hexons, is a trimer present at up to 810 copies per capsid. These proteins bind to the capsid sites, which appear after maturation cleavages of the capsid proteins and capsid expansion. These proteins, especially Soc, stabilize the capsid against extremes of pH (>10.5), but are not required for phage viability or infectivity.[30]

FIG. 10B shows display of a fusion protein on a Hoc-Soc-T4 bacteriophage particle via Soc from a T4 phage or a T4-related bacteriophage. Enlarged capsomers show models of capsomes before and after the fusion protein display. Upon binding of a fusion protein, such as a Soc fusion protein, the T4 phage particle is decorated with the fusion protein and displays the fusion protein on its capsid.

According to embodiments, an immunogenic composition may comprise one or more bacteriophage nanoparticles arrayed with one or more Soc fusion proteins on capsid surface of each bacteriophage nanoparticle. The one or more Soc fusion proteins may comprise a Soc fused to an antigen selected from the group consisting of a mutated F1 antigen from *Yersinia pestis*, a V antigen from *Yersinia pestis*, a protective antigen (PA) from *B. anthracis*, and combination thereof. The bacteriophage nanoparticles may be a T4 phage or a relative of T4 phage. The Soc may be from T4 bacteriophage or a relative of T4 bacteriophage such as phage RB49.

Soc fusion proteins may be constructed by fusing a small outer capsid protein of a bacteriophage T4 or a T4-related phage to an antigen via a linker. In some embodiments, the small outer capsid protein of a T4phage or a T4-related phage may be Soc from T4 phage or from T4-related bacteriophage RB69. As shown in FIGS. 10A and 10B, the small outer capsid protein of a bacteriophage T4 or a T4-related phage provides a nanoplatform for symmetrical arraying of the antigen on the surface of a bacteriophage T4 or a T4-related phage as a fusion protein.

In some embodiments, an antigen may be fused to a Soc protein from a T4 phage or a T4-related phage RB69 via a linker. In some embodiment, the linker may be a two amino acid linker Gly-Ser.

In some embodiment, the above described Soc protein may be a Soc fusion protein encompassing mutated F1 antigen from *Yersinia pestis*, V antigen from *Yersinia pestis*, and/or PA from *B. anthracis*. In some embodiments, a mutated antigen such as mutated F1 antigen may be fused to a Soc protein from a T4 phage or a T4-related phage RB69 via a linker. For example, a Soc protein may be a T4-related phage RB69 Soc having an amino acid sequence set forth in SEQ ID NO: 15. The Soc protein may be encoded by a nucleotide sequence of SEQ ID NO: 16. The linker used for fusing a Soc protein with an antigen such as a mutated F1 may comprise a two amino acid linker Gly-Ser.

Specifically, embodiments further provide recombinant proteins constructed by fusing mutated F1 antigen, V antigen, and PA with RB49 Soc in-frame. In one embodiment, these Soc fusion proteins include F1mutV-Soc-PA (148 kDa), F1mutV-Soc (66 kDa), Soc-PA (93 kDa), etc.

In one embodiment, the above described immunogenic composition comprises a Soc fusion protein which is a recombinant protein F1mutV-Soc-PA. The recombinant protein F1mutV-Soc-PA including a mutated F1 antigen and a V antigen from *Yersinia pestis*, a Soc, and a PA. The mutated F1 antigen is fused in-frame to the N-terminus of the V antigen, the V antigen is fused in-frame to N-terminus of the Soc, and the Soc is fused in-frame to the N-terminus of PA. In one embodiment, fusion protein F1mutV-Soc-PA has an amino acid sequence set forth in SEQ ID NO: 18. In one embodiment, the fusion protein F1mutV-Soc-PA is encoded by a nucleotide sequence set forth in SEQ ID NO: 17. In one embodiment, each bacteriophage nanoparticle of the one or more bacteriophage nanoparticles described above is arrayed with the recombinant protein F1mutV-Soc-PA on capsid surface.

The recombinant protein F1mutV-Soc including a mutated F1 antigen, a V antigen, and a Soc. The mutated F1 antigen is fused in-frame to the N-terminus of V antigen to thereby and the V antigen is fused in-frame to the N-terminus of the Soc. Soc fusion protein Soc-PA comprise a Soc fused in-frame to the N-terminus of PA. The Soc protein described above may be from a T4 phage or a T4-related bactgeriophage such as RB69. Various peptide linkers may be used in constructing the various Soc fusion proteins.

In some embodiments of the present invention, a native V antigen of *Yersinia pestis* is fused to a Soc protein from a T4 phage and/or a T4-related bactgeriophage RB69 via a linker, resulting a recombinant protein V-Soc. A two amino acid linker Gly-Ser may be used between V antigen and Soc, wherein a C-terminus of the linker is directly linked to an NH2-terminus of the Soc protein from a T4 phage and/or a T4-related bacteriophage RB69 and an NH2-terminus of the linker is directly linked to a C-terminus of the V antigen of *Yersinia pestis*.

In one embodiment of the present invention, the above described Soc fusion protein may be expressed in cells, including and bacteria *E. Coli* cells, and be purified from cell-free lysates of cell cultures. The purified Soc fusion proteins may be then arrayed on the capsid surface of a bacteriophage nanoparticle.

The above described recombinant proteins, for example, F1mutV-Soc-PA, F1mutV-Soc, and Soc-PA, may be assembled on one or more T4 nanoparticles through three different ways: i) display of F1mutV-Soc-PA on the capsid surface of a T4 nanoparticle, ii) display of F1mutVSoc and Soc-PA on the same capsid surface of a T4 nanoparticle, and iii) a 1:1 mixture of T4 phage particles separately displayed with F1mutV-Soc or Soc-PA.

Accordingly, in one embodiment, the Soc fusion proteins, i.e., F1mutV-Soc and the Soc-PA are arrayed on the same capsid of bacteriophage nanoparticle. In one embodiment, the above described Soc fusion proteins F1mutV-Soc and Soc-PA are separately arrayed on different capsid of bacteriophage nanoparticle, and the immunogenic composition comprises a 1:1 mixture of bacteriophage nanoparticles separately displaying F1mutV-Soc and Soc-PA.

In some embodiment, bivalent (dual) anthrax-plague vaccine may be developed from the above described bacteriophage nanoparticles arrayed with above described Soc fusion proteins. In some embodiments, an immunization dosage of an immunogenic composition comprising one or more bacteriophage nanoparticles arrayed with one or more above described Soc fusion proteins on capsid surface of each of the one or more bacteriophage nanoparticles is administered to a subject in need thereof. The one or more Soc fusion proteins may be a Soc fused to an antigen selected from the group consisting of a mutated F1 antigen from *Yersinia pestis*, a V antigen from *Yersinia pestis*, a protective antigen (PA) from *B. anthracis*, and/or a combination thereof. The bacteriophage nanoparticles arrayed with all three antigens may be administered to a subject without adjuvant. The immunogenic composition is able to elicit immune response in the subject against anthrax and plague pathogens.

Vaccination

An immunization dosage of immunogenic compositions described above may be administered to a subject in need thereof by a variety of routes. For example, an immunization dosage of the immunogenic composition may be administered to a subject via parenteral routes. An immunization dosage of the immunogenic composition may be administered to a subject via intranasal route. An immunization dosage of the immunogenic composition may be administered to a subject subcutaneous injection, intramuscular injection, intravenous injection, inhalation, transdermal routes, or other routes. The immunogenic composition may be further administered to a subject twice during a period of time. A subject receiving the above described immunogenic composition may be a human and a non-human animal, such as mouse, rat, rabbit, nonhuman primate, etc.

In determining an effective amount, the dose of a vaccine, a number of factors are considered by the attending diagnostician, including, but not limited to: the type of a vaccine to be administered; the subject's weight, age, and general health; the response of the individual subject; the mode of administration; the dose regimen selected; the use of other concomitant medication; and other relevant circumstances.

The specific dose administered may be determined by particular circumstances surrounding each situation. These circumstances can include: the route of administration, the prior medical history of the recipient, the symptom being treated, the severity of the symptom being treated, and the age of the recipient. The recipient subject's attending physician should determine the therapeutic dose administered in light of the relevant circumstances.

All documents, patents, journal articles and other materials cited in the present application are incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The disclosed invention is further defined in the following Examples. It should be understood that these Examples are given by way of illustration only. From the above discussion and these Examples, one skilled in the art can ascertain the essential characteristics of embodiments of the disclosed invention. Without departing from the spirit and scope thereof, one skilled in the art can make various changes and modifications of the invention to adapt it to various usages and conditions. All publications, including patents and non-patent literature, referred to in this specification are expressly incorporated by reference herein.

EXAMPLES

Example 1

Construction of an Anthrax-Plague Triple Antigen

To create a bivalent anthrax-plague vaccine, we fused in-frame the coding sequences corresponding to F1mut antigen (SEQ ID NO: 1), V antigen (SEQ ID NO: 2), and PA (SEQ ID NO: 3) are fused in-frame as shown in FIG. 2A, resulting in F1mutV-PA triple antigen (SEQ ID NO: 4). As an example, the coding sequence for F1mutV is set forth in SEQ ID NO: 5, and the coding sequence for PA is set forth in SEQ ID NO: 6.

Figure 11:
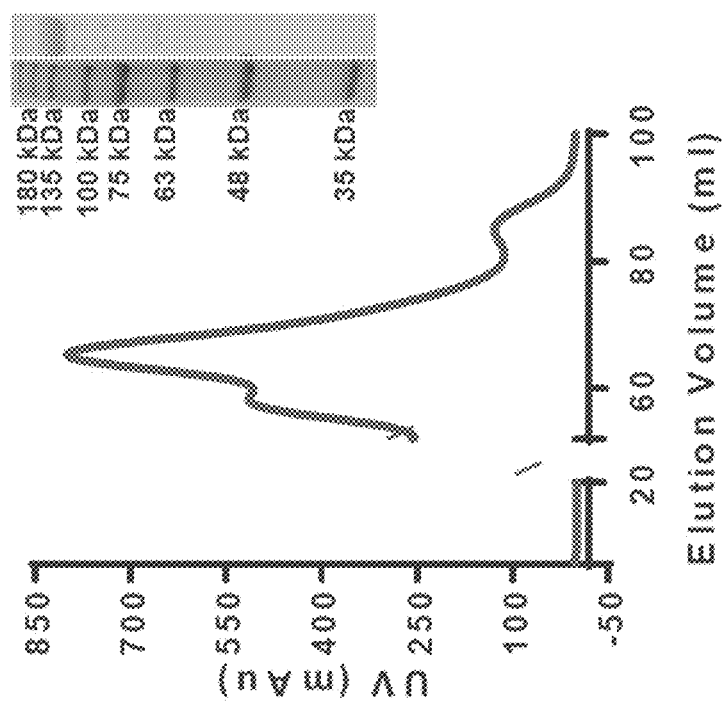
FIG. 11 is a graph showing purification of F1mut1-PA according to one embodiment of the present invention.

The F1mutV-PA protein (SEQ ID NO: 4) was expressed in *Escherichia coli* BL21-codon plus (DE3)-RIPL cells and purified from the soluble fraction at the yield of 5-10 mg/L. Remarkably, the 139 kDa F1mutV-PA protein consisting of seven domains belonging to three different proteins (FIG. 2B) was soluble and existed mainly as a monomer in solution as determined from the elution profile following size-exclusion chromatography (FIG. 11). FIG. 11 is a graph showing purification of F1mut1-PA according to one embodiment of the present invention. Elution profile of F1mut1-V by size-exclusion chromatography on a Hi-load 16/60 Superdex 200 column. The inset shows the purity of F1mut1-PA as analyzed by SDS-PAGE and Coomassie blue staining of the pooled peak fractions.

Figures 2C, 2D, 2E:
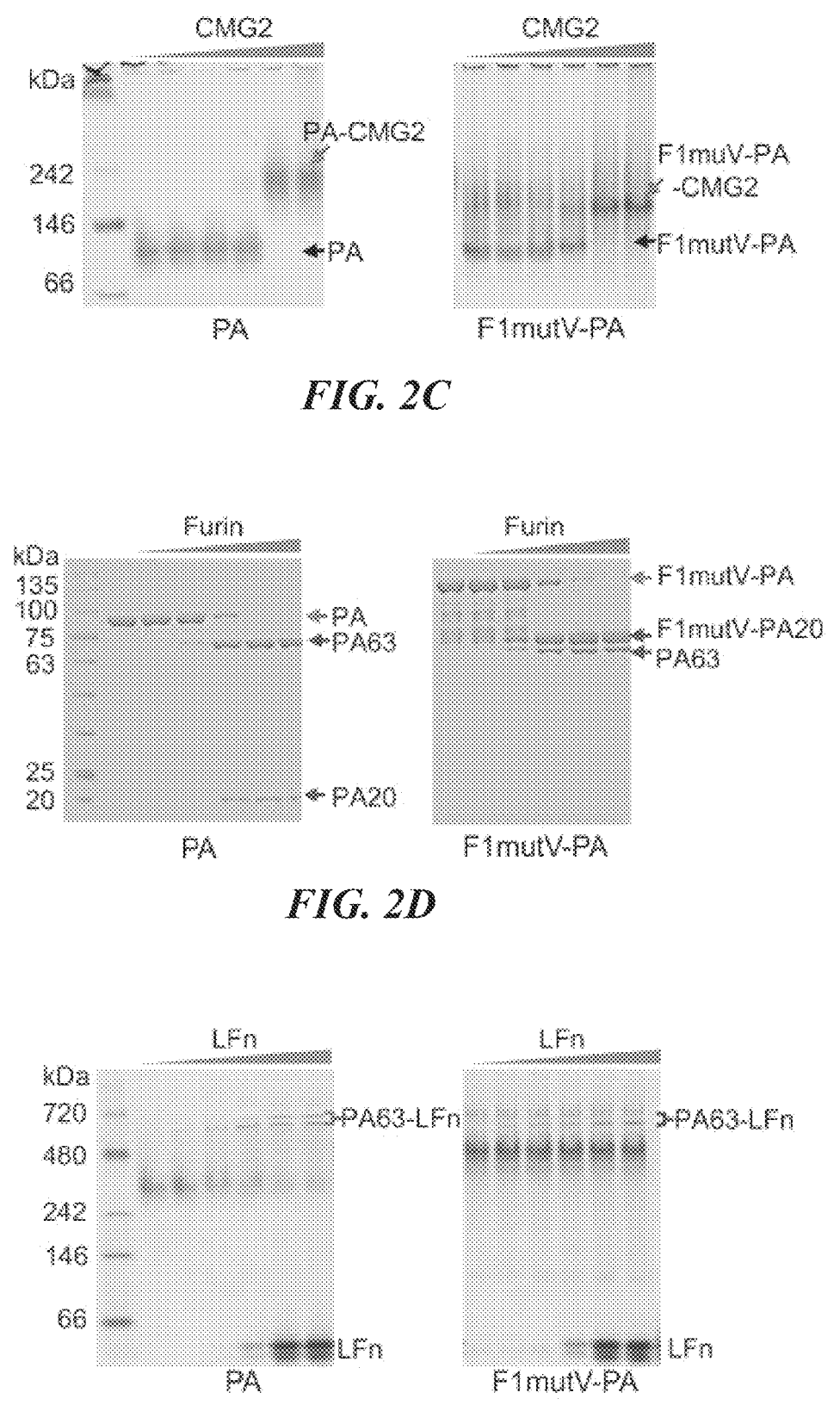

A series of quantitative biochemical analyses were performed to verify the functionality of F1mutV-PA. FIG. 2C illustrates the binding of F1mutV-PA to PA receptor, CMG2, according to one embodiment of the present invention. The PA or F1mutV-PA proteins were incubated with increasing amounts of CMG2 and interactions between the PA proteins and CMG2 were analyzed by Native-PAGE. PA-CMG2 and F1mutV-PA-CMG2 complexes are marked with light arrows. PA-CMG2 and F1mutV-PA-CMG2 complexes are marked with light arrows. PA and F1mutV-PA are marked with black arrows. FIG. 2D illustrates furin cleavage of F1mutV-PA according to one embodiment of the present invention. The recombinant PA or F1mutV-PA proteins were treated with increasing amounts of furin and cleavage products were analyzed by SDS-PAGE and Coomassie blue staining. Positions of the PA and F1mutV-PA bands are marked with light arrows and the positions of the PA63, PA20, and F1mutV-PA20 bands are marked with dark arrows. FIG. 2E illustrates the binding of F1mutV-PA to N-terminal domain of lethal factor (LFn) according to one embodiment of the present invention. The PA and F1mutV-PA proteins were first treated with furin to release PA63 and then incubated with increasing amounts of LFn. Interactions between the PA63 heptamer/octamer and LFn were analyzed by Native-PAGE. The PA63-LFn complexes are marked with braces. The SDS-PAGE and native gels were stained with Coomassie blue R-250 and Coomassie blue G-250, respectively.

First, as shown in FIG. 2C, F1mutV-PA bound to the soluble external domain of CMG2 equivalently as the rPA at different ratios of F1mutV-PA:CMG2, generating a high-molecular weight (MW) complex (FIG. 2C, light arrows). Second, as shown in FIG. 2D, F1mut-PA and rPA had similar sensitivity to various concentrations of furin. Whereas rPA is cleaved to PA63 and PA20, F1mutV-PA is cleaved to 76 kDa F1mutV-PA20 and PA63. Third, as shown in FIG. 2E, as in the case of the rPA, the PA63 generated by cleavage of F1mutV-PA bound to LFn (N-terminal PA-binding domain of LF), resulting in the formation of PA63-LFn complexes. Collectively, these results demonstrated that the biochemical properties of the fusion protein F1mutV-PA remained similar to rPA.

Example 2

Display of T4phage Nanoparticles with F1mut-V and PA

The 120×86 nm bacteriophage T4 capsid provides a nanoplatform for symmetrical arraying of antigens on the surface as fusion proteins of the capsid protein, Soc. Previous studies showed that antigens fused to phage RB49 Soc (a close relative of T4 phage) are more soluble than the same fused to T4 Soc and could be efficiently displayed on the capsid.[23] In this example, three recombinants using the RB49 Soc were constructed: F1mutV-Soc-PA (148 kDa), F1mutV-Soc (66 kDa), and Soc-PA (93 kDa). These three recombinants were assembled on T4 nanoparticles in three different ways: i) display of F1mutV-Soc-PA, ii) display of F1mutVSoc and Soc-PA on the same capsid, and iii) a 1:1 mixture of T4 phage particles separately displayed with F1mutV-Soc or Soc-PA. Of these, the latter produced particles with the highest copy number of the antigens per capsid whereas F1mutV-Soc-PA produced particles with the least copy number (data not shown). Hence this formulation, T4-F1mutV-Soc/Soc-PA (abbreviated as T4-F1mutV/PA) was used for all immunization experiments (see below) disclosed herein.

Figure 12:
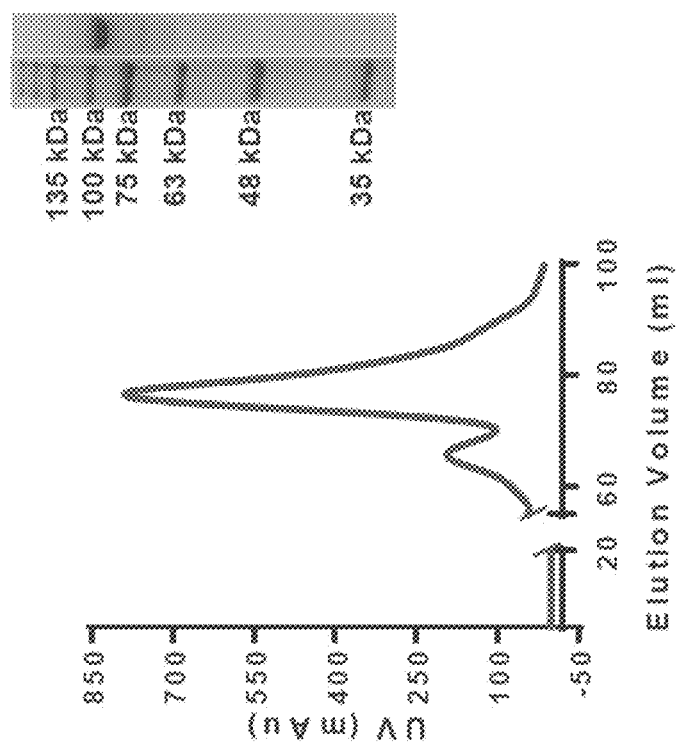
FIG. 12 is a graph showing purification of Soc-PA according to one embodiment of the present invention.

FIG. 12 is a graph showing purification of Soc-PA according to one embodiment of the present invention. The Soc-PA recombinant protein was purified from the cell-free lysates by HisTrap affinity chromatography followed by Hiload 16/60 Superdex 200 gel filtration. The inset shows the purity of Soc-PA after SDSPAGE and Coomassie blue staining of the pooled peak fractions.

Figure 5B:
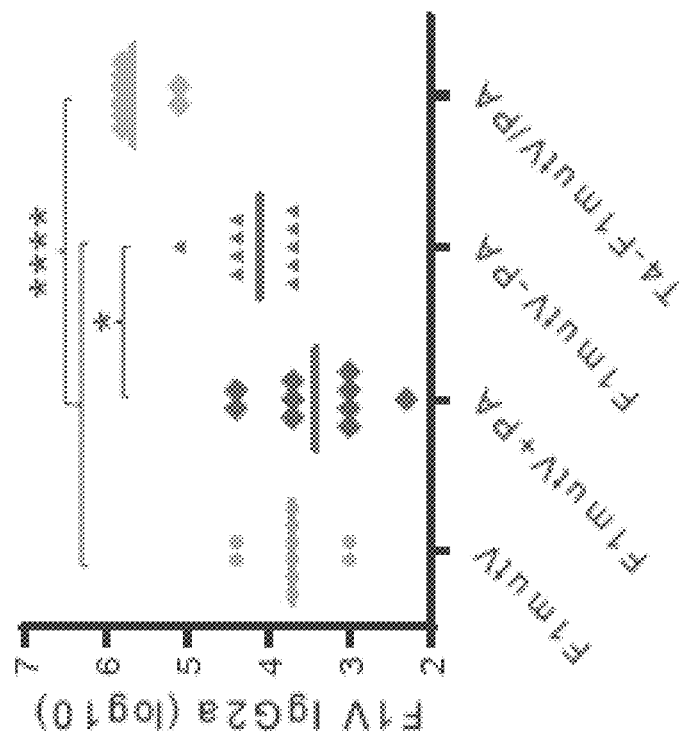
FIG. 5B is a graph illustrating F1V-specific IgG2a antibody titers elicited by F1mutV-protective antigen (PA) triple antigen and T4-F1mutV/PA in mice according to one embodiment of the present invention.
Figure 5A:
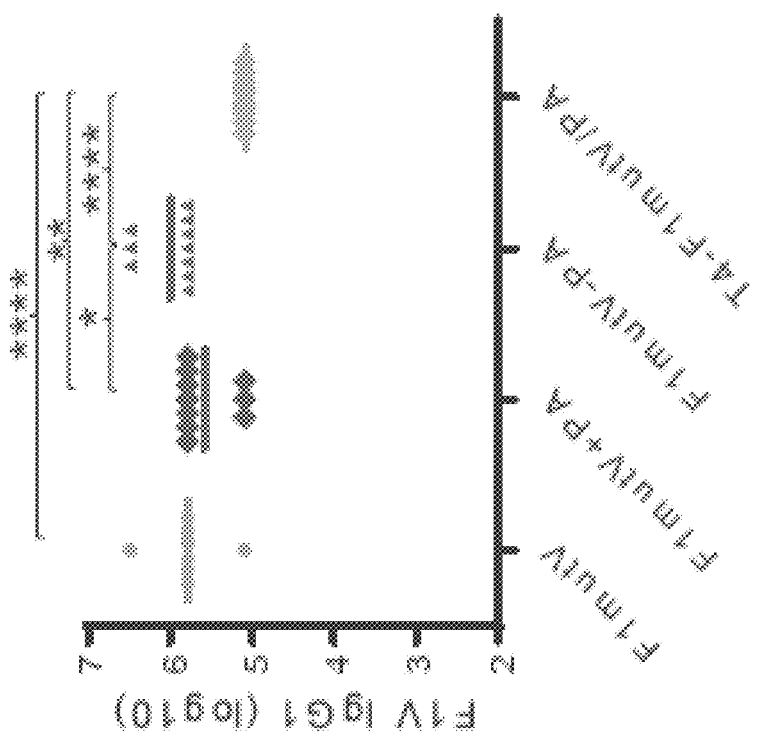
FIG. 5A is a graph illustrating F1V-specific IgG1 antibody titers elicited by F1mutV-protective antigen (PA) triple antigen and T4-F1mutV/PA in mice according to one embodiment of the present invention.
Figure 5C:
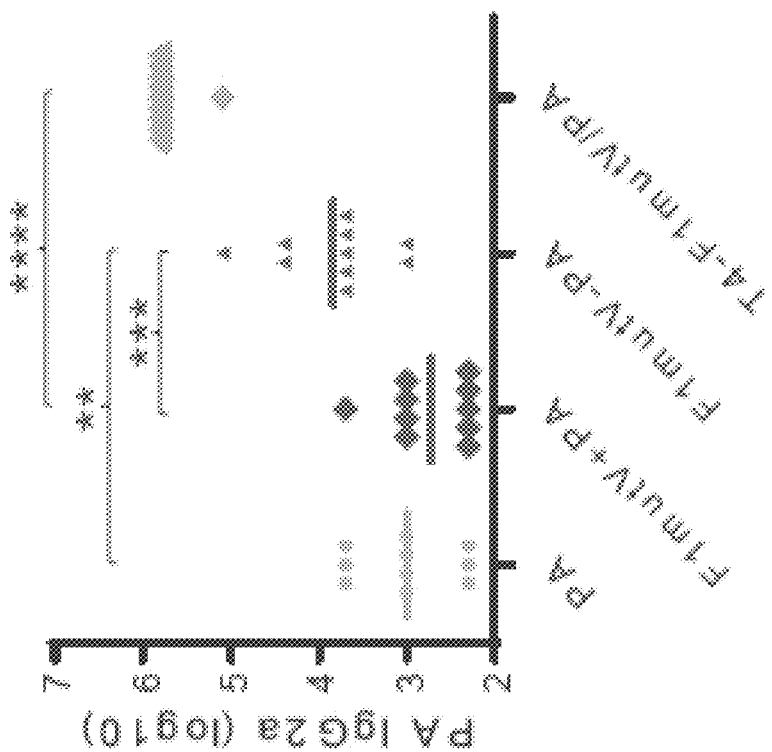
FIG. 5C is a graph illustrating PA-specific IgG1 antibody titers elicited by F1mutV-protective antigen (PA) triple antigen and T4-F1mutV/PA in mice according to one embodiment of the present invention.
Figure 5D:
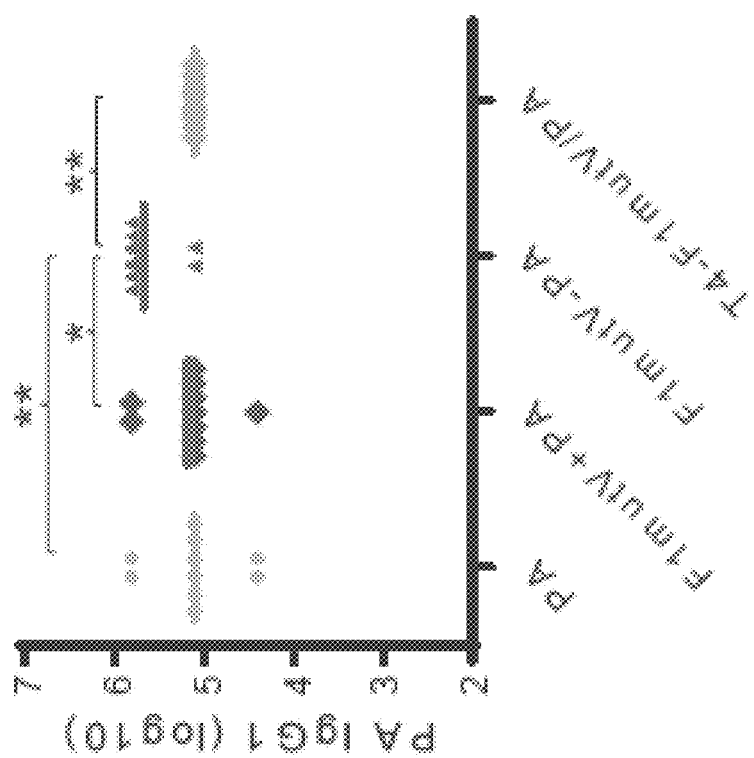
FIG. 5D is a graph illustrating PA-specific IgG2a antibody titers elicited by F1mutV-protective antigen (PA) triple antigen and T4-F1mutV/PA in mice according to one embodiment of the present invention.

FIGS. 3A, 3B, 3C, and 3D illustrate the display of F1mutV-Soc and Soc-PA on Hoc-Soc-T4 phage according to one embodiment of the present invention. Approximately 2×10$^{10}$ Hoc-Soc-T4 phage particles were incubated at the indicated ratios of F1mutV-Soc or Soc-PA molecules to capsid binding sites. The control lane is the Hoc-Soc-phage used in the experiment. F1mutV-Soc (FIG. 3A) and Soc-PA (FIG. 3B) bands, which are not present in the phage control, are labeled with light arrows. FIG. 3C and FIG. 3D show saturation binding curves of F1mutV-Soc (FIG. 3C) and Soc-PA (FIG. 3D). The density volumes of bound F1mutV-Soc (FIG. 3A) and Soc-PA (FIG. 3B) from SDS-PAGE were determined by laser densitometry and normalized to that of gp23* present in the respective lane. The unbound F1mutV-Soc and Soc-PA were quantified in separate gels. The copy numbers were determined in reference to gp23* (930 copies per capsid). The data were plotted as one site saturation ligand binding curve and the calculated binding parameters are shown. Kd, apparent binding constant; $B_{max}$, maximum copy number per phage particle.

To optimize the copy number for immunization experiments, the cesium chloride (CsCl) gradient-purified Hoc-Soc-phage particles were incubated with the purified F1mutV-Soc or Soc-PA proteins at different ratios of antigen molecules to Soc binding sites (FIGS. 3A, 3B, 3C, and 3D). Binding increased with increasing ratio, reaching saturation at ~20:1 (FIGS. 3A and 3B). The copy number of antigens displayed per capsid ($B_{max}$) is 657 for the 66-kDa F1mutV-Soc and 370 for the 93-kDa Soc-PA, and the apparent binding constants ($K_d$) were 298 nM and 737 nM, respectively (FIGS. 3C and 3D). Since there are 870 Soc binding sites per capsid, the percent occupancy is 75% for F1mutV-Soc and 42% for Soc-PA. These represent high occupancy considering that the large size of the antigens is expected to cause some steric hindrance that prevents saturation of the Soc binding sites.

Example 3

The Soluble and T4 Nanoparticle Anthrax-Plague Dual Vaccines are Highly Immunogenic in Mice FIGS. 4A through 4E show that the F1mutV-protective antigen (PA) triple antigen and T4nanoparticle anthrax-plague dual vaccine T4-F1mutV/PA are highly immunogenic in mice according to embodiments of the present invention. FIG. 4A shows vaccine formulations used in various immunized mouse groups according to one embodiment. The protein combinations used for each group are shown. FIG. 4B illustrates the immunization scheme according to one embodiment. In this embodiment, Mice (n=10) were immunized (intramuscular) on days 0 and 21. Sera were collected on days 0 and 35 for antibody analysis. Animals were challenged with lethal toxin (LeTx) on day 42 followed by *Yersinia pestis* CO92 on day 75. FIG. 4C is a graph illustrating F1V-specific antibody titers according to one embodiment. FIG. 4D is a graph showing PA-specific antibody titers according to one embodiment. FIG. 4E is a graph showing LeTx-neutralizing antibody titers according to one embodiment. Error bars represent SD. "*," "*," and "**" denote $p<0.05$, $p<0.001$, and $p<0.0001$, respectively (ANOVA).

As shown in FIG. 4A, in this example, Balb/c mice (n=10/group) were immunized by the intramuscular (i.m.) route with equivalent amounts (25 μg) of soluble (F1mutV-PA) or T4 nanoparticle displayed (T4-F1mutV/PA) immunogens and were boosted once on day 21. Mice immunized with PA alone, F1mutV alone, or a mixture of F1mutV and PA (F1mutV+PA) served as control groups (FIG. 4A and FIG. 4B). The latter group allowed assessment of our dual vaccine formulations relative to a simple mixture of the two antigens.

All of the F1mutV immunogens elicited high and comparable levels of F1mutV specific IgG antibodies, up to an end point titer of $\sim3\times10^6$ (FIG. 4C). The PA antigens similarly elicited high antibody titers; however, significant differences were observed among the groups (FIG. 4D). The T4-displayed F1mutV/PA induced the highest PA-specific IgG titers followed by F1mutV-PA ($p<0.001$). Both these antigens induced significantly higher titers than did PA alone or F1mutV+PA (FIG. 4D). The naïve animals, as expected, showed no antibodies to either PA or F1mutV (FIGS. 3D and 4D). Similarly, the animals immunized with PA alone had no F1mutV-specific antibodies and vice-a-versa (FIGS. 3D and 4D).

A toxin neutralization assay (TNA) was performed to determine LeTx neutralizing activity by anti-PA antibodies present in the sera of the immunized mice. Previous studies demonstrated that the levels of LeTx neutralizing antibodies correlated with protection against inhalational *B. anthracis* challenge.[36] All of the groups immunized with the PA antigen demonstrated strong LeTx neutralization titers (FIG. 4E). The naïve animals (PBS group) or the F1mutV-immunized animals, as expected, were negative for toxin neutralization.

FIGS. 5A through 5D illustrates subtype specificity of antibodies elicited by F1mutV-protective antigen (PA) triple antigen and T4nanoparticle anthrax-plague dual vaccine T4-F1mutV/PA in mice, according to one embodiment of the present invention. FIG. 5A is a graph illustrating F1V-specific IgG1 antibody titers elicited by F1mutV-protective antigen (PA) triple antigen and T4-F1mutV/PA in mice. FIG. 5B is a graph illustrating F1V-specific IgG2a antibody titers elicited by F1mutV-protective antigen (PA) triple antigen and T4-F1mutV/PA in mice. FIG. 5C is a graph illustrating PA-specific IgG1 antibody titers elicited by F1mutV-protective antigen (PA) triple antigen and T4-F1mutV/PA in mice. FIG. 5D is a graph illustrating PA-specific IgG2a antibody titers elicited by F1mutV-protective antigen (PA) triple antigen and T4-F1mutV/PA in mice. In this example, Mice were immunized (i.m.) according to FIGS. 4A and 4B. Sera were collected according to FIG. 4B and analyzed by ELISA. "*", "", "*", and "****" denote $p<0.05$, $p<0.01$, $p<0.001$, and $p<0.0001$, respectively (ANOVA).

Stimulation of both arms of the immune system, humoral (TH2) and cellular (TH1), is essential for protection against *Y. pestis* infection[37] and probably also against *B. anthracis* infection.[38] With this in mind, the IgG subclass of the induced antibodies was determined by ELISA (FIG. 5). In mice, IgG2a titer represents TH1 response whereas IgG1 reflects the TH2 response. The data showed that the T4-displayed F1mutV/PA group elicited the highest levels of IgG2a antibodies against F1mutV or PA (p<0.0001) whereas the rest of the groups induced poor IgG2a responses (FIGS. 5B and 5D). On the other hand, although significant differences were observed, the variation of IgG1 antibody levels was relatively small among the groups (FIGS. 5A and 5C). These results indicated that the T4 nanoparticle-delivered antigens stimulated strong TH1 cellular as well as TH2 humoral responses, whereas the soluble antigens (adjuvanted with Alhydrogel®) showed a bias towards TH2 responses, as has been generally observed with many subunit vaccines.[39] Notably however, the largest among the soluble antigens, the 139-kDa F1mutV-PA triple antigen elicited significantly greater IgG2a against both F1V and PA antigens, (FIGS. 5B and 5D) when compared to the rest of the groups. Thus, the triple antigen F1mutV-PA is a more potent immunogen when compared to the individual antigens or a simple mixture.

Example 4

The Dual Vaccines Protect Mice Against Challenges with LeTx and *Y. pestis* CO92

Since the goal was to assess protection against both inhalation anthrax and pneumonic plague, it became imperative to establish appropriate challenge models. In previous reports on dual anthrax-plague vaccines (mixture of PA, F1, and V),[40-43] groups of animals were immunized with the same formulation but challenged separately with either *B. anthracis* (intratracheal administration of spores prepared from the nonencapsulated toxigenic Sterne strain[40] or subcutaneous challenge[41]) or *Y. pestis* (intraperitoneal[40] or subcutaneous[41-43] injection). However, this model would not provide an accurate assessment of dual protection because the animals were not exposed to both the agents. Therefore, two new challenge models are developed and disclosed herein; a sequential dual challenge model in which the animals were first exposed to one agent and the survivors were then challenged with the second agent, and a simultaneous dual challenge model in which the animals were exposed to both the threat agents at the same time.

In this example Balb/c mice and Brown Norway rats were chosen because both these animal strains are highly susceptible to LeTx and *Y. pestis* bacterial challenge and the protection outcomes provide good benchmarks for evaluation of vaccine efficacy.[44-46] Since the most virulent form of *Y. pestis* is the aerosolized form,[3] intranasal (i.n.) challenge was used to evaluate vaccine efficacy.

Figures 6A, 6B:
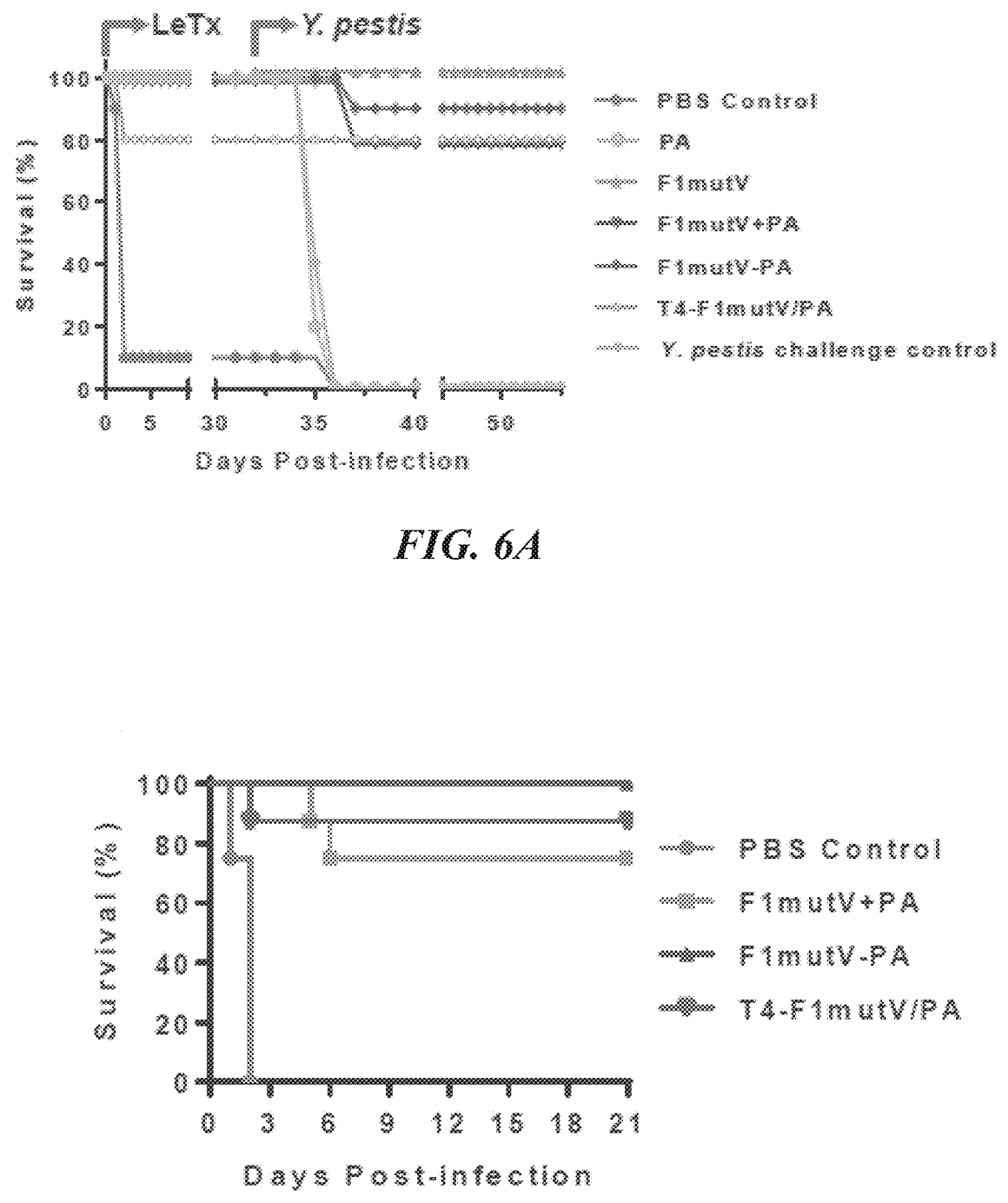
Figure 6C:
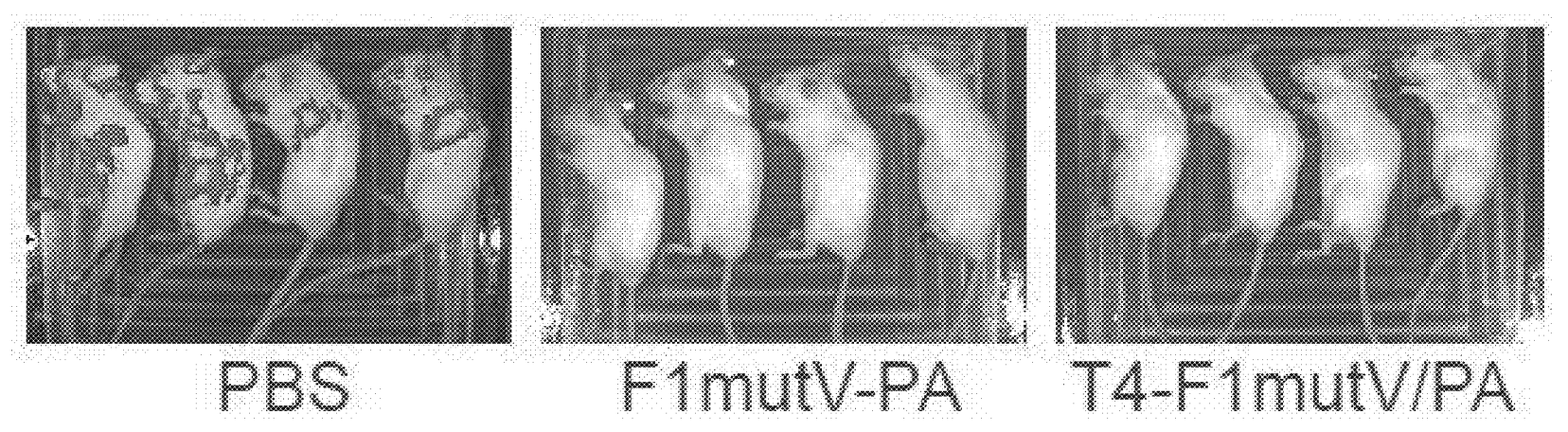

FIG. 6A is a graph illustrating survival of the mice against anthrax toxin and plague sequential challenge according to one embodiment of the present invention. Mice (n=10/group) were immunized (i.m.) according to FIG. 4b and challenged with 1 $LD_{100}$ LeTx (i.p.) on day 42 post-immunization, followed by i.n. challenge with 400 $LD_{50}$ *Y. pestis* CO92 on day 75 post-immunization. FIG. 6B is a graph illustrating survival of the mice against anthrax toxin and plague simultaneous challenge according to one embodiment of the present invention. Mice (n=8/group) were immunized (i.m.) with F1mutV+PA, F1mutV-PA or the T4-displayed F1mutV/PA. On day 44 postimmunization, mice were simultaneously challenged with 200 $LD_{50}$ *Y. pestis* (i.n.) and 1 $LD_{100}$ LeTx (i.p.). FIG. 6C are in vivo imaging of infected mice according to one embodiment. In Luciferase expression by *Y. pestis* in representative mice from the F1mutV-PA and the T4-displayed F1mutV/PA groups on day 3 post-infection is shown. The PBS control group used for imaging here was challenged with *Y. pestis* alone to minimize any interference from LeTx. Note that death of animals challenged with *Y. pestis* alone occurred in 4 days, whereas it occurred in 2 days when LeTx was included in the challenge as the toxin leads to early animal lethality (FIG. 6B).

For sequential challenge, mice were immunized as per the scheme shown in FIG. 4B and injected intraperitoneally (i.p.) with 1 $LD_{100}$ of LeTx (1:1 mixture of PA and LF, 100 μg each) two weeks after the boost. The immunized groups were 80-100% protected against LeTx challenge whereas 90% of the naïve group mice died within two days of toxin challenge. The T4-displayed F1mutV/PA group showed 80% survival whereas the PA, F1mutV-PA, and F1mutV+PA groups were 100% protected (FIG. 6A). Thirty-three days later, the surviving animals were challenged with 400 LD50 of *Y. pestis* CO92 by intranasal (i.n.) administration. The naïve mice and the F1mutV-immunized mice were used as negative and positive controls, respectively. The LeTx-challenged PA group provided another (negative) control. Dual vaccine groups showed 80-100% protection whereas the naïve and PA-immunized animals showed 100% death within 4 days post-*Y. pestis* CO92 challenge (FIG. 6A). The survival rates for individual groups were 100% for the T4-displayed F1mutV/PA group (no death), 90% for the F1mutV-PA group (one of ten mice died), and 80% for the F1mutV+PA group (two of ten mice died). As reported previously,[23] the control F1mutV-immunized mice were fully protected.

To test the potential protective ability of the vaccines in a simultaneous exposure model to both *B. anthracis* and *Y. pestis*, mice were challenged with LeTx and *Y. pestis* CO92 at the same time. Mice (n=8) were immunized twice as per the same scheme (FIG. 4B) and challenged with both LeTx (1 $LD_{100}$, i.p. administration) and *Y. pestis* CO92 (200 $LD_{50}$, i.n. administration) twenty-three days after the boost (day 44 postimmunization). Because of the simultaneous administration of two agents in mice, the challenge dose of *Y. pestis* to 200 $LD_{50}$ from 400 $LD_{50}$ is reduced (FIG. 6A). As shown in FIG. 6B, all the PBS control mice died within 2 days of challenge. The F1mutVPA vaccine provided 100% protection (8 out of 8 mice), while the T4-displayed F1mutV/PA and F1mutV+PA mixture provided 88% (7 out of 8 mice) and 75% (6 out of 8 mice) protection, respectively. Furthermore, the survivors showed complete clearing of *Y. pestis* bacteria by 3 days post-challenge (FIG. 6C). The *Y. pestis* CO92 strain used in the challenge experiment contained a luciferase expression cassette for imaging the bacteria in vivo in real time.[44] The immunized animals were negative for bioluminescence, whereas the PBS control mice showed bacterial dissemination throughout the body (FIG. 6C).

The above data sets demonstrated that both the soluble and T4 nanoparticle anthrax-plague vaccines were highly immunogenic in the mouse model and conferred near complete protection upon sequential double challenge or simultaneous double challenge with LeTx and *Y. pestis* CO92.

Example 5

Figure 7B:
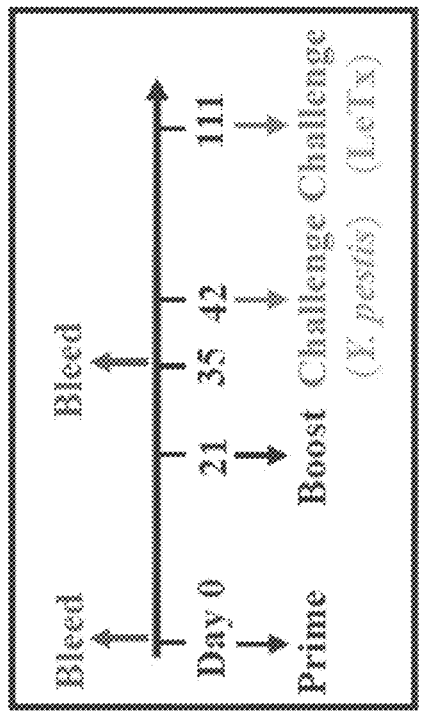
FIG. 7B shows immunization scheme using the disclosed proteins combinations for each group for rat studies according to one embodiment of the present invention.
Figure 7A:
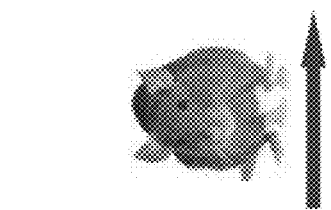
FIG. 7A is a table showing vaccine formulations used in various immunized rat groups according to one embodiment of the present invention.

The Dual Vaccines Provide Complete Protection Against Both LeTx and *Y. pestis* CO92 in Brown Norway Rats FIGS. 7A through 7E illustrate that the F1mutV-protective antigen (PA) triple antigen and T4-displayed F1mutV/PA are highly immunogenic in rats. FIG. 7A is a table showing vaccine formulations used in various immunized rat groups.

Figures 7C, 7D, 7E:
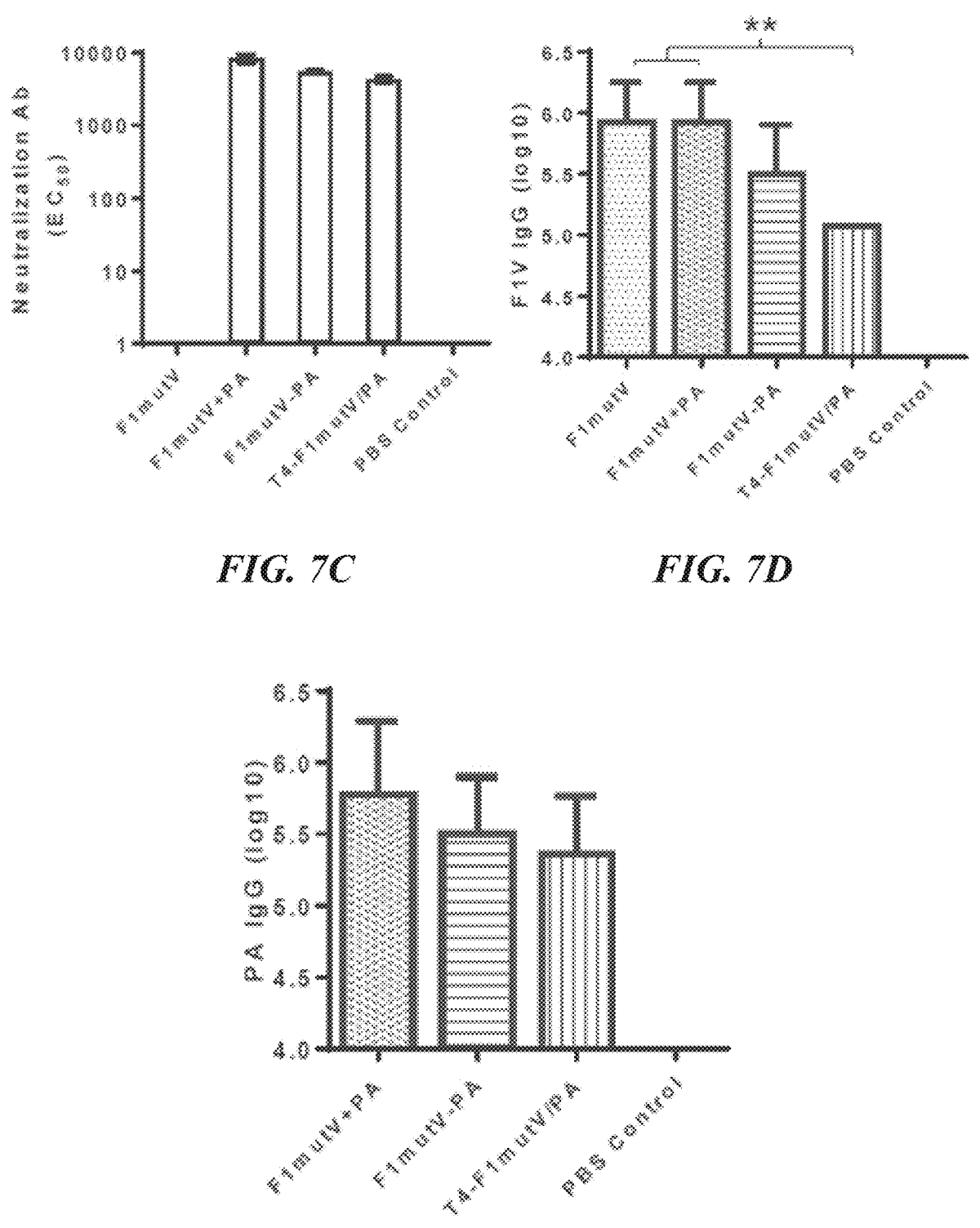

FIG. 7B shows immunization scheme using the disclosed proteins combinations for each group for rat studies. Rats (n=9) were immunized (i.m.) on day 0 and 21. Sera were collected on day 0 and 35 for antibody analysis. Animals were challenged with *Y. pestis* (i.n.) on day 42 followed by LeTx (i.v.) on day 111. FIG. 7C is a graph showing F1V-specific antibody (total IgG) titers. FIG. 7D is a graph showing PA-specific antibody (total IgG) titers. FIG. 7E is a graph showing LeTx neutralizing antibody titers. Error bars represent standard deviation (SD). "**" denotes p<0.01 (ANOVA).

Rat, the natural host of *Y. pestis* through its infection by rat fleas, is one of the most reliable models to assess the protective efficacy of vaccines against plague.[45] To further evaluate our dual vaccines, Brown Norway rats (n=9) were immunized and challenged using the scheme shown in FIGS. 7A and 7B. As in mice, the immunogens induced high levels of total antigen-specific IgG titers, up to ~3×10$^6$ (FIG. 7C). However, the F1mutV-PA and T4-displayed F1mutV/PA immunogens induced significantly lower levels of anti-F1V IgG when compared to F1mutV and F1mutV+PA antigens (p<0.01; FIG. 7C), although the anti-PA IgG levels were comparable among all the groups (FIG. 7D). Consistent with the latter, all the PA groups generated comparable LeTx neutralizing antibodies (EC$_{50}$ of 4,300 to 8,500) (FIG. 7E). The naïve animals, as expected, were negative for the antigen-specific or LeTx-neutralizing antibodies. Similarly, the PA-alone animals were negative for F1mutV antibodies and the F1mutV-alone animals were negative for PA and LeTx-neutralizing antibodies.

Figure 13C:
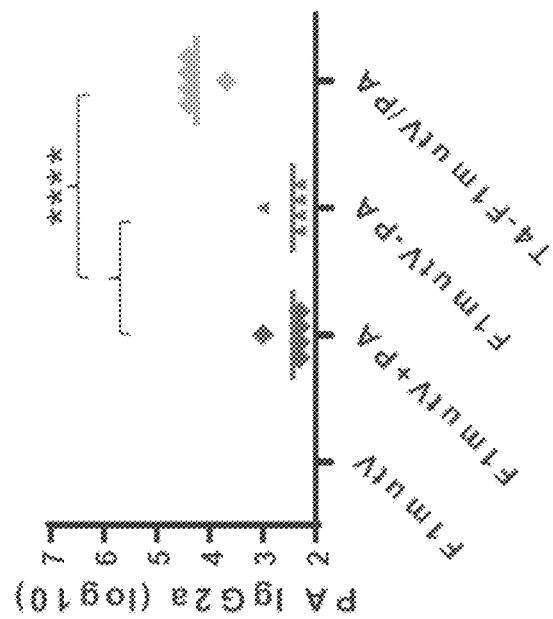
FIG. 13C is a graph showing PA-specific IgG1 antibody titers in rats according to one embodiment of the present invention.
Figure 13D:
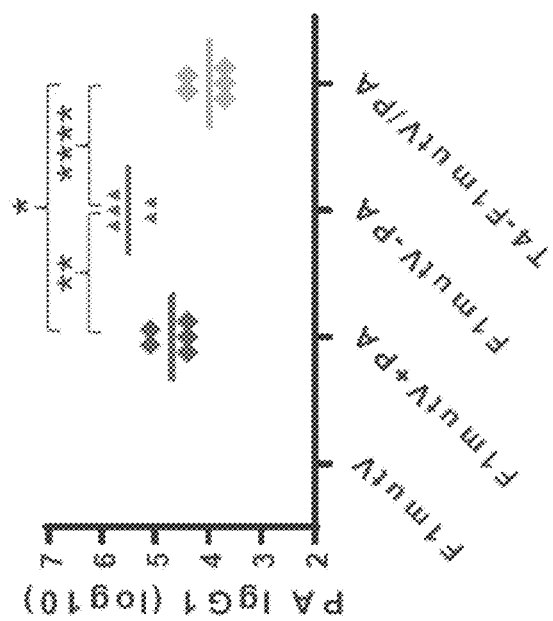
FIG. 13D is a graph showing PA-specific IgG2a antibody titers in rats according to one embodiment of the present invention.

FIG. 13A is a graph showing F1V-specific IgG1 antibody titers in rats according to one embodiment of the present invention. FIG. 13B is a graph showing F1V-specific IgG2a antibody titers in rats according to one embodiment of the present invention. FIG. 13C is a graph showing PA-specific IgG1 antibody titers in rats according to one embodiment of the present invention. FIG. 13D is a graph showing PA-specific IgG2a antibody titers in rats according to one embodiment of the present invention. Animals were immunized (i.m.) according to FIGS. 7A and 7B. Sera were collected according to FIG. 7B and analyzed by ELISA. "*", "", "*", and "****" denote p<0.05, p<0.01, p<0.001, and p<0.0001, respectively (ANOVA).

As shown in FIGS. 13A through 13 D, the IgG subclass specificity of the antibodies induced in rats followed similar trends as in mice. The T4 nanoparticle-displayed F1mutV/PA induced similar levels of both IgG1 and IgG2a antibodies against both F1mutV and PA immunogens (FIGS. 13A and 13B) whereas the soluble antigens showed a bias towards IgG1. The bias was more apparent in the case of anti-PA (FIGS. 13C and 13D) than in the case of anti-F1mutV.

Figures 8A, 8B, 8C:
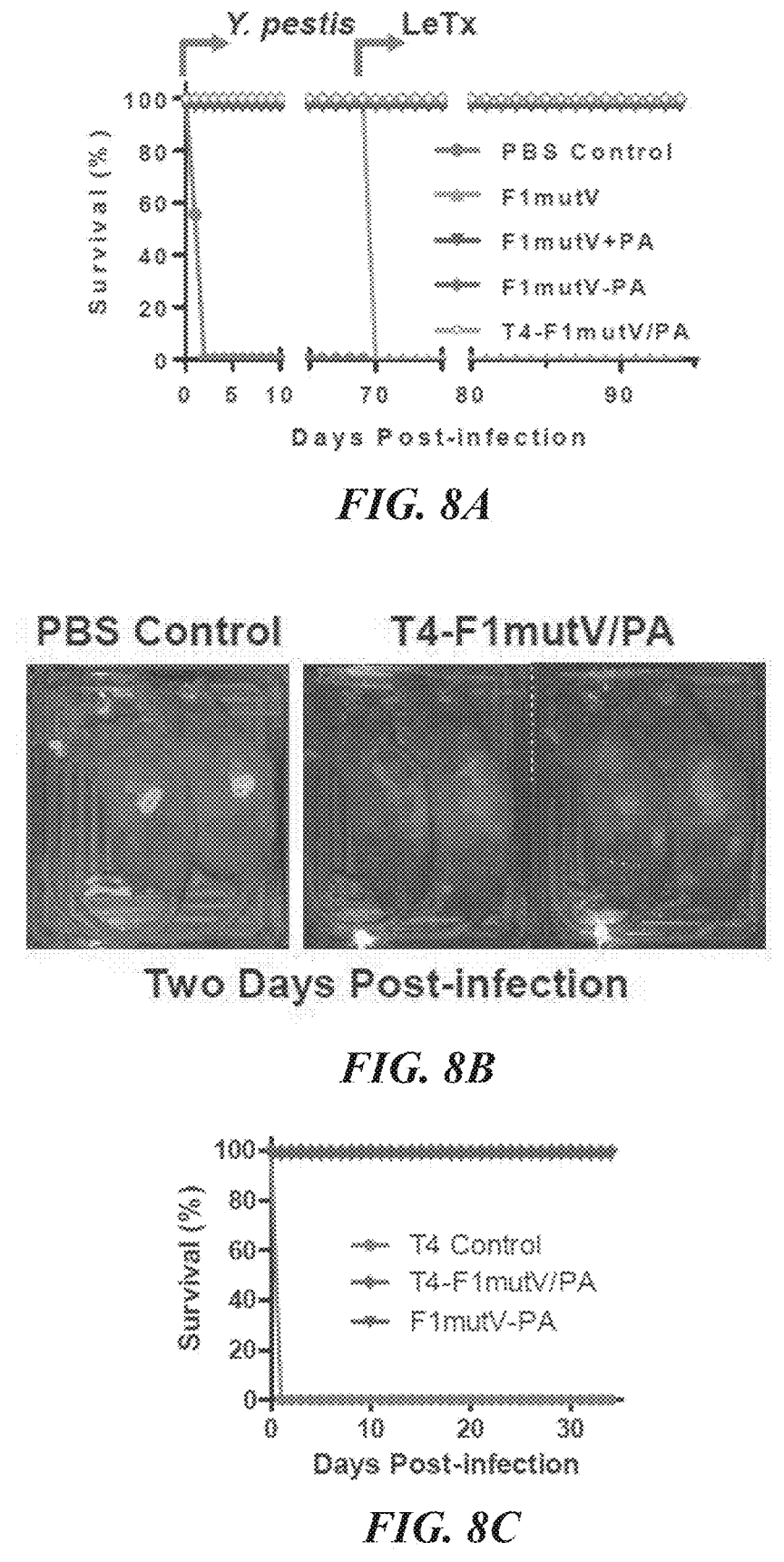

FIGS. 8A through 8C illustrate that the bivalent anthrax-plague vaccine provides complete protection against both lethal toxin (LeTx) and *Yersinia pestis* CO92 in Brown Norway rats. FIG. 8A is a graph showing survival of the rats against anthrax toxin and plague sequential challenge. Rat (n=9) were challenged intranasally with 400 LD50 *Y. pestis* CO92, followed by i.v. intravenous injection with 1 LD100 LeTx. FIG. 8B is a set of in vivo imaging of infection. Luciferase expression by *Y. pestis* in representative rats from the naïve control (PBS-immunized animals) and the T4-F1mutV/PA-immunized groups two days after *Y. pestis* CO92 challenge is shown. FIG. 8C is a graph showing survival of the rats against anthrax LeTx and plague simultaneous challenge. Rats (n=6) were immunized according to FIG. 7B and challenged simultaneously with 1×LD100 (i.v.) of LeTx and 400 LD50 *Y. pestis* CO92 (i.n.).

The protective efficacy of the dual vaccines in Brown Norway rats was first tested by the sequential dual challenge model (FIG. 8A). The animals were first subjected to i.n. challenge with 400 LD$_{50}$ of *Y. pestis* CO92. All the F1mutV-immunized rats were completely protected whereas all the rats in the naïve group died within 2 days postchallenge. The clearance of *Y. pestis* CO92 from the rats was also monitored through live imaging of the in vivo expressed luciferase (FIG. 8B). The data showed that 2 days post-challenge with *Y. pestis*, all immunized rats cleared *Y. pestis* CO92 as indicated by the lack of a detectable luciferase signal, while all control rats had strong luciferase signals throughout the body. The surviving rats were then further challenged with 1 LD$_{100}$ of LeTx (7.5 µg each of PA and LF) by intravenous (i.v.) injection on day 70 post-*Y. pestis* CO92 challenge. All immunized rats survived (FIG. 8A), but rats in the F1mutV group (negative control) as expected died within 2 h of the LeTx challenge.

In an independent experiment, rats (n=6) were simultaneously challenged with both LeTx (1 LD$_{100}$, i.v.) and *Y. pestis* CO92 (400 LD$_{50}$, i.n.). Both the dual vaccines showed 100% protection (FIG. 8C). At the end of the study, various organs (lungs, liver, and the spleen) were examined for the presence of *Y. pestis* by plate count, and no viable bacteria were detected.

Taken together, these sets of data demonstrated that although the antibody profiles to F1mutV-PA and the T4-displayed F1mutV/PA in rats were slightly different from the mouse model, the antibodies provided complete protection against sequential or simultaneous LeTx and *Y. pestis* CO92 challenges.

Example 6

Immunogenicity and Protective Efficacy of Dual Vaccines in a Rabbit Model

Figures 9F, 9G:
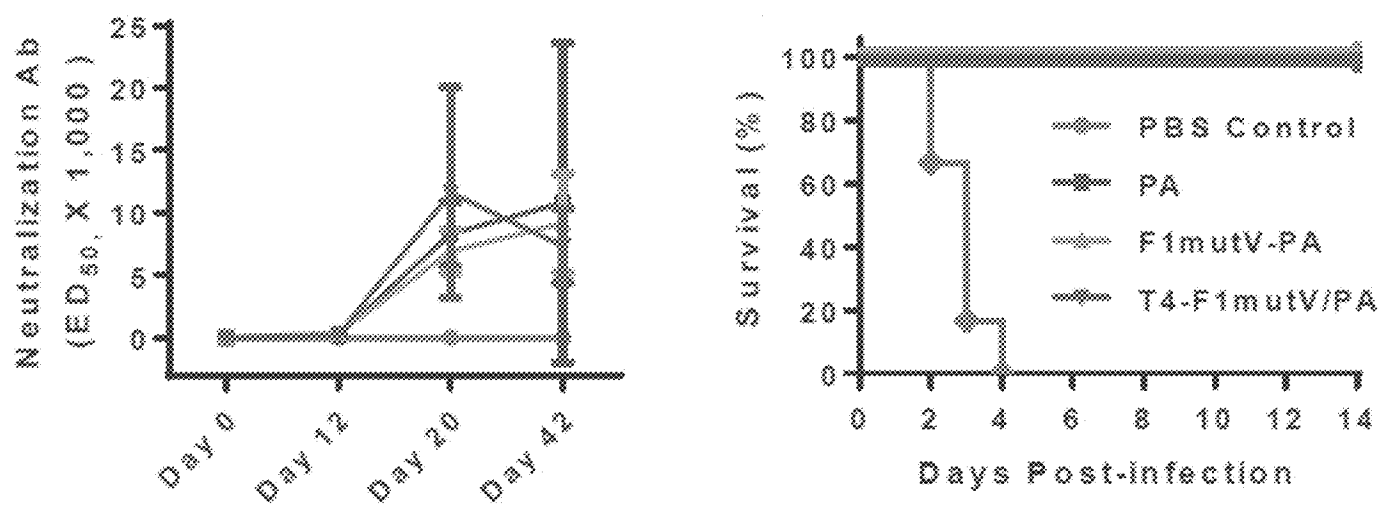

Rodents are very sensitive to infection by *B. anthracis* bacteria that produce polyglutamic acid capsule. They succumb to encapsulated *B. anthracis* infection even if these bacteria do not produce anthrax toxin.[46] Thus, to use rodents for testing efficacy of vaccines which target anthrax toxins, lethal dose toxin challenge models are preferred. Rabbits are a better model to determine protective efficacy of anthrax vaccines against encapsulated toxigenic *B. anthracis* as inhalation anthrax in these animals shows remarkably similar pathology to that observed in humans.[47] FIGS. 9A through 9G show that the triple antigen vaccines disclosed herein provide complete protection in the New Zealand White rabbit model of inhalation anthrax. FIG. 9A is a table showing vaccine formulations used in various groups in this example. Rabbits (n=10 for groups 1 and 2, and n=6 for groups 3 and 4, equal numbers of males and females) were vaccinated (i.m.) with the indicated antigens. FIG. 9B is an immunization scheme for rabbit study in this example. FIG. 9C is a graph showing F1V-specific antibody (total IgG) titers on day 20 in this example. Error bars represent standard deviation (SD). FIG. 9D is a graph showing F1V-specific antibody (total IgG) titers on day 42 in this example. Error bars represent standard deviation (SD). FIG. 9E is a graph showing protective antigen (PA)-specific antibody (total IgG) titers. Titers for bleeds on days 0, 12, 20, and 42 are shown. FIG. 9F is a graph showing LeTx neutralizing antibody titer. All animals immunized with PA induced robust neutralization antibody and no significant difference was observed among the PA-immunized groups. FIG. 9G is a graph showing survival of the rabbits challenged with 200 LD50 of aerosolized *B. anthracis* Ames spores. Error bars represent standard deviation (SD) of the mean. "" and "*" denote $p<0.01$ and $p<0.001$, respectively (ANOVA).

As shown in FIG. 9A and FIG. 9B, rabbits (n=10 for groups 1 and 2, and n=6 for groups 3 and 4, equal numbers of males and females) were primed on day 0 and boosted on day 14 by i.m. injections of vaccine formations. Sera were collected on days 0, 12, 20, and 42 (FIG. 9B) and subjected to immunological analyses. The data showed that both the soluble and T4 nanoparticle vaccines induced high levels of anti-PA antibodies as well as LeTx neutralizing antibodies at day 20 (FIGS. 9E and 9F). Importantly, the T4 nanoparticle vaccine elicited the highest antibody levels ($p<0.001$; FIG. 9E), although the titer dropped by 30% by day 42 ($p<0.01$; FIG. 9E).

The rabbits also induced high levels of anti-F1mutV antibodies. At day 20, six days after the boost, the end point titers were in the range of $0.3$-$1.6 \times 10^6$ (FIG. 9C). While the total IgG levels were comparable among groups, they were more durable in the T4 vaccine group than in the soluble vaccine group, as shown by 11% drop on day 42 in the F1mutV-PA group and no significant drop in the T4-F1mutV/PA group ($p<0.01$; FIG. 9D).

Figure 14A:
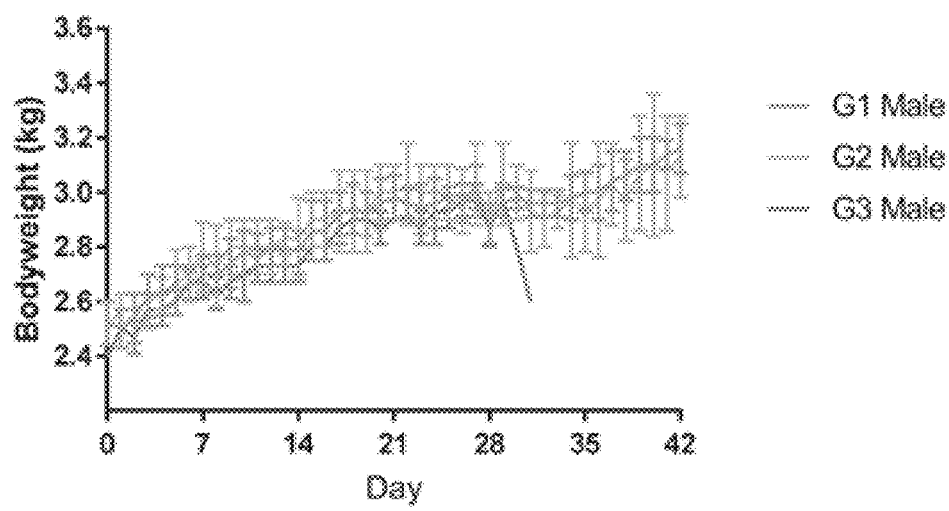
FIG. 14A is a graph showing body weight changes in male after B. anthracis challenge (200 LD50, aerosol) according to one embodiment of the present invention.
Figure 14B:
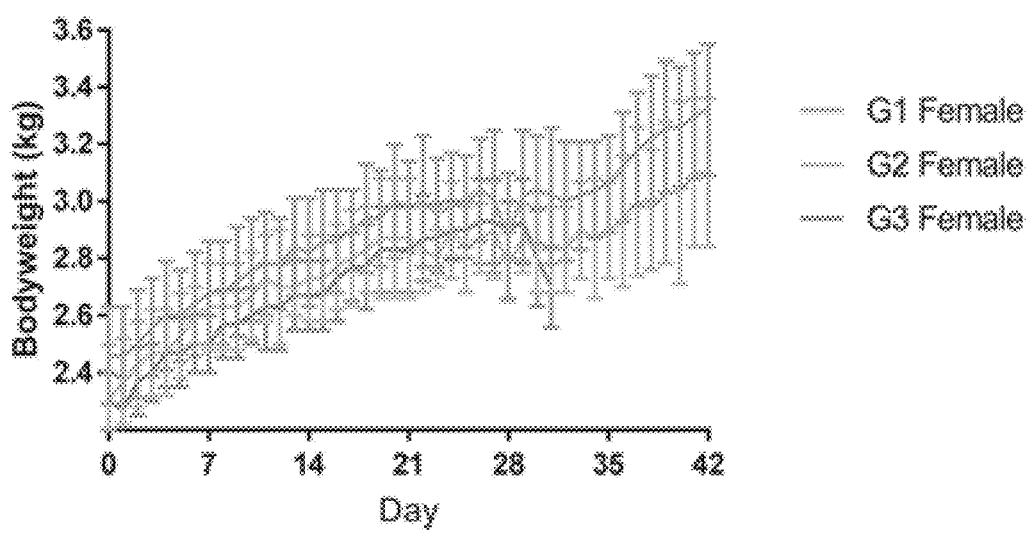
FIG. 14B is a graph showing body weight changes in female rabbits after B. anthracis challenge (200 LD50, aerosol) according to one embodiment of the present invention.
Figure 14C:
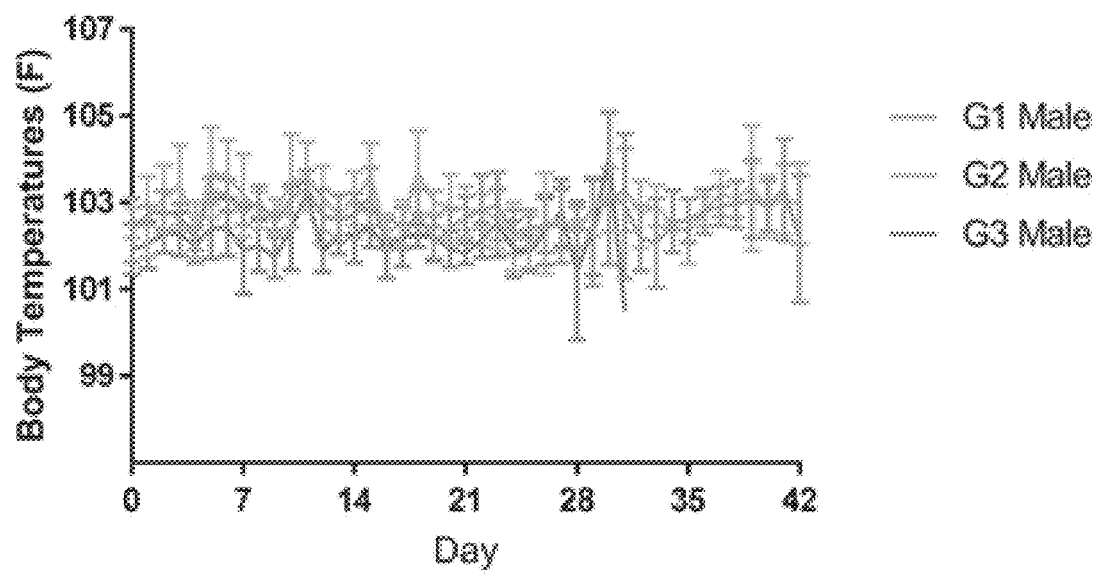
FIG. 14C is a graph showing body temperature changes in male rabbits after B. anthracis challenge (200 LD50, aerosol) according to one embodiment of the present invention.
Figure 14D:
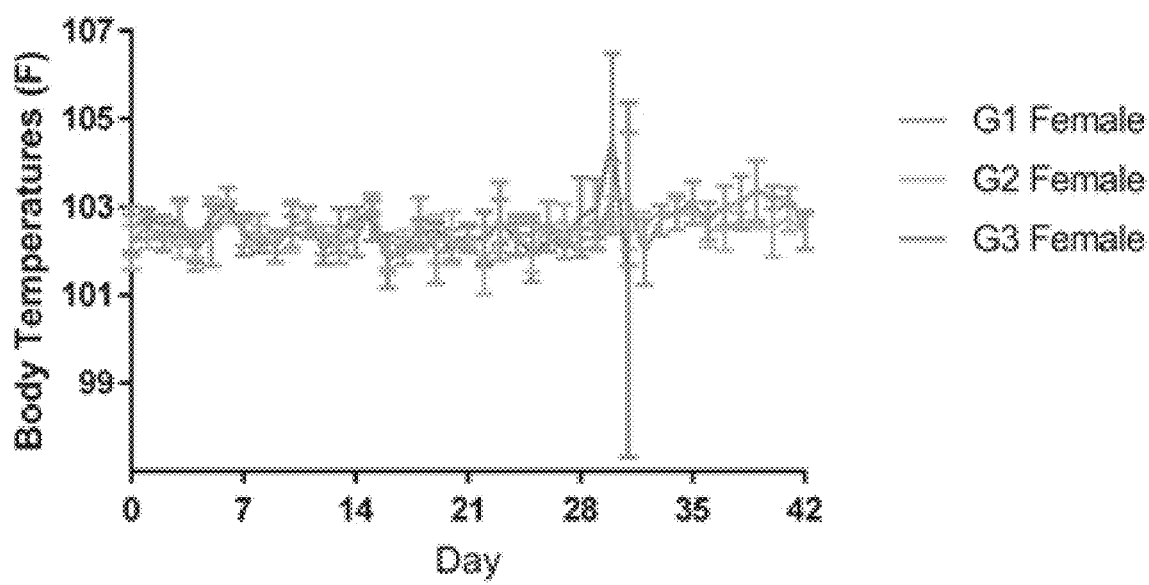
FIG. 14D is a graph showing body temperature changes in female rabbits after *B. anthracis* challenge (200 LD50, aerosol) according to one embodiment of the present invention.

Rabbits were challenged one week after the boost with 200 $LD_{50}$ of aerosolized *B. anthracis* Ames spores. All the naïve control rabbits succumbed to the anthrax disease 2-4 days post-infection, while all the dual vaccine immunized rabbits were completely protected (FIG. 9G). Between the challenge day and the end of the study (days 28 to 42), vaccinated animals from Groups 1, 2, and 3 continued to show an increase in the body weight, while control animals showed weight loss as well as body temperature changes before death (FIGS. 14A through 14 D). FIGS. 14A through 14 D show body weight changes body weight changes in male (FIG. 14A) and female (FIG. 14B) rabbits, and body temperature changes in male (FIG. 14C) and female (FIG. 14D) rabbits after *B. anthracis* challenge (200 LD50, aerosol) according to one embodiment of the present invention. Animals were immunized (i.m.) according to FIG. 9A and FIG. 9B and challenged (aerosol) with 200 $LD_{50}$ *B. anthracis* two weeks after last immunization. The rabbits were monitored daily for body weight and body temperature.

In further experiments, blood samples for bacteremia were drawn before the challenge on day 27 (baseline), and on days 29-33 (1-5 days post-exposure) and day 42. Tables 1 and 2 shows a summary of challenge experiments and qualitative bacteremia in blood. As shown in Table 2, vaccinated animals (Groups 1-2) never developed bacteremia whereas all unvaccinated control animals (Group 3) became positive for bacteremia before they succumbed to the disease. To determine the bacterial load of internal organs, post-mortem collection of specimens was performed after scheduled euthanasia of surviving animals on study day 42 (Groups 1 and 2) or after animals died due to the anthrax exposure (Group 3). Table 3 shows individual chart of bacterial load of tissue samples. All vaccinated animals from Groups 1 and 2 had cleared the agent from the lungs and did not have any bacteria in the brain, liver, or spleen. In contrast, tissue samples collected from unvaccinated control animals (Group 3) had very high bacterial titers indicative of systemic anthrax infection. In increasing order, the brain titer average was $5 \times 10^6$ CFU/g, the liver average was $3 \times 10^7$ CFU/g, and the highest average titer of $5 \times 10^8$ CFU/g was obtained for lung and spleen samples. Gross necropsy and histological analyses were consistent with these data.

The above sets of data demonstrated that both our soluble and T4 nanoparticle dual anthrax-plague vaccines provided complete protection in rabbits against aerosolized *B. anthracis* Ames spore challenge.

TABLE 1

Summary of Challenge Experiments

| Animal models | | Challenge agent | Challenge dose (route) | Schedule |
|---|---|---|---|---|
| Mouse | sequential challenge | LeTx and *Y. pestis* CO92 | 1 $LD_{100}$ of LeTx (i.p.) and 400 $LD_{50}$ of *Y. pestis* (i.n.) | Challenge with LeTx on day zero followed by *Y. pestis* challenge on day 33 |
| | simultaneous challenge | LeTx and *Y. pestis* CO92 | 1 $LD_{100}$ of LeTx (i.p.) and 200 $LD_{50}$ of Y. pestis (i.n.) | Simultaneous challenge with LeTx and *Y. pestis* on day zero |
| Rat | sequential challenge | LeTx and *Y. pestis* CO92 | 400 $LD_{50}$ of *Y. pestis* (i.n.) and 1 $LD_{100}$ of LeTx (i.v.) | Challenge with *Y. pestis* on day zero followed by LeTx challenge on day 70 |
| | simultaneous challenge | LeTx and *Y. pestis* CO92 | 1 $LD_{100}$ of LeTx (i.v.) and 400 $LD_{50}$ of *Y. pestis* (i.n.) | Simultaneous challenge with LeTx and *Y. pestis* on day zero |
| Rabbit | | *B. anthracis* Ames spores | 200 $LD_{50}$ of aerosolized *B. anthracis* Ames spores (i.n.) | challenge with aerosolized *B. anthracis* Ames spores on day zero |

TABLE 2

Summary of Qualitative Bacteremia in Blood

| Animal ID | | Day 27 | Day 29 | Day 30 | Day 31 | Day 32 | Day 33 | Day 42 |
|---|---|---|---|---|---|---|---|---|
| Group 1 | 2M14117 | − | − | − | − | | − | − |
| F1mutV-PA | 2M14122 | − | − | − | − | | − | − |
| (Male) | 2M14120 | − | − | − | − | | − | − |
| | 2M14106 | − | − | − | − | | − | − |
| | 2M14111 | − | − | − | − | | − | − |

TABLE 2-continued

Summary of Qualitative Bacteremia in Blood

| Animal ID | | Day 27 | Day 29 | Day 30 | Day 31 | Day 32 | Day 33 | Day 42 |
|---|---|---|---|---|---|---|---|---|
| Group 1 | 2F14123 | – | – | – | – | | – | – |
| F1mutV-PA | 2F14124 | – | – | – | – | | – | – |
| (Female) | 2F14129 | – | – | – | – | | – | – |
| | 2F141134 | – | – | – | – | | – | – |
| | 2F14136 | – | – | – | – | | – | – |
| Group 2 | 3M14110 | – | – | – | – | | – | – |
| PA | 3M14115 | – | – | – | – | | – | – |
| (Male) | 3M14118 | – | – | – | – | | – | – |
| Group 2 | 3F14127 | – | – | – | – | | – | – |
| PA | 3F14139 | – | – | – | – | | – | – |
| (Female) | 3F14141 | – | – | – | – | | – | – |
| Group 3 | 4M14107 | – | – | + | + | | | |
| PBS control | 4M14112 | – | – | + | | | | |
| (Male) | 4M14131 | – | – | – | + | + | | |
| Group 3 | 4F14105 | – | – | – | + | | | |
| PBS control | 4F14125 | – | – | + | + | | | |
| (Female) | 4F14140 | – | – | + | | | | |

TABLE 3

Individual Chart of Bacterial Load of Tissue Samples

| Animal ID | | Brain (CFU/g) | Liver (CFU/g) | Lung (CFU/g) | Spleen (CFU/g) |
|---|---|---|---|---|---|
| Group 1 | 2M 14117 | 0.0E+00 | 00E+00 | 0.0E+00 | 0.0E+00 |
| F1mutV- | 2M 14122 | 0.0E+00 | 0.0E+00 | 0.0E+00 | 0.0E+00 |
| PA | 2M 14120 | 0.0E+00 | 0.0E+00 | 0.0E+00 | 0.0E+00 |
| (Male) | 2M 14106 | 0.0E+00 | 0.0E+00 | 0.0E+00 | 0.0E+00 |
| | 2M 14111 | 0.0E+00 | 0.0E+00 | 0.0E+00 | 0.0E+00 |
| Group 1 | 2F 14123 | 0.0E+00 | 00E+00 | 0.0E+00 | 0.0E+00 |
| F1mutV- | 2F 14129 | 0.0E+00 | 0.0E+00 | 0.0E+00 | 0.0E+00 |
| PA | 2F 14124 | 0.0E+00 | 0.0E+00 | 0.0E+00 | 0.0E+00 |
| (Female) | 2F 14136 | 0.0E+00 | 0.0E+00 | 0.0E+00 | 0.0E+00 |
| | 2F 14134 | 0.0E+00 | 0.0E+00 | 0.0E+00 | 0.0E+00 |
| Group 2 | 3M 14110 | 0.0E+00 | 0.0E+00 | 0.0E+00 | 0.0E+00 |
| PA | 3M 14115 | 0.0E+00 | 0.0E+00 | 0.0E+00 | 0.0E+00 |
| (Male) | 3M 14118 | 0.0E+00 | 0.0E+00 | 0.0E+00 | 0.0E+00 |
| Group 2 | 3F 14127 | 0.0E+00 | 0.0E+00 | 0.0E+00 | 0.0E+00 |
| PA | 3F 14141 | 0.0E+00 | 0.0E+00 | 0.0E+00 | 0.0E+00 |
| (Female) | 3F 14139 | 0.0E+00 | 0.0E+00 | 0.0E+00 | 0.0E+00 |
| Group 3 | 4M 14112 | 6.4E+06 | 7.5E+06 | 9.9E+06 | 7.9E+06 |
| PBS | 4M 14107 | 9.8E+05 | 2.9E+06 | 9.1E+08 | 1.4E+00 |
| control | 4M 14105 | 2.0E+0.6 | 5.6E+07 | 1.4E+09 | 2.5E+09 |
| (Male) | | | | | |
| Group 3 | 4F 14131 | 1.0E+07 | 0.0E+00 | 4.6E+06 | 1.9E+06 |
| PBS | 4F 14125 | 2.4E+06 | 3.9E+07 | 8.0E+08 | 2.7E+08 |
| control | 4F 14140 | 7.9E+06 | 4.9E+07 | 4.8E+07 | 6.2E+06 |
| (Female) | | | | | |

CONCLUSIONS

Since the deadly anthrax attacks of 2001, stockpiling of recombinant plague and anthrax vaccines has been a national priority. However, no candidate vaccines have yet been able to meet the licensing requirements. A single vaccine, rather than two different vaccines, which can protect against both Tier-1 bioterror pathogens, *B. anthracis* and *Y. pestis*, would greatly accelerate this effort. We report here two such vaccines, a triple fusion protein (F1mutV-PA) that incorporates all three key antigens, F1 and V from *Y. pestis* and PA from *B. anthracis*, and a T4 phage nanoparticle with all three antigens arrayed on the virus capsid (T4-F1mutV/PA). These candidate vaccines retained the functionality and immunogenicity of the antigens and elicited robust and protective immune responses in three animal models, namely mouse, rat, and rabbit.

There have been several previous studies on developing a dual anthrax-plague vaccine, all involving a simple mixture of F1, V, and PA proteins.[40-42] Both synergy and interference in antibody production have been reported when the antigens were mixed and none of the candidate vaccines were tested for efficacy against both the biothreat agents.[40-42] Our studies showed no evidence of antigen interference occurring with our dual vaccines in three different animal models. Although enhancement was observed in the case of F1mutV-PA, which elicited significantly higher levels of PA-specific IgG than PA alone or F1mutV+PA mixture, this was only observed in the mouse model and not in the rat and rabbit models.

Disclosed T4 nanoparticle vaccine elicited robust and balanced humoral (TH1) and cellmediated (TH2) immune responses. This was observed with both the anthrax and plague antigen-specific responses in two animal models, as well as in our previous studies.[23] The soluble immunogens on the other hand showed a bias towards TH2 responses, as has been generally observed with subunit vaccines.[23,48] Presumably, the nanoparticle character of the T4 phage allows for its efficient uptake by the antigen presenting cells and crosspresentation to both MHC-I and MHC-II molecules, stimulating both the humoral and cellular arms of the immune system. Thus, T4 might represent a particularly useful platform for clearance of *Y. pestis* and *B. anthracis* bacteria.

Vaccine efficacy studies demonstrated that the disclosed dual vaccines are highly effective in protection against both anthrax and plague challenges. This has been determined in three different animal models using i) multiple challenge formats, including: sequential challenge and simultaneous challenge using lethal doses of both LeTx and *Y. pestis* CO92, ii) multiple routes of administration: intranasal, intraperitoneal, intravenous, and aerosol administration of *Y. pestis* CO92, LeTx, and *B. anthracis* Ames spores, respectively, iii) two of the best animal models available for inhalation anthrax (New Zealand white rabbit), and pneumonic plague (Brown Norway rat). These studies are the first to demonstrate protection of vaccinated animals against simultaneous administration of both anthrax and plague.

The recombinant F1mutV-PA vaccine is a soluble molecule and can be cost-effectively produced in *E. coli*. It can be adjuvanted with Alum or another licensed adjuvant using the already established processes in vaccine manufacturing. Indeed, F1mutV-PA adjuvanted with liposomes or Alum-liposomes mixture provided similarly robust immune responses and complete protection against both anthrax and plague.

The novel T4 nanoparticle platform has several useful features, as follows: i) unlike traditional vaccines, it does not require an external adjuvant and elicits robust humoral and cellular immune responses;[23,32,49] ii) it is an extremely stable particle, suitable for storage, stockpiling, and deployment on a mass scale;[29] iii) it is a multivalent platform, allowing incorporation of additional antigens belonging to other biothreat or emerging pathogens;[30] iv) no adverse effects to vaccination have been observed in many preclinical studies performed in mouse,[23,26,31,49] rat,[23] rabbit,[50] and rhesus macaque[32] models, or in a human trial where T4 phage was given orally;[51] and v) no pre-existing antibodies are present in humans.

Disclosed study represents a new approach to develop anthrax and plague vaccines. Both dual vaccines described here are strong candidates for stockpiling as part of our national preparedness against two of the deadliest bioterror threats, anthrax and plague.

Example 7

Methods
Ethics Statement

This study was conducted in accordance with the Guide for the Care and Use of Laboratory Animals recommended by the National Institutes of Health. All animal experiments were performed according to the protocols approved by the Institutional Animal Care and Use Committees of the University of Texas Medical Branch, Galveston, Tex. (Office of Laboratory Animal Welfare assurance number: A3314-01), The Catholic University of America, Washington, D.C. (Office of Laboratory Animal Welfare assurance number: A4431-01), and Southern Research Institute (Study No: 13538.01.15; Birmingham, Ala.). This is not their assurance number.

Construction of Recombinant Plasmids

The *E. coli* expression vector pET28b (EMD Biosciences, Darmstadt, Germany) was used for recombinant plasmid construction. Plasmids pET-F1mutV and pET-F1mutVSoc were constructed in previous studies.[23,25] In order to construct pET-F1mutV-PA, overlap polymerase chain reaction (PCR) was used with the primers listed below. Using previously constructed Soc fusion protein Soc-PA as a template,[30] the PA fragment was amplified such that the HindIII site (underlined) was destroyed and a short linker (5'-CTGCT-3'; boldfaced) was introduced towards the 5' end of the HindIII Forward primer after the HindIII restriction site to keep the codon in frame.

```
HindIII Forward:
                                        (SEQ ID NO: 8)
5'-ACCCAAGCTTCTGCTGAAGTTAAACAGGAGAACCGG TTATT-3'

Upstream Reverse:
                                        (SEQ ID NO: 9)
5'-GTGATTAATAAAGCCTCTAATTCTAACAAA-3'

Downstream Forward:
                                        (SEQ ID NO: 10)
5'-TTTGTTAGAATTAGAGGCTTTATTAATCAC-3'

XhoI Reverse:
                                        (SEQ ID NO: 11)
5'-GCCCTCGAGTTATCCTATCTCATAGCCTTTTTTAG-3'
```

The PA fragment was then double-digested with HindIII/XhoI and cloned into pETF1mutV-Soc, cut with the same enzymes, to replace Soc. The resulting pET-F1mutV-PA contains the PA fragment fused in-frame to the C-terminus of F1mutV with a short linker (Glu-Ala-Ser-Ala) (SEQ ID NO: 12) in between. The pET-Soc-PA was constructed by replacing the F1mutV gene of pET-F1mutV-PA with Soc using the following primers, where the underlined sequences corresponded to the recognition sequences for the respective enzymes:

```
Soc NheI Forward:
                                        (SEQ ID NO: 13)
5'-GCATCCGCTAGCGGTGGTTATGTAAACATCAAA-3'

Soc HindIII Reverse:
                                        (SEQ ID NO: 14)
5'-CAGAAGCTTCACCACTTACTGGTGTAGGGGTAA AC-3'
```

Soc fragment was double-digested with NheI/HindIII and cloned into pET-F1mutV-PA, cut with the same enzymes, to replace F1mutV. The resulting pET-Soc-PA contains the Soc gene fused in-frame to the N-terminus of PA with a short linker (Glu-Ala-Ser-Ala) (SEQ ID NO: 12) in between. All constructs were confirmed by DNA sequencing.

Expression and Purification of Immunogens

PA and LF were purified as described previously.[52,53] The *E. coli* BL21-codon plus (DE3)-RIPL cells (Agilent Technologies, Santa Clara, Calif.) harboring various recombinant plasmids constructed as above were induced with 1 mM Isopropyl β-D-1-thiogalactopyranoside (IPTG) for 2 h at 28° C. Cells were harvested and resuspended in binding buffer (50 mM Tris-HCl, pH 8, 300 mM NaCl, 20 mM imidazole) containing protease inhibitor cocktail (Roche, USA, Indianapolis, Ind.). Cells were lysed at 12,00 psi using a French press (Aminco, Urbana, Ill.) and the soluble fractions containing the His-tagged fusion proteins were isolated by centrifugation at 34,000×g for 20 min. Proteins were first subjected to purification by HisTrap column (AKTA-prime, GE Healthcare Bio-Sciences Corp., Piscataway, N.J.). Peak fractions containing the desired protein were further purified by gel-filtration on a HiLoad 16/60 Superdex 200 column (AKTA-FPLC, GE Healthcare Bio-Sciences Corp.) in a buffer containing 20 mM Tris-HCl, pH 8 and 100 mM NaCl. The purified proteins were quantified and stored at −80° C. until use. The Endosafe-PTS system (Charles River Laboratories International, Inc., Wilmington, Mass.) was used to determine levels of lipopolysaccharide (LPS) contamination in the purified recombinant proteins and LPS-free preparations were used for animal immunizations.

Biochemical Function of F1mutV-PA

The furin cleavage of F1mutV-PA was carried out by incubation of F1mutV-PA (SEQ ID NO: 4) with human furin (amino acid [aa] residues 1-604; kindly provided by Dr. Iris Lindberg, University of Maryland Medical School, Baltimore, Md.). F1mutV-PA or PA was treated with different amounts of furin (molar ratio of protein:furin varied from 200,000:1 to 160:1) in 20 µl buffer containing 50 mM HEPES, pH 7.5, 2 mM CaCl2, 0.5 mM EDTA, and 0.2% β-octylglucoside. The reaction was performed at 37° C. for 30 min and terminated by boiling in 2×SDS loading buffer for 5 min. Samples were then analyzed by 4-20% gradient sodium dodecyl sulfate polyacrylamide gel electrophoresis (SDSPAGE).

The binding of F1mutV-PA to the PA receptor CMG2 was carried out by incubation of F1mutV-PA with CMG2 (aa residues 40-218; kindly provided by Dr. Robert Liddington, Sanford-Burnham Medical Research Institute, La Jolla, Calif.) at room temperature for 30 min. F1mutV-PA or PA was incubated with different amounts of CMG2 (molar ratio of protein:CMG2 varied from 4.8:1 to 0.15:1) in 20 µl buffer containing 50 mM HEPES, pH 7.5, 2 mM CaCl2, 0.5 mM EDTA and 0.2% β-octylglucoside. Samples were analyzed by electrophoresis using 4-12% gradient Native-PAGE (Invitrogen).

Binding to the N-terminal domain of lethal factor (LFn) was tested by mixing furin-treated F1mutV-PA with increasing amounts of LFn (molar ratio of F1mutV-PA or PA:LFn varied from 1.92:1 to 0.06:1). F1mutV-PA or PA was cleaved by furin as described above (protein: furin at 160:1) followed by LFn binding for 30 min at room temperature and complex evaluation by electrophoresis using 4-12% gradient Native-PAGE (Invitrogen).

In Vitro Binding of Antigens to T4 Phage Capsid

In vitro binding of Soc fusion protein to Hoc-Soc-T4 phage was carried out as previously described.[23,25] Briefly, Soc fusion proteins were incubated with the Hoc-Soc-phage at 4° C. for 45 min. The phage particles were centrifuged at 34,000×g for 45 min and the supernatants containing the unbound proteins were discarded. Phage pellets containing the bound plague antigens were washed twice with excess PBS buffer (pH 7.4). The final pellets were resuspended in PBS buffer (pH 7.4) and analyzed by 4-20% gradient SDSPAGE before injection into animals.

Mouse Immunizations and Challenges

Six- to eight-week-old female Balb/c mice (17-20 g) were purchased from The Jackson Laboratory (Bar Harbor, Me.) and randomly grouped and acclimated for 7 days. Phage-displayed antigens were prepared as described above and directly used for immunization without any adjuvant (25 µg each of F1mutV and PA per injection). For other antigens, the purified proteins were adsorbed on Alhydrogel® (Brenntag Biosector, Frederiksund, Denmark) containing 0.19 mg of aluminum per dose. A total of 25 µg antigen was injected for the F1mutV or the PA group, 25 µg F1mutV plus 25 µg PA for the F1mutV+PA group, and 50 µg F1mutV-PA for the F1mutV-PA group on days 0 and 21 via the i.m. route. Control mice received the same amount of Alhydrogel®, but without any antigen. Alternate legs were used for each immunization. Blood was collected from each animal by the retro-orbital route on days 0 (pre-bleeds) and 35. In some studies, mice were i.p. challenged first with 1 $LD_{100}$ of LeTx followed by intranasal challenge with 400 $LD_{50}$ Y. pestis CO92 33 days after LeTx challenge. In other studies, mice were i.p. challenged with 1 $LD_{100}$ of LeTx and 200 $LD_{50}$ Y. pestis CO92 on the same day, as indicated in the description for FIGS. 6A through 6C. Animals were monitored twice daily for mortality and other clinical symptoms.

Rat Immunization and Challenge

Female Brown Norway rats (50-75 g), purchased from Charles River Laboratories (New Jersey, N.J.) were randomized into five groups (nine rats per group) and were acclimated for seven days before manipulation. The immunogens were formulated and rats were immunized via i.m. route as described above for mice. Sera were obtained on day 35 for antibody analysis. The animals were bled by the saphenous vein. Rats were first intranasally challenged on day 42 with ~400 $LD_{50}$ Y. pestis CO92 and monitored twice daily for morbidity and mortality over a period of 69 days. The animals that survived were further challenged with 1 $LD_{100}$ LeTx (7.5 µg of each of the toxin components [LF and PA], by the i.v. route]) and monitored for another 24 days for morbidity and mortality. In a separate experiment, rats (n=6) were immunized with phage-displayed antigens (25 µg each of F1mutV and PA per injection) or 50 µg F1mutV-PA adsorbed on Alhydrogel® containing 0.19 mg of aluminum on days 0 and 21. One week after last immunization, rats were challenged simultaneously with 1 $LD_{100}$ of LeTx and 400 $LD_{50}$ Y. pestis CO92 as described above.

Rabbit Immunization and Challenge

Rabbit experiments were performed by Southern Research Institute (Study No: 13538.01.15; Birmingham, Ala.). Briefly, a total of 32 New Zealand white rabbits were divided into four groups. Groups 1 and 2 were vaccinated with T4-F1mutV/PA (25 µg each) and F1mutV-PA (50 µg), respectively (n=10 per group), while group 3 received PA (25 µg; n=6) alone. Alhydrogel® was used as an adjuvant in groups 2 and 3 (600 µg/rabbit). Control animals (group 4) received the same amount of Alhydrogel®, but without any antigen (n=6). Rabbits were injected on day 0 and boosted on day 14. Sera were collected on days 0 (baseline), 12, 20, and 42, and immunological response was monitored by utilizing the anthrax LeTx neutralization assay (TNA) and the enzyme-linked immunosorbent assay (ELISA) with the PA antigen. Anti-F1V IgG was analyzed by utilizing ELISA with the F1V antigen. Animals were challenged with 200 $LD_{50}$ of aerosolized encapsulated B. anthracis Ames spores on day 28 and monitored for body weight, body temperature, and mortality until day 42 at which point the remaining animals were euthanized. On days 27, 29-33 and 42, blood samples (approximately 0.2 ml) were collected from the central ear artery into tubes containing sodium polyanethole sulfonate and processed for qualitative microbiological analysis (bacteremia) on the same day. On day 42, the remaining animals were euthanized by an intravenous administration of a barbiturate overdose for tissue collection (brain, liver, lung, and spleen). Tissues were further processed for microbiological and histological analyses.

Determination of IgG and IgG Subtype Antibodies

Antibody titers were determined by ELISA as described previously.[23] For rat IgG, horseradish peroxidase (HRP)-conjugated goat anti-rat IgG (KPL, Gaithersburg, Md.) was used as secondary antibodies. For mouse or rat IgG subtypes, HRP-conjugated goat anti-mouse or anti-rat IgG1 or IgG2a secondary antibodies (Abcam, Cambridge, Mass.) were used. For rabbit anti-PA IgG titers, plates were coated with PA and affinity-purified rabbit anti-PA polyclonal antibody was used to generate a standard curve, from which the sample anti-PA IgG concentrations (ng/mL) were determined. Samples were initially at 1:200; additional dilutions were performed as necessary to ensure that values could be determined from the standard curve.

Anthrax LeTx Neutralization Assay (TNA)

Anthrax lethal-toxin-neutralizing assay (TNA) was performed as described previously.[54] Briefly, PA and LF (200 ng/ml for each component) were prepared in Dulbecco's modified Eagle's medium (DMEM), and sera were diluted serially into the toxin mixture and incubated for 1 h at 37° C. Toxin-serum mixtures were transferred to RAW 264.7 macrophage cells grown to confluence in 96-well plates and incubated for 5 h, and cell viability assessed by incubation with MTT [3-(4,5-dimethylthiazo-2-yl)-2,5-diphenyltetrazolium bromide](Sigma, St. Louis, Mo.) at a final concentration of 0.5 mg/ml for 30 min. An insoluble pigment (formazan) produced by living cells was dissolved in 0.5% (wt/vol) SDS, 25 mM HCl, in 90% (vol/vol) isopropanol, and the optical density (570 nm) measured to assess viability. The effective serum concentration inducing 50% neutralization (EC50) was calculated with Prism software (Graphpad Software, Inc., San Diego, Calif.).

Live Animal Imaging

Depending on the experiment (see figure legends), two or three days after the challenge with *Y. pestis* CO92-luciferase strain, the animals were imaged by using an IVIS 200 bioluminescence and fluorescence whole-body imaging workstation (Caliper Corp., Alameda, Calif.) in the ABSL-3 facility following light anesthesia under isoflurane.

Statistical Analyses

Results are expressed as mean±standard deviation (SD). Statistical comparisons among different groups were evaluated by analysis of variance (ANOVA). The animal mortality data were analyzed by the Kaplan-Meier survival estimate. A value of $p<0.05$ was considered statistically significant.

Having described the many embodiments of the disclosed invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

It is intended that the invention not be limited to the particular embodiment disclosed herein contemplated for carrying out this invention, but that the invention will include all embodiments falling within the scope of the claims.

REFERENCES

The following references are referred to above and are incorporated herein by reference:

1. Inglesby, T. V., O'Toole, T. & Henderson, D. A. Preventing the use of biological weapons: improving response should prevention fail. *Clin Infect Dis* 30, 926-929 (2000).
2. O'Toole, T. & Inglesby, T. V. Facing the biological weapons threat. *Lancet* 356, 1128-1129 (2000).
3. Inglesby, T. V., et al. Plague as a biological weapon: medical and public health management. Working Group on Civilian Biodefense. *JAMA* 283, 2281-2290 (2000).
4. Inglesby, T. V., et al. *Anthrax as a biological weapon, 2002*: updated recommendations for management. *JAMA* 287, 2236-2252 (2002).
5. Moayeri, M., Leppla, S. H., Vrentas, C., Pomerantsev, A. P. & Liu, S. Anthrax Pathogenesis. *Annu Rev Microbiol* 69, 185-208 (2015).
6. Williamson, E. D. & Dyson, E. H. Anthrax prophylaxis: recent advances and future directions. *Frontiers in microbiology* 6, 1009 (2015).
7. M., L., Joellenbeck, Lee L. Zwanziger, Jane S. Durch & Strom, a.B.L. *The Anthrax Vaccine: Is It Safe? Does It Work?*, (NATIONAL ACADEMY PRESS, Washington D.C, 2002).
8. Leppla, S. H., Robbins, J. B., Schneerson, R. & Shiloach, J. Development of an improved vaccine for anthrax. *J Clin Invest* 110, 141-144 (2002).
9. McComb, R. C. & Martchenko, M. Neutralizing antibody and functional mapping of *Bacillus anthracis* protective antigen—The first step toward a rationally designed anthrax vaccine. *Vaccine* 34, 13-19 (2016).
10. Elizabeth J. Valenti, C.o.t.R.C. Summary Basis for Regulatory Action Template. Vol. 2015 (2015).
11. Smiley, S. T. Current challenges in the development of vaccines for pneumonic plague. *Expert Rev Vaccines* 7, 209-221 (2008).
12. Zilinskas, R. A. The anti-plague system and the Soviet biological warfare program. *Crit Rev Microbiol* 32, 47-64 (2006).
13. Young, J. A. & Collier, R. J. Anthrax toxin: receptor binding, internalization, pore formation, and translocation. *Annu Rev Biochem* 76, 243-265 (2007).
14. Kaur, M., Singh, S. & Bhatnagar, R. Anthrax vaccines: present status and future prospects. *Expert Rev Vaccines* 12, 955-970 (2013).
15. Wagner, L., et al. Structural and immunological analysis of anthrax recombinant protective antigen adsorbed to aluminum hydroxide adjuvant. *Clin Vaccine Immunol* 19, 1465-1473 (2012).
16. D'Souza, A. J., et al. Rapid deamidation of recombinant protective antigen when adsorbed on aluminum hydroxide gel correlates with reduced potency of vaccine. *J Pharm Sci* 102, 454-461 (2013).
17. Rosenzweig, J. A., et al. Progress on plague vaccine development. *Appl Microbiol Biotechnol* 91, 265-286 (2011).
18. Stenseth, N. C., et al. Plague: past, present, and future. *PLoS Med* 5, e3 (2008).
19. Derewenda, U., et al. The structure of *Yersinia pestis* V-antigen, an essential virulence factor and mediator of immunity against plague. *Structure* 12, 301-306 (2004).
20. Williamson, E. D., et al. A new improved sub-unit vaccine for plague: the basis of protection. *FEMS Immunol Med Microbiol* 12, 223-230 (1995).
21. Anderson, G. W., Jr., Heath, D. G., Bolt, C. R., Welkos, S. L. & Friedlander, A. M. Short- and long-term efficacy of single-dose subunit vaccines against *Yersinia pestis* in mice. *Am J Trop Med Hyg* 58, 793-799 (1998).
22. Heath, D. G., et al. Protection against experimental bubonic and pneumonic plague by a recombinant capsular F1-V antigen fusion protein vaccine. *Vaccine* 16, 1131-1137 (1998).
23. Tao, P., et al. Mutated and bacteriophage T4 nanoparticle arrayed F1-V immunogens from *Yersinia pestis* as next generation plague vaccines. *PLoS Pathog* 9, e1003495 (2013).
24. Williamson, E. D., et al. Human immune response to a plague vaccine comprising recombinant F1 and V antigens. *Infect Immun* 73, 3598-3608 (2005).
25. Tao, P., Mahalingam, M. & Rao, V. B. Highly Effective Soluble and Bacteriophage T4 Nanoparticle Plague Vaccines Against *Yersinia pestis*. *Methods Mol Biol* 1403, 499-518 (2016).
26. Tao, P., et al. In vitro and in vivo delivery of genes and proteins using the bacteriophage T4 DNA packaging machine. *Proc Natl Acad Sci USA* 110, 5846-5851 (2013).
27. Tao, P., Li, Q., Shivachandra, S. B. & Rao, V. B. Bacteriophage T4 as a Nanoparticle Platform to Display and Deliver Pathogen Antigens: Construction of an Effective Anthrax Vaccine. *Methods Mol Biol* 1581(2017).
28. Fokine, A., et al. Molecular architecture of the prolate head of bacteriophage T4. *Proc Natl Acad Sci USA* 101, 6003-6008 (2004).
29. Qin, L., Fokine, A., O'Donnell, E., Rao, V. B. & Rossmann, M. G. Structure of the small outer capsid protein, Soc: a clamp for stabilizing capsids of T4-like phages. *J Mol Biol* 395, 728-741 (2010).
30. Li, Q., Shivachandra, S. B., Zhang, Z. & Rao, V. B. Assembly of the small outer capsid protein, Soc, on bacteriophage T4: a novel system for high density display of multiple large anthrax toxins and foreign proteins on phage capsid. *J Mol Biol* 370, 1006-1019 (2007).

31. Shivachandra, S. B., et al. In vitro binding of anthrax protective antigen on bacteriophage T4 capsid surface through Hoc-capsid interactions: a strategy for efficient display of large full-length proteins. *Virology* 345, 190-198 (2006).
32. Rao, M., et al. Highly effective generic adjuvant systems for orphan or povertyrelated vaccines. *Vaccine* 29, 873-877 (2011).
33. Scobie, H. M., Rainey, G. J., Bradley, K. A. & Young, J. A. Human capillary morphogenesis protein 2 functions as an anthrax toxin receptor. *Proc Natl Acad Sci USA* 100, 5170-5174 (2003).
34. Bradley, K. A., Mogridge, J., Mourez, M., Collier, R. J. & Young, J. A. Identification of the cellular receptor for anthrax toxin. *Nature* 414, 225-229 (2001).
35. Klimpel, K. R., Molloy, S. S., Thomas, G. & Leppla, S. H. Anthrax toxin protective antigen is activated by a cell surface protease with the sequence specificity and catalytic properties of furin. *Proc Natl Acad Sci USA* 89, 10277-10281 (1992).
36. Peachman, K. K., et al. Correlation between lethal toxin-neutralizing antibody titers and protection from intranasal challenge with *Bacillus anthracis* Ames strain spores in mice after transcutaneous immunization with recombinant anthrax protective antigen. *Infect Immun* 74, 794-797 (2006).
37. Parent, M. A., et al. Cell-mediated protection against pulmonary *Yersinia pestis* infection. *Infect Immun* 73, 7304-7310 (2005).
38. Ovsyannikova, I. G., et al. Human leukocyte antigens and cellular immune responses to anthrax vaccine adsorbed. *Infect Immun* 81, 2584-2591 (2013).
39. Rosenthal, J. A., et al. Mechanistic insight into the TH1-biased immune response to recombinant subunit vaccines delivered by probiotic bacteria-derived outer membrane vesicles. *PloS one* 9, e112802 (2014).
40. Albrecht, M. T., et al. Electroporation of a multivalent DNA vaccine cocktail elicits a protective immune response against anthrax and plague. *Vaccine* 30, 4872-4883 (2012).
41. Ren, J., et al. Protection against anthrax and plague by a combined vaccine in mice and rabbits. *Vaccine* 27, 7436-7441 (2009).
42. Griffin, K., et al. Protective efficacy of a recombinant plague vaccine when coadministered with another subunit or live attenuated vaccine. *FEMS Immunol Med Microbiol* 43, 425-430 (2005).
43. Williamson, E. D., et al. Co-immunisation with a plasmid DNA cocktail primes mice against anthrax and plague. *Vaccine* 20, 2933-2941 (2002).
44. Sha, J., et al. A non-invasive in vivo imaging system to study dissemination of bioluminescent *Yersinia pestis* CO92 in a mouse model of pneumonic plague. *Microb Pathog* 55, 39-50 (2013).
45. Agar, S. L., et al. Characterization of the rat pneumonic plague model: infectionkinetics following aerosolization of *Yersinia pestis* CO92. *Microbes Infect* 11, 205-214 (2009).
46. Heninger, S., et al. Toxin-deficient mutants of *Bacillus anthracis* are lethal in a murine model for pulmonary anthrax. *Infect Immun* 74, 6067-6074 (2006).
47. Twenhafel, N. A. Pathology of inhalational anthrax animal models. *Vet Pathol* 47, 819-830 (2010).
48. Do, Y., et al. Broad T cell immunity to the LcrV virulence protein is induced by targeted delivery to DEC-205/CD205-positive mouse dendritic cells. *Eur J Immunol* 38, 20-29 (2008).
49. Sathaliyawala, T., et al. Assembly of human immunodeficiency virus (HIV) antigens on bacteriophage T4: a novel in vitro approach to construct multicomponent HIV vaccines. *Journal of virology* 80, 7688-7698 (2006).
50. Peachman, K. K., et al. Anthrax vaccine antigen-adjuvant formulations completely protect New Zealand white rabbits against challenge with *Bacillus anthracis* Ames strain spores. *Clin Vaccine Immunol* 19, 11-16 (2012).
51. Bruttin, A. & Brussow, H. Human volunteers receiving *Escherichia coli* phage T4 orally: a safety test of phage therapy. *Antimicrob Agents Chemother* 49, 2874-2878 (2005).
52. Arora, N. & Leppla, S. H. Fusions of anthrax toxin lethal factor with shiga toxin and diphtheria toxin enzymatic domains are toxic to mammalian cells. *Infect Immun* 62, 4955-4961 (1994).
53. Ramirez, D. M., Leppla, S. H., Schneerson, R. & Shiloach, J. Production, recovery and immunogenicity of the protective antigen from a recombinant strain of *Bacillus anthracis*. *J Ind Microbiol Biotechnol* 28, 232-238 (2002).
54. Chen, Z., et al. Potent neutralization of anthrax edema toxin by a humanized monoclonal antibody that competes with calmodulin for edema factor binding. *Proc Natl Acad Sci USA* 106, 13487-13492 (2009).
55. Chaudhury S, Battaile K P, Lovell S, Plano G V, De Guzman R N.Structure of the *Yersinia pestis* tip protein LcrV refined to 1.65 A resolution. *Acta Crystallogr Sect F Struct Biol Cryst Commun*(2013) 69(Pt 5):477-81.
56. Zavialov A V, Tischenko V M, Fooks L J, Brandsdal B O, Aqvist J, Zav'yalov V P, et al. Resolving the energy paradox of chaperone/usher-mediated fibre assembly. *Biochem J* (2005) 389(Pt 3):685-94.
57. Tao, P., et al. A Bivalent Anthrax-Plague Vaccine That Can Protect against Two Tier-1 Bioterror Pathogens, *Bacillus anthracis* and *Yersinia pestis*. Front Immunol. 2017 Jun. 26; 8:687.

All documents, patents, journal articles and other materials cited in the present application are incorporated herein by reference.

While the disclosed invention has been disclosed with references to certain embodiments, numerous modification, alterations, and changes to the described embodiments are possible without departing from the sphere and scope of the disclosed invention, as defined in the appended claims. Accordingly, it is intended that the disclosed invention not be limited to the described embodiments, but that it has the full scope defined by the language of the following claims, and equivalents thereof.

What is claimed is:

1. An immunogenic composition comprising a triple fusion protein,
wherein the triple fusion protein comprises:
a mutated F1 antigen from *Yersinia pestis*,
a V antigen from *Yersinia pestis*, and
a protective antigen (PA) from *B. anthracis*;
wherein the mutated F1 antigen, the V antigen, and the PA are fused in-frame;
wherein the triple fusion protein has an immunogenicity of the mutated F1 antigen, an immunogenicity of the V antigen, and an immunogenicity of the PA, and
wherein PA has a size of at least 63 kDa.

2. The immunogenic composition of claim 1, wherein the mutated F1 antigen is fused in-frame to the N-terminus of the V antigen via a first linker, and wherein the V antigen is fused in-frame to the N-terminus of PA via a second linker.

3. The immunogenic composition of claim 1, wherein the mutated F1 antigen is modified from a native F1 antigen by deleting N-terminal β-strand residues 1-14 of native F1 antigen, transplanting the N-terminal β-strand residues 1-14 of native F1 antigen to C-terminus, and duplicating residues 15-21 of native F1 antigen at the C-terminus.

4. The immunogenic composition of claim 1, wherein the mutated F1 antigen comprises the sequence set forth in SEQ ID NO: 1.

5. The immunogenic composition of claim 1, wherein the triple fusion protein comprises the sequence set forth in SEQ ID NO: 4.

6. The immunogenic composition of claim 1, wherein the immunogenic composition comprises a pharmaceutically acceptable carrier.

7. The immunogenic composition of claim 1, wherein the immunogenic composition comprises an adjuvant.

8. An immunogenic composition comprising one or more bacteriophage nanoparticles arrayed with one or more Soc fusion proteins on capsid surface of each bacteriophage nanoparticle, wherein the one or more Soc fusion proteins comprises F1mut-V-PA, F1mut-PA and V-PA,
Wherein F1mut is -mutated F1 antigen from *Yersinia pestis*, V is V antigen from *Yersinia pestis* and PA is protective antigen (PA) from *B. anthracis*.

9. An immunogenic composition comprising a triple fusion protein,
wherein the triple fusion protein comprises:
a mutated F1 antigen from *Yersinia pestis*,
a V antigen from *Yersinia pestis*, and
a wild-type protective antigen (PA) from *B. anthracis*;
wherein the mutated F1 antigen, the V antigen, and the PA are fused in-frame;
wherein the triple fusion protein has an immunogenicity of the mutated F1 antigen, an immunogenicity of the V antigen, and an immunogenicity of the PA.

10. The immunogenic composition of claim 9, wherein the mutated F1 antigen is fused in-frame to the N-terminus of the V antigen via a first linker, and wherein the V antigen is fused in-frame to the N-terminus of PA via a second linker.

11. The immunogenic composition of claim 9, wherein the mutated F1 antigen is modified from a native F1 antigen by deleting N-terminal β-strand residues 1-14 of native F1 antigen, transplanting the N-terminal β-strand residues 1-14 of native F1 antigen to C-terminus, and duplicating residues 15-21 of native F1 antigen at the C-terminus.

12. The immunogenic composition of claim 9, wherein the mutated F1 antigen comprises the sequence set forth in SEQ ID NO: 1.

13. The immunogenic composition of claim 9, wherein the triple fusion protein comprises the sequence set forth in SEQ ID NO: 4.

14. The immunogenic composition of claim 9, wherein the immunogenic composition comprises a pharmaceutically acceptable carrier.

15. The immunogenic composition of claim 9, wherein the immunogenic composition comprises an adjuvant.

* * * * *